United States Patent [19]
Maddon et al.

[11] Patent Number: 5,110,906
[45] Date of Patent: May 5, 1992

[54] DERIVATIVES OF SOLUBLE T-4

[75] Inventors: Paul J. Maddon; Richard Axel, both of New York, N.Y.; Raymond W. Sweet, Bala Cynwyd, Pa.; James Arthos, Ann Arbor, Mich.

[73] Assignees: The Trustees of Columbia University in the City of New York, New York, N.Y.; Smithkline Beckman Corporation, Philadelphia, Pa.

[21] Appl. No.: 160,348

[22] Filed: Feb. 24, 1988

Related U.S. Application Data

[63] Continuation-in-part of Ser. No. 114,244, Oct. 23, 1987, which is a continuation-in-part of Ser. No. 898,587, Aug. 21, 1986, abandoned.

[51] Int. Cl.$^5$ .............................................. C07K 13/00
[52] U.S. Cl. ........................................ 530/350; 435/5; 435/974; 530/395; 530/829; 930/221
[58] Field of Search ............... 530/387, 395, 350, 829; 930/221; 435/5, 974

[56] References Cited

U.S. PATENT DOCUMENTS

| | | | |
|---|---|---|---|
| 4,520,113 | 5/1985 | Gallo et al. | 435/5 |
| 4,621,054 | 11/1986 | Suzuki et al. | 435/69 |
| 4,629,783 | 12/1986 | Cosand | 435/5 |
| 4,663,436 | 5/1987 | Elder et al. | 530/324 |

FOREIGN PATENT DOCUMENTS 8801304 2/1988 PCT Int'l Appl.

OTHER PUBLICATIONS

Littman, D. R. et al., *Chemical Abstracts*, vol. 103, p. 175, col. 1, Abstract No. 190738 (1985).
Littman, D. R. et al., *ICSU Short Rep.*, vol. 2, (Adv. Gene Tech.), pp. 233-234 (1985).
Maddon, P. J. et al., *Cell*, vol. 42, pp. 93-104 (1985).
Terhorst, C. et al., *Science*, vol. 209, pp. 520-521 (1980).
Maddon, P. J. et al., *Cell*, vol. 47, pp. 333-348 (1986).
McDougal, J. S. et al., *J. of Immunology*, pp. 2937-2944 (1986).
Isobe, M. et al., *Proc. Natl. Acad. Sci. U.S.A.*, vol. 83, pp. 4399-4402 (1986).
Ratner, L. et al., *Nature*, vol. 313, pp. 277-284 (1985).
Wong-Staal, F. et al., *Nature*, vol. 317, pp. 395-403 (1985).
Klatzmann, D. et al., *Nature*, vol. 312, pp. 767-768 (1984).

*Primary Examiner*—Christine Nucker
*Attorney, Agent, or Firm*—John P. White; Antoinette F. Konski

[57] ABSTRACT

This invention provides a therapeutic agent capable of specifically forming a complex with human immunodeficiency virus envelope glycoprotein which comprises a polypeptide. In one embodiment of the invention, the amino acid sequence of the polypeptide comprises the amino acid sequence shown in FIG. 6 from about +1 to about +185 fused to the amino acid sequence from about +353 to about +371. In another embodiment of the invention, the amino acid sequence of the polypeptide comprises the amino acid sequence shown in FIG. 6 from about +1 to about +106 fused to the amino acid sequence from about +353 to about +371. In yet a further embodiment of the invention, the amino acid sequence of the polypeptide comprises the amino acid sequence shown in FIG. 6 from about +1 to about +185.

This invention also provides a method for treating a subject infected with a human immunodeficiency virus. The method comprises administering to the subject an effective amount of a pharmaceutical composition comprising an effective amount of a therapeutic agent of the invention and a pharmaceutically acceptable carrier.

3 Claims, 36 Drawing Sheets

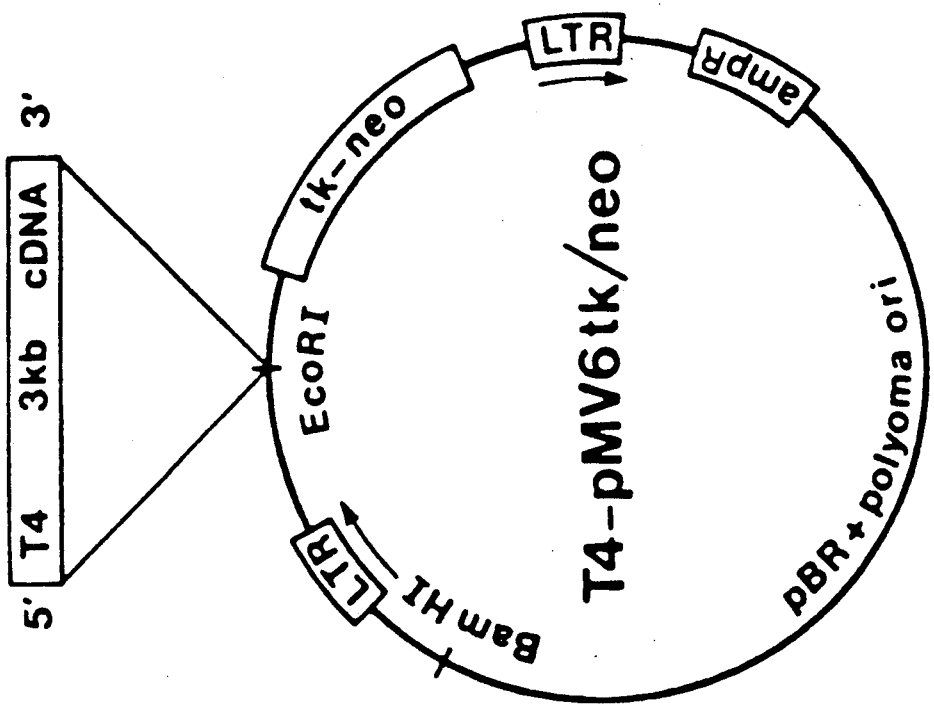
Figure 3C₂
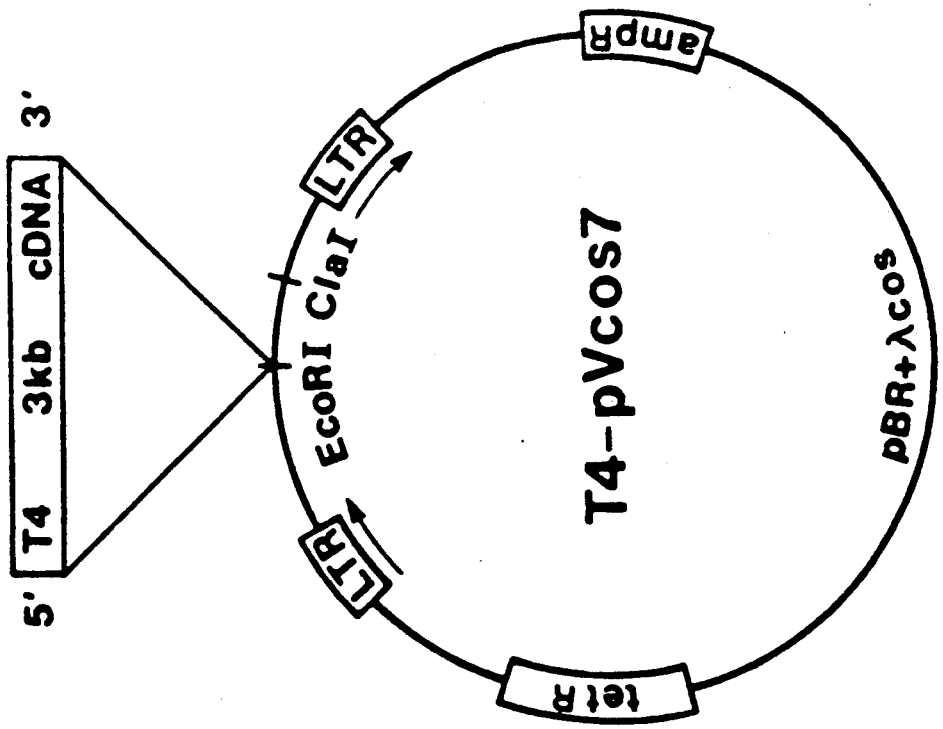
Figure 3C₁

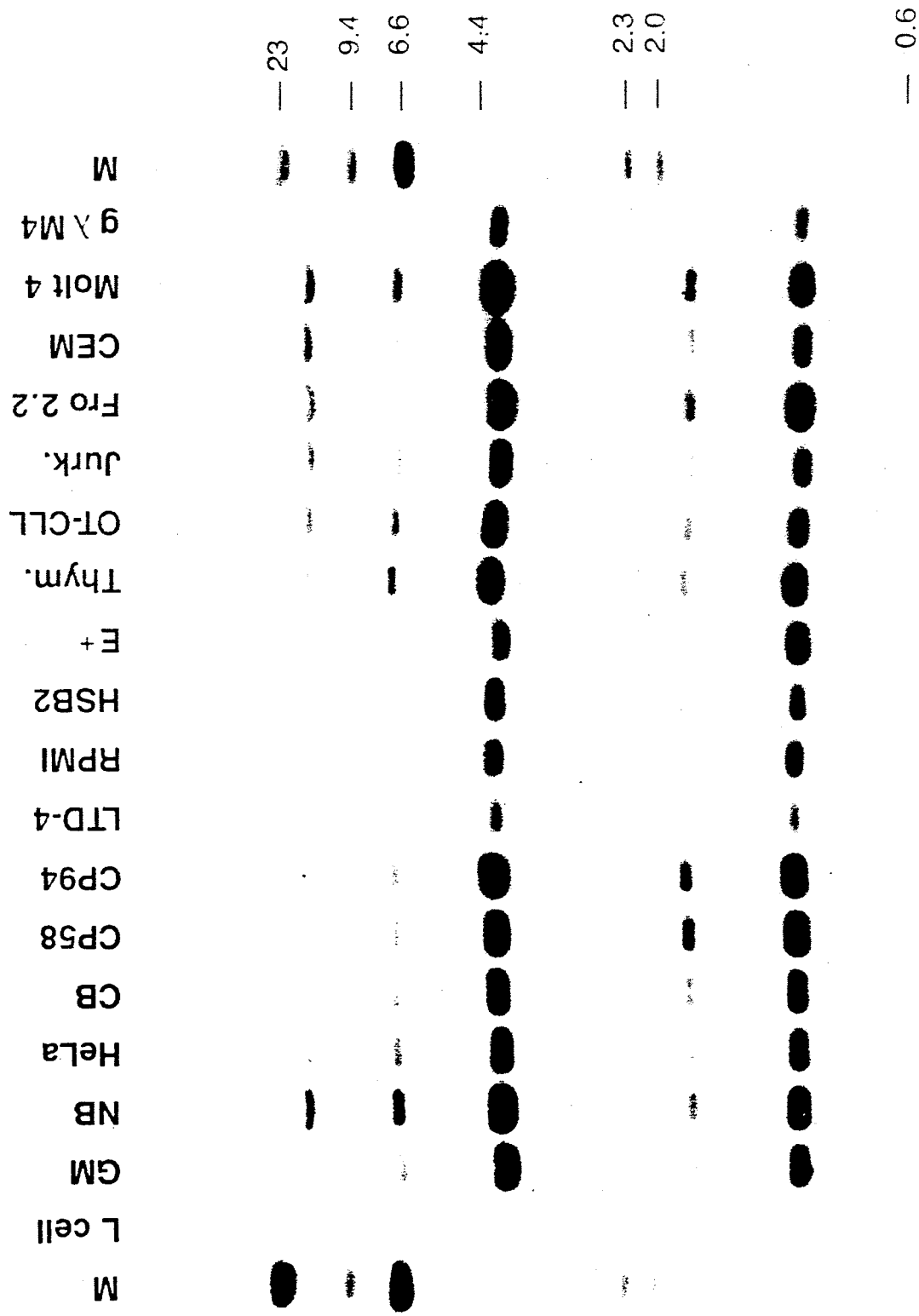

CAAGCCCAGAGCCCTGCCATT

TCTGTGGGCTCAGGTCCCTACTGCTCAGCAAGCCCCTTCCTCCCTCGGCAA

```
                                        -20
         met asn arg gly val pro phe arg his leu
GGCCACA  ATG AAC CGG GGA GTC CCT TTT AGG CAC TTG
         <-----------------------------------------

-10
leu leu val leu gln leu ala leu leu pro ala ala thr
CTT CTG GTG CTG CAA CTG GCG CTC CTC CCA GCA GCC ACT
----------------------------- L -------------------

-1  +1                                         +10
gln gly lys lys val val leu gly lys lys gly asp thr
CAG GGA AAG AAA GTG GTG CTG GGC AAA AAA GGG GAT ACA
-------> <------------ V1 --------------------------

●              +20
val glu leu thr cys thr ala ser gln lys lys ser ile
GTG GAA CTG ACC TGT ACA GCT TCC CAG AAG AAG AGC ATA
-----------  - - - - - -

+30
gln phe his trp lys asn ser asn gln ile lys ile leu
CAA TTC CAC TGG AAA AAC TCC AAC CAG ATA AAG ATT CTG +40                                   +50
gly asn gln gly ser phe leu thr lys gly pro ser lys
GGA AAT CAG GGC TCC TTC TTA ACT AAA GGT CCA TCC AAG +60
leu asn asp arg ala asp ser arg arg ser leu trp asp
CTG AAT GAT CGC GCT GAC TCA AGA AGA AGC CTT TGG GAC +70
gln gly asn phe pro leu ile ile lys asn leu lys ile
CAA GGA AAC TTC CCC CTG ATC ATC AAG AAT CTT AAG ATA
```

Figure 6B

```
                    +80                O
    glu asp ser asp thr tyr ile cys glu val glu asp gln
    GAA GAC TCA GAT ACT TAC ATC TAT GAA GTG GAG GAC CAG
                        --------- ——V1—————————

+90                                    +100
    lys glu glu val gln leu leu val phe gly leu thr ala
    AAG GAG GAG GTG CAA TTG CTA GTG TTC GGA TTG ACT GCC
    —————————————————————→ ←——————————————————————————

+110
    asn ser asp thr his leu leu gln gly gln ser leu thr
    AAC TCT GAC ACC CAC CTG CTT CAG GGG CAG AGC CTG ACC
    J1————————————————————————————————————→ ←———————————

+120
    leu thr leu glu ser pro pro gly ser ser pro ser val
    CTG ACC TTG GAG AGC CCC CCT GGT AGT AGC CCC TCA GTG
    ——V2——————————————————— ——————————————

+130                                  +140
          •
    gln cys arg ser pro arg gly lys asn ile gln gly gly
    CAA TGT AGG AGT CCA AGG GGT AAA AAC ATA CAG GGG GGG +150
    lys thr leu ser val ser gln leu glu leu gln asp ser
    AAG ACC CTC TCC GTG TCT CAG CTG GAG CTC CAG GAT AGT
                                                —————

O   +160
    gly thr trp thr cys thr val leu gln asn gln lys lys
    GGC ACC TGG ACA TGC ACT GTC TTG CAG AAC CAG AAG AAG
    ——————————— V2——————————————————————→ ←—

+170                              +180
    val glu phe lys ile asp ile val val leu ala phe gln
    GTG GAG TTC AAA ATA GAC ATC GTG GTG CTA GCT TTC CAG
    ——————————————————— J2———————————————————
```

Figure 6C

```
                                          +190
lys ala ser ser ile val tyr lys lys glu gly glu gln
AAG GCC TCC AGC ATA GTC TAT AAG AAA GAG GGG GAA CAG
 —→ ←—                 ——————— V3 ———————————————

+200
val glu phe ser phe pro leu ala phe thr val glu lys
GTG GAG TTC TCC TTC CCA CTC GCC TTT ACA GTT GAA AAG
— — — —

+210
leu thr gly ser gly glu leu trp trp gln ala glu arg
CTG ACG GGC AGT GGC GAG CTG TGG TGC CAG GCG GAG AGG +220                                    +230
ala ser ser ser lys ser trp ile thr phe asp leu lys
GCT TCC TCC TCC AAG TCT TGG ATC ACC TTT GAC CTG AAG +240
asn lys glu val ser val lys arg val thr gln asp pro
AAC AAG GAA GTG TCT GTA AAA CGG GTT ACC CAG GAC CCT +250
lys leu gln met gly lys lys leu pro leu his leu thr
AAG CTC CAG ATG GGC AAG AAG CTC CCG CTC CAC CTC ACC
— — — — — —  ——————— V3 ———————————

+260                                  +270
leu pro gln ala leu pro gln tyr ala gly ser gly asn
CTG CCC CAG GCC TTG CCT CAG TAT GCT GGC TCT GGA AAC
—————————————————→ ←——  ——————— J3 ——————

C H O                          +280
leu thr leu ala leu glu ala lys thr gly lys leu his
CTC ACC CTG GCC CTT GAA GCG AAA ACA GGA AAG TTG CAT
```

Figure 6D

```
                    +290
gln glu val asn leu val val met arg ala thr gln leu
CAG GAA GTG AAC CTG GTG GTG ATG AGA GCC ACT CAG CTC
─────────────────────────────────────── V4 ───────

+300    CHO  •                        +310
gln lys asn leu thr cys glu val trp gly pro thr ser
CAG AAA AAT TTG ACC TGT GAG GTG TGG GGA CCC ACC TCC
─── ───

+320
pro lys leu met leu ser leu lys leu glu asn lys glu
CCT AAG CTG ATG CTG AGC TTG AAA CTG GAG AAC AAG GAG +330
ala lys val ser lys arg glu lys ala val trp val leu
GCA AAG GTC TCG AAG CGG GAG AAG GCG GTG TGG GTG CTG +340                       •
asn pro glu ala gly met trp gln cys leu leu ser asp
AAC CCT GAG GCG GGG ATG TGG CAG TGT CTG CTG AGT GAC
─── ─── ─────────────── V4 ──────────

+350                                +360
ser gly gln val leu leu glu ser asn ile lys val leu
TCG GGA CAG GTC CTG CTG GAA TCC AAC ATC AAG GTT CTG
        ──────────────→ ←──────

+370
pro thr trp ser thr pro val gln pro met ala leu ile
CCC ACA TGG TCC ACC CCG GTG CAG CCA ATG GCC CTG ATT
─── J4 ──────────────────────────────→ ←───

+380
val leu gly gly val ala gly leu leu leu phe ile gly
GTG CTG GGG GGC GTC GCC GGC CTC CTG CTT TTC ATT GGG
─────────────────────────────────────── TM ───────
```

Figure 6E

```
     +390                                              +400
leu gly ile phe phe cys val arg cys arg his arg arg
CTA GGC ATC TTC TTC TGT GTC AGG TGC CGG CAC CGA AGG
─────────────────────────────────────────→ ←─────────

+410
arg gln ala glu arg met ser gln ile lys arg leu leu
CGC CAA GCA GAG CGG ATG TCT CAG ATC AAG AGA CTC CTC
────── C Y T ──────────────       ─ ─ ─ ─ ─

+420
ser glu lys lys thr cys gln cys pro his arg phe gln
AGT GAG AAG AAG ACC TGC CAG TGC CCT CAC CGG TTT CAG
                                             ─ ─ ─ ─ ─

+430
lys thr cys ser pro ile...
AAG ACA TGT AGC CCC ATT TGAGGCACGAGGCCAGGCAGATCCCAC
─────────────────────→

TTGCAGCCTCCCCAGGTGTCTGCCCCGCGTTTCCTGCCTGCGGACCAGAT

GAATGTAGCAGATCCCACGCTCTGGCCTCCTGTTCGTCCTCCCTACAATT

TGCCATTGTTTCTCCTGGGTTAGGCCCCGGCTTCACTGGTTGAGTGTTGC

TCTCTAGTTTCCAGAGGCTTAATCACACCGTCCTCCACGCCATTTCCTTT

TCCTTCAAGCCTAGCCCTTCTCTCATTATTTCTCTCTGACCCTCTCCCCA

CTGCTCATTTGGATCC
```

Figure 7
```
         BP  T4
92.5 —
66.2 —
 45  —
 31  —  
```
```
21.5 —  
```

|  | 100 | | | | | | | | | | |
|---|---|---|---|---|---|---|---|---|---|---|---|
| T4 J | L | V | F | G | L | - | T | A | N | S | D | T | H |
| Consensus Jβ | L | Y | F | G | E | G | T | R | L | T | V | L | - |
| Consensus Jλ | W | V | F | G | G | G | T | K | V | T | V | L | G |
| Consensus Jκ | - | T | F | G | G | G | T | K | L | E | I | K | R |
| HPB-MLTα J | I | I | F | G | S | G | T | R | L | S | I | R | - |

Figure 9C

```
              370                380              390
T4          S T P V Q P M A L I V L G G V A G L L F I G L G I F F C V R
MHC cl. IIβ S T S A Q N K M L S G V G G F V L G L L F L G L G L F I Y F R
                                        ─────────────────────────────
                                                    TM
```

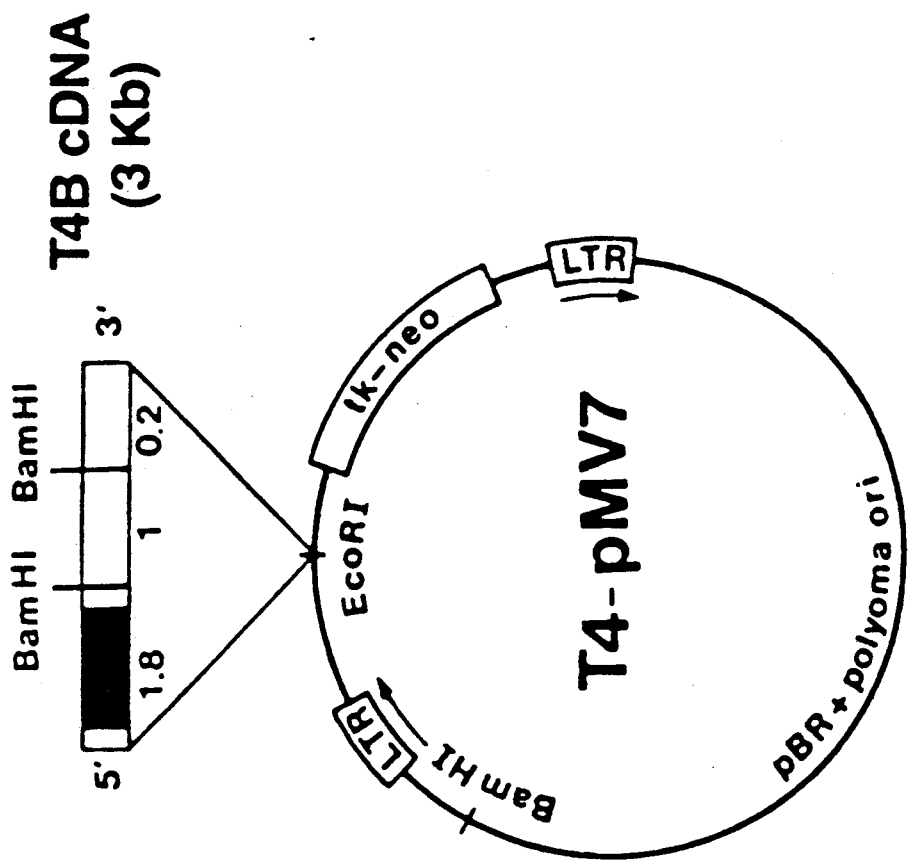
Figure 11A₂
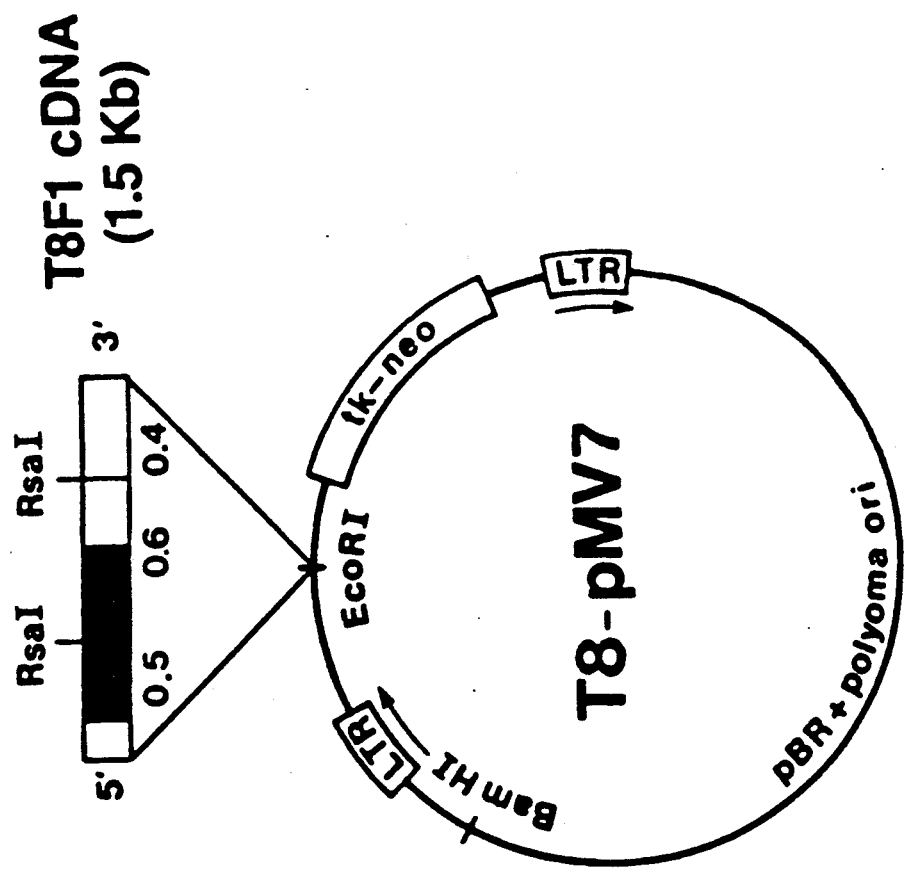
Figure 11A₁

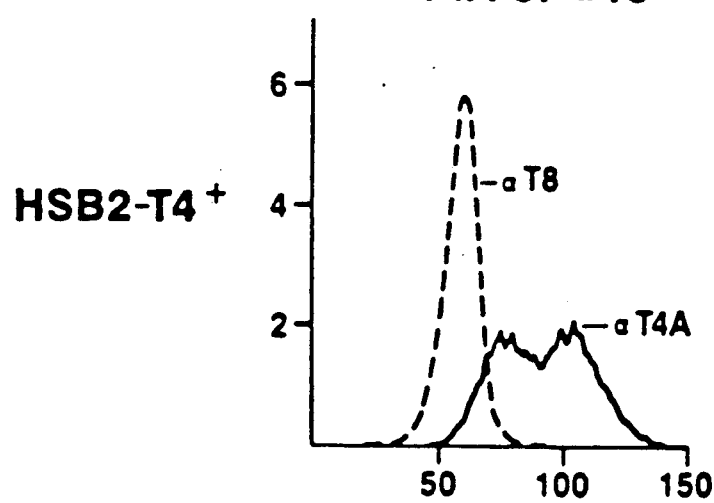
Figure 14A₁
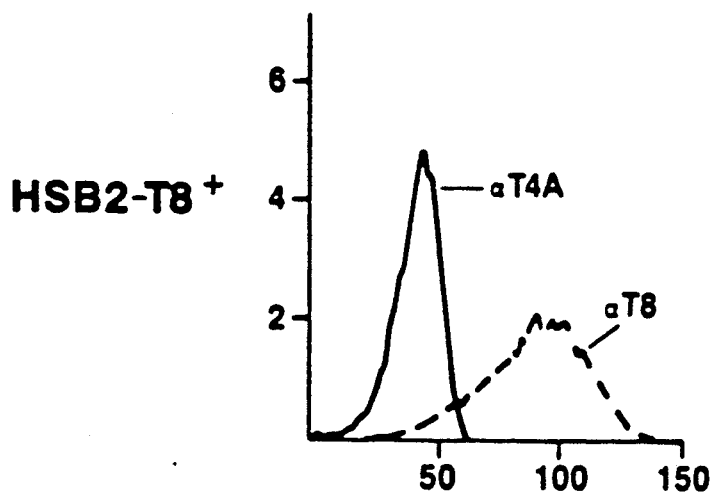
Figure 14A₂
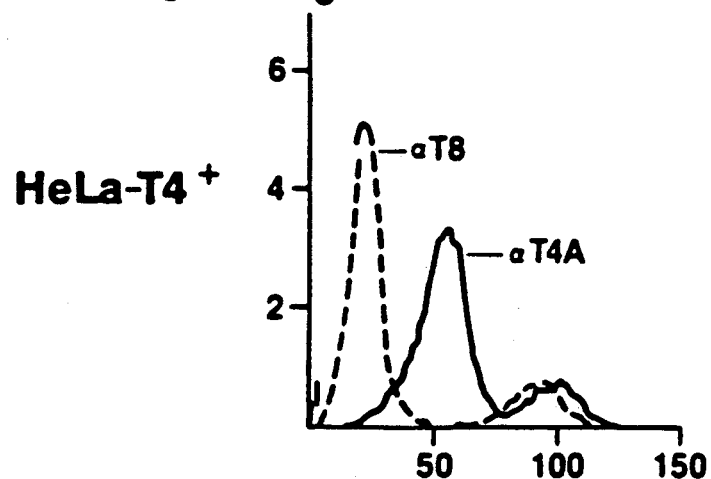
Figure 14A₃

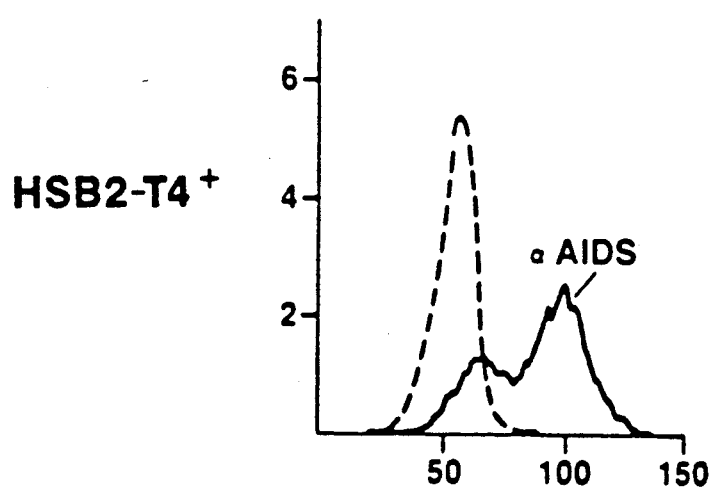
Figure 14B$_1$ AIDS/ αAIDS
HSB2-T4$^+$
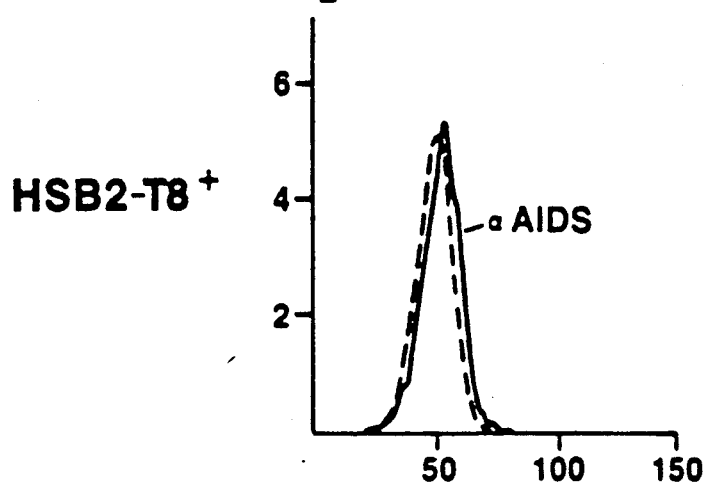
Figure 14B$_2$
HSB2-T8$^+$
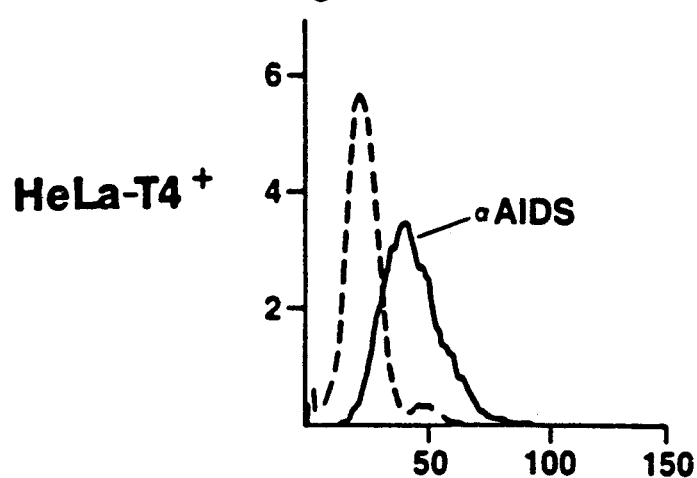
Figure 14B$_3$
HeLa-T4$^+$

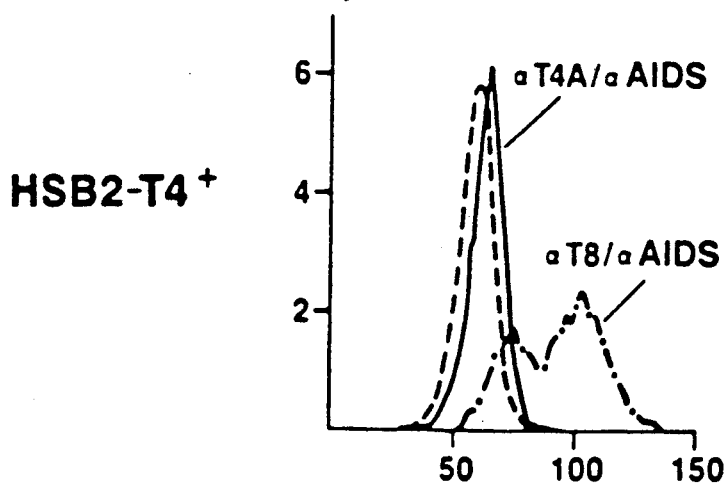
Figure 14C₁ αT4A or αT8/AIDS/αAIDS — HSB2-T4⁺
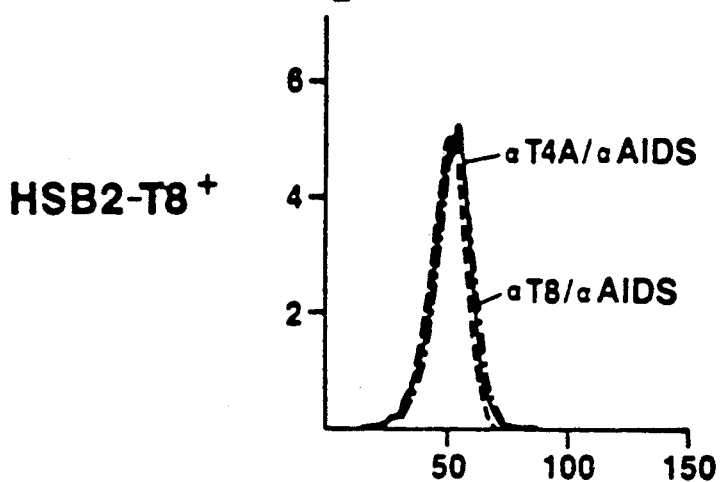
Figure 14C₂ — HSB2-T8⁺
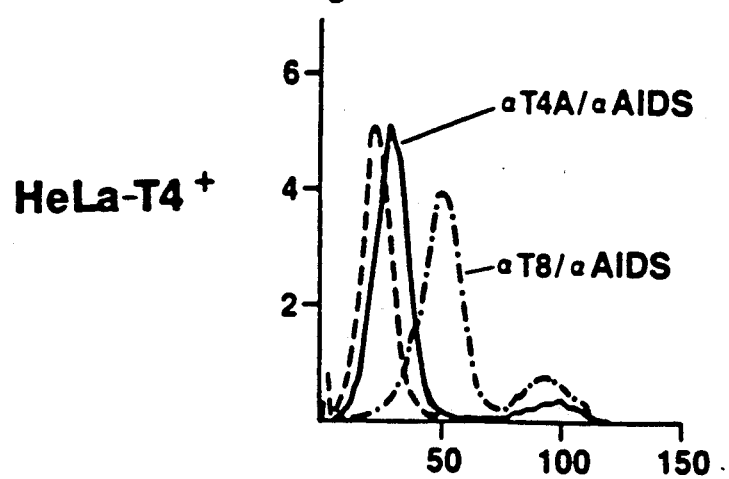
Figure 14C₃ — HeLa-T4⁺

T4     +370
— thr  pro  val  gin  pro  met  ala  leu —
— ACC  CCG  GTC  CAG  CCA  ATG  GCC  CTG — sT4
— thr  pro  val  ter
— ACC  CCG  GTG  TAA  TGGCGCCTCTAGA —
       HpaII         NarI     XbaI

DERIVATIVES OF SOLUBLE T-4

This application is a continuation-in-part of U.S. Ser. No. 114,244, filed Oct. 23, 1987, which is a continuation-in-part of U.S. Ser. No. 898,587, filed Aug. 21, 1986, now abandoned the contents of which are hereby incorporated by reference into the subject application.

BACKGROUND OF THE INVENTION

Within this application several publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

The different functional classes of T lymphocytes recognize antigen on the surface of distinct populations of target cells. Helper T cells interact largely with macrophages and B cells; cytotoxic T cells interact with a broader range of antigen-bearing target cells. These cellular recognition events are likely to be mediated by the specific association of surface molecules on both effector and target cells. The surface of T cells is characterized by a number of polymorphic, as well as nonpolymorphic, proteins which are restricted for the most part to T lymphocytes. Although most of these molecules are common to all T cells, two classes of surface proteins consistently differ on the different functional classes of T cells, and these proteins have been implicated in T cell-target cell interactions. coexpressed on the surface of thymocytes (1). In the peripheral immune system, the T4 and T8 molecules are expressed on mutually exclusive subsets of T cells and are only rarely expressed on the same cell (2, 3). The T4 molecule is expressed on T cells that interact with targets bearing class II major histocompatibility complex (MHC) molecules, whereas T8-bearing T cells interact with targets expressing class I MHC proteins (4, 5, 6, 7, 8, 9). The T4 population of T lymphocytes contains helper cells, whereas the T8 population contains the majority of cytotoxic and suppressor cells (6, 10). However, rare T4+T cells can function as cytotoxic or supressor cells (6, 10), suggesting that the expression of T4 or T8 is more stringently associated with MHC class recognition than with effector function. The significance of these molecules in T cell-target cell interactions can be demonstrated by studies with monoclonal antibodies. Antibodies directed against specific epitopes of the T4 molecule (or the murine equivalent L3T4) inhibit antigen-induced T cell proliferation, lymphokine release and helper cell function (7, 8, 11, 12, 13). Similarly, monoclonal antibodies directed against T8 (or the murine equivalent Lyt2) inhibit cytotoxic T cell-mediated killing (14, 15). These observations, along with the fact that T4 and T8 do not reveal significant polymorphism, has led to the hypothesis that T4 and T8 recognize nonpolymorphic regions of class II and class I molecules, respectively.

A second class of proteins thought to differ on different effector T cells are the receptors that recognize antigen in association with polymorphic regions of MHC molecules (16, 17, 18). The interactions of helper T lymphocytes are largely restricted to antigen-bearing target cells expressing class II MHC proteins, whereas phic determinants of MHC proteins, and these receptors may be responsible for specific targeting of functionally distinct populations of T cells. The human acquired immune deficiency syndrome (AIDS) is characterized by a depletion of T4+ lymphocytes As a consequence, T cell-mediated immunity is impaired in AIDS patients, resulting in the occurrence of severe opportunistic infections and unusual neoplasms. AIDS results from the infection of T lymphocytes with a collection of closely related retroviruses (LAV, HTLVIII, or ARV), now termed human immunodeficiency virus (HIV). The range of infectivity of these agents is restricted to cells expressing the T4 glycoprotein on their surface.

Therefore, the T4 glycoprotein may serve not only as a receptor for molecules on the surface of target cells, but also as a receptor for the AIDS virus. Monoclonal antibodies directed against T4 block AIDS virus infection of T4+ cells in vitro. Furthermore, recent studies have demonstrated that when T4+T lymphocytes are exposed to AIDS virus, the 110 kd envelope glycoprotein of the virus is associated with the T4 molecule on the host cell. The lymphotropic character of the virus could therefore be explained by the restricted expression of its receptor, T4, in subpopulations of T lymphocytes.

The depletion of T4+T lymphocytes in AIDS results in the impairment of the cellular immune response. In addition, AIDS is frequently accompanied by central nervous system (CNS) dysfunction, most often the consequence of a subacute encephalitis. AIDS virus RNA and DNA has been identified in affected brains, and virus has been isolated from both brain and cerebrospinal is also expressed in the CNS or whether additional brain-specific surface molecules may serve as a receptor for the AIDS virus.

The elucidation of the specific interactions of T4 and T8 would be facilitated by the isolation of the T4 and T8 genes, the determination of their structure, and the ability to introduce them into different cellular environments. The isolation and sequence of a cDNA encoding the T8 molecule has recently been reported (19, 20, 21). The deduced protein sequence indicates that T8 is a membrane-bound glycoprotein with an N-terminal domain that bears homology to the variable region of immunoglobulin light chains.

SUMMARY OF THE INVENTION

This invention provides a therapeutic agent capable of specifically forming a complex with human immunodeficiency virus envelope glycoprotein comprising a polypeptide In one embodiment of the invention, the amino acid sequence of the polypeptide comprises the amino acid sequence shown in FIG. 6 from about +1 to about +185 directly fused to the amino acid sequence from about 353 to about +371. In another embodiment of the invention, the amino acid sequence of the polypeptide comprises the amino acid sequence shown in FIG. 6 from about +1 to about +106 directly fused to the amino acid sequence from about +353 to about +371. In yet a further embodiment of the invention, the amino acid sequence of the polypeptide comprises the amino acid sequence shown in FIG. 6 from about +1 to about +185.

This invention also provides a method for treating a subject infected with a human immunodeficiency virus. The method comprises administering to the subject an effective amount of a pharmaceutical composition comprising an effective amount of a therapeutic agent of the invention and a pharmaceutically acceptable carrier.

Cells ($5 \times 10^5$) were incubated with the mouse monoclonal antibodies OKT®4B or OKT®8, washed, and then incubated with FITC conjugated goat anti-mouse immunoglobulin. The cells were analyzed on a FACS IV Cell Sorter and plotted by a VAX 11/780 computer as cell number vs. log fluorescence. Untransformed NIH 3T3 cells and L cells gave identical cytofluorographic tracings. Fro 2.2 is a leukemic T cell line with phenotype T3−; T4+; T8+; T11 +. LTD-4 is a T4+primary L cell transformant obtained following transfer of total genomic DNA. 3A+ is an NIH 3T3 cell line that was transformed with the T4-pMV6tk/neo retroviral expression construct.

Figure 1A:
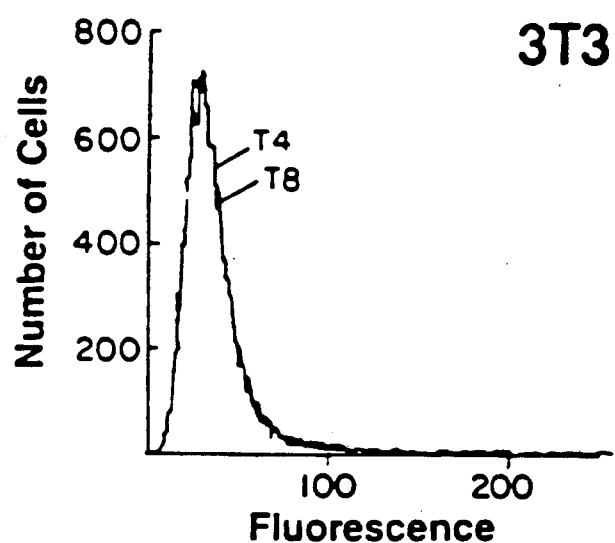
FIG. 1A, B, C and D Cytofluoroqraphic Patterns of Indirect Immunofluorescent Staining with OKT®4 and OKT®8
Figure 1B:
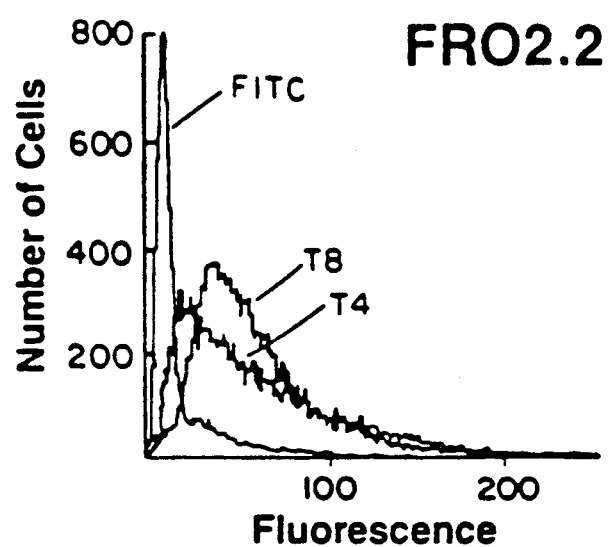
Figure 1C:
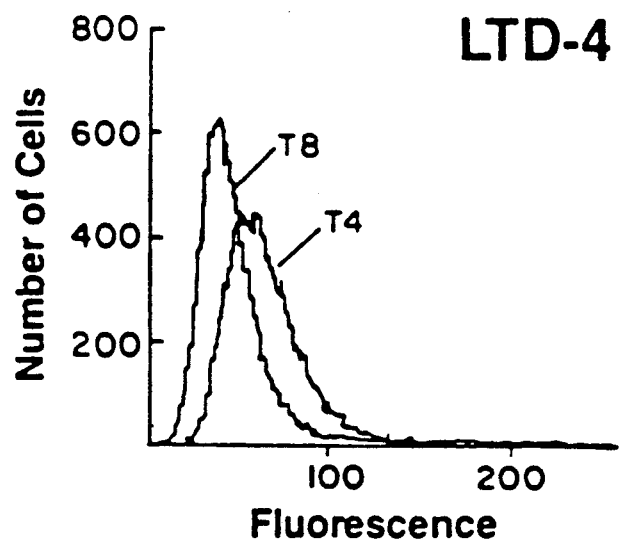
Figure 1D:
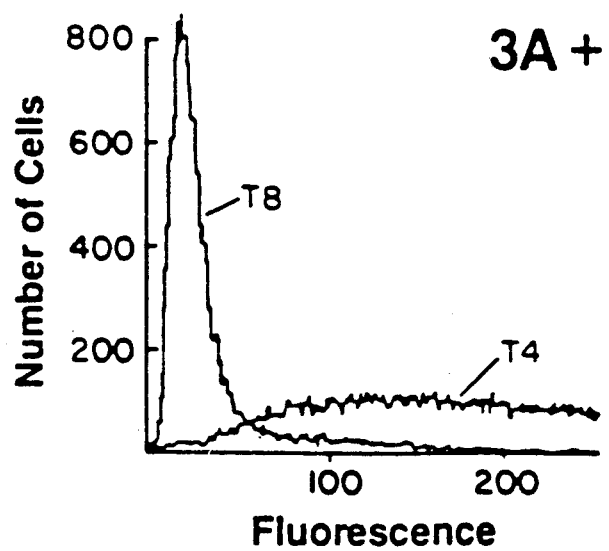
Figure 2:
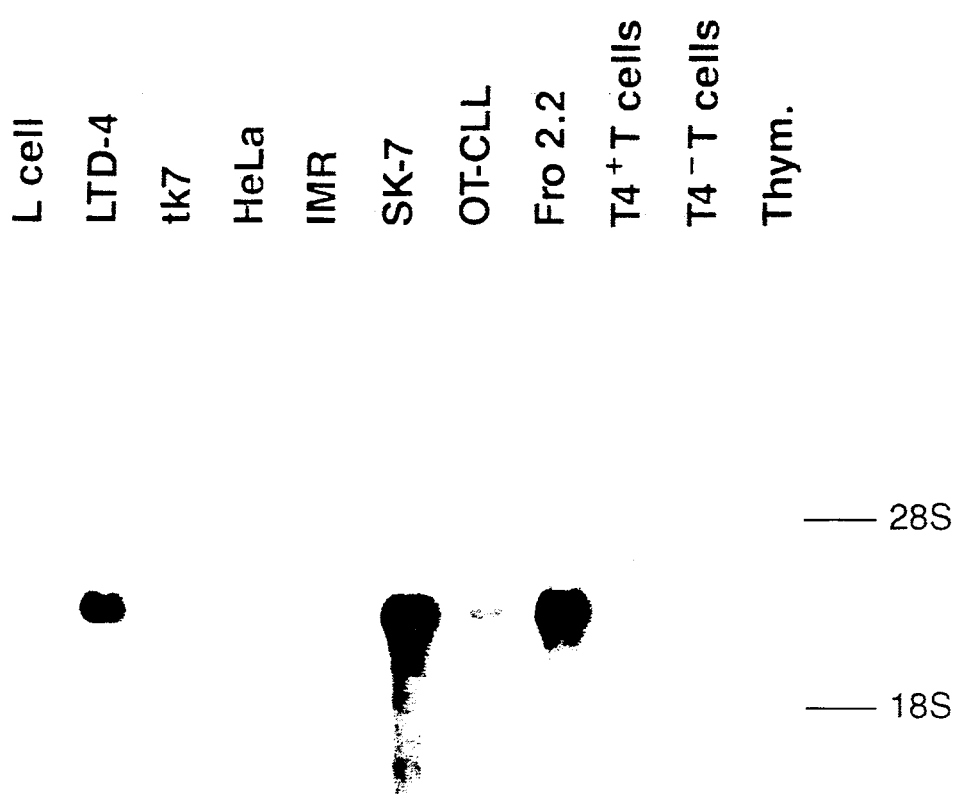

FIG. 2. Northern Blot Analysis of RNA Derived from T4+ and T4− L Cells and Human Cells Three micrograms of poly(A)+RNA or 12 μg of total RNA (peripheral T cells and thymocytes) were electrophoresed through a 0.8% agarose-formaldehyde gel, blotted onto GeneScreen (New England Nuclear), and probed with a $^{32}$P-labeled 0.6 kb T4 cDNA insert. T4+cells include LTD-4 (T4+, T8−L cell transformant), SK-7 T cell hybridoma (T4+, T8−), TO-CLL leukemia (T4+, T8−), Fro 2.2 leukemia (T4+, T8−), T4−enriched peripheral T lymphocytes, and human thymocytes. T4−cells include untransformed cells, tk7 (T8+L cell transformant), HeLa cells, human neuroblastoma cells (IMR), and T8enriched peripheral T lymphocytes. The human thymocyte lane was exposed four times longer and photographed on high contrast film.

FIG. 3. Restriction Nuclease Maps of pT4B and the T4 Gene, Sequencing Strategy, and Recombinant Vectors 3A. Alignment of the Bam HI restriction fragments of pT4B cDNA and the T4 gene. The order of Bam HI fragments in the T4 gene was determined by Southern blot analysis and genomic clone mapping. The alignment of the 5'end of pT4B and the T4 gene is shown by dotted lines, and the shaded region in pT4B corresponds to the coding sequence. The indicated sizes are in kilobases.

3B. Sequencing strategy. Arrows indicate length cf sequence determined by subcloning fragments into M13 and sequencing by the dideoxy termination procedure (36).

3C. Eukaryotic expression vectors. These constructs contain two Moloney murine leukemia virus long terminal repeats (LTRs) whose orientations are indicated by arrows. The pT4B cDNA was subcloned into the Eco RI site of each vector in the orientation indicated. (a) The T4−pVcos7 construct. (b) The T4−pMV6tk/neo construct contains the neomycin phosphotransferase gene fused to the HSV thymidine kinase promoter.

FIG. 4. Southern Blot Analysis of DNA from Untransformed and T4+L Cells and T, B, and Nonlymphoid Human Cells Ten micrograms of cellular DNAs were digested with Bam HI, electrophoresed through a 0.8% agarose gel, blotted onto GeneScreen, and probed with a nick-translated pT4B cDNA insert. The indicated size markers are in kilobases. Hybridizing bands of sizes 20 kb, 6.6 kb, 4 kb, 1.8 kb, and 1 kb appear in all human DNAs. DNAs from T4−, nonlymphoid origin include untransformed L cells, human fibroblasts (GM), human neuroblastoma cells (NB), and HeLa cells. CB, CP58, and CP94 are DNAs derived from EBV-transformed human B cell lines. LTD-4 is the T4−primary L cell transformant. RPMI and HSB2 are T4−human T cell leukemic lines; E+cells and thymocytes (Thym.) contain T4+T cells. TO-CLL, Jurkat (Jurk.), Fro 2.2, CEM, and Molt 4 are T4+T cells. gλM4 is a genomic clone which contains sequences spanning the 3'end of the T4 gene.

Figure 5:

FIG. 5. Immunoprecipitation of the T4 Glycoprotein from NIH 3T3 Cells Transformed with the Retroviral Expression Constructs L-[$^{35}$S]-methionine labeled proteins from two independent NIH 3T3 transformants, peripheral T lymphocytes, and untransformed 3T3 cells were subjected to lentil lectin chromatography to enrich for glycoproteins. $2.5 \times 10^6$ cpm of each sample was precleared and then immunoprecipitated with OKT®4 monoclonal antibodies and Protein A-Sepharose. The beads were washed, dissolved in sample buffer, and electrophoresed through a 10% SDS-polyacrylamide gel under reducing (lanes a-d) and nonreducing (lanes e and f) conditions. Lane a, untransformed NIH 3T3 cells. Lane b, T4C2, an NIH 3T3 cell transformed with the T4−pVcos7 construct. Lanes c and e, 3A+, an NIH 3T3 cell transformed with the T4pMV6tk/neo construct. Lanes d and f, peripheral human T lymphocytes. Relative molecular masses ($M_r$) are given in kilodaltons.

Figure 3A:
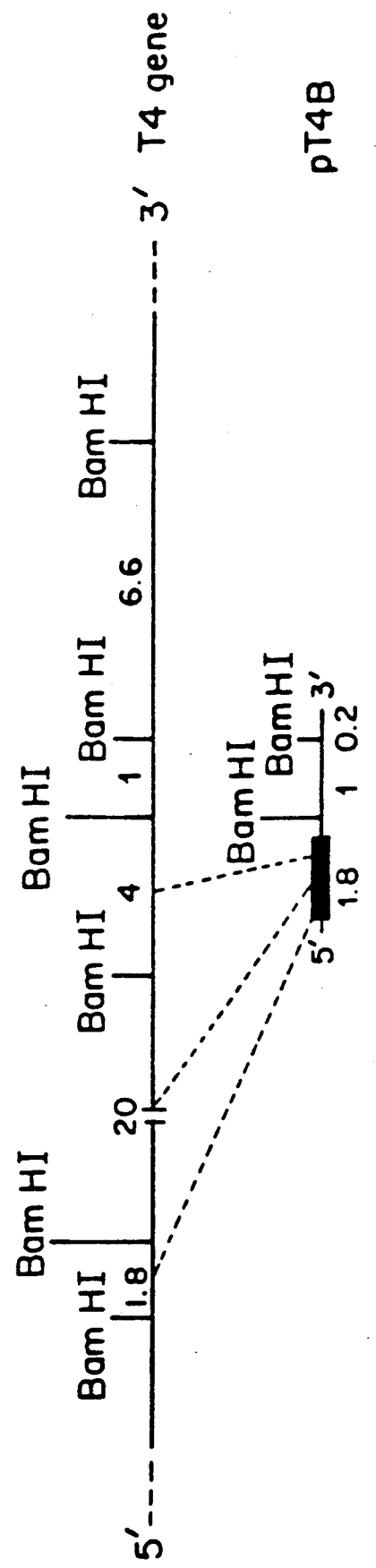
Figure 3B:
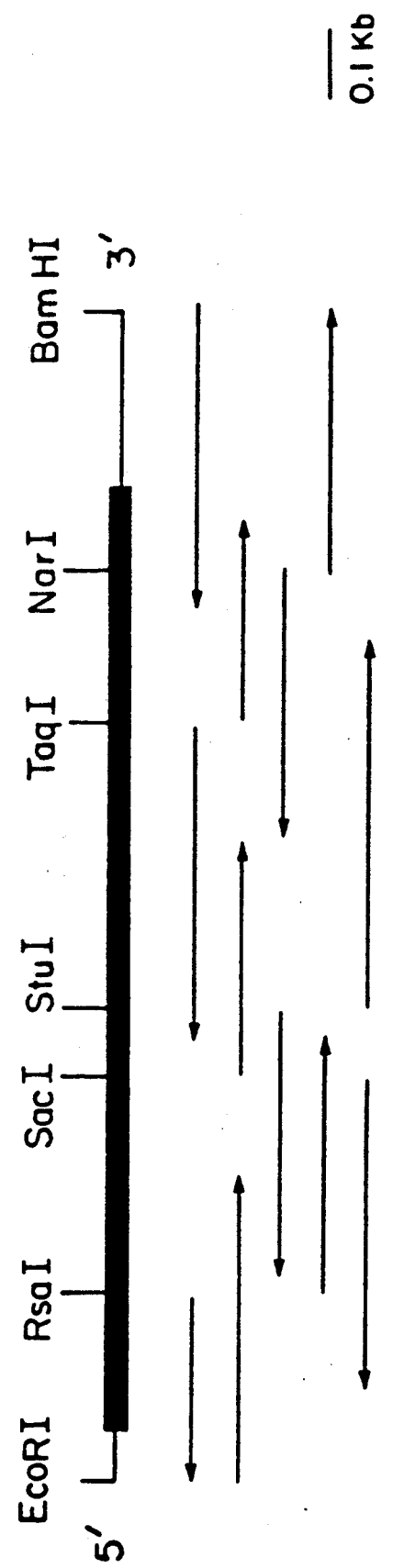

FIG. 6A, B, C, D and E Nucleotide Sequence of the T4 cDNA and Translated Sequence of the T4 Protein The nucleotide and predicted amino acid sequences of the cDNA clone pT4B obtained according to the sequencing strategy outlined in FIG. 3B. Numbers shown above the amino acid sequence designate amino acid residue positions. The numbers on the right show nucleotide positions. All extracellular cysteines are marked by (●) or (○). The leader sequence (L), variable-like (V), joining-like (J), transmembrane (TM), and cytoplasmic (CYT) regions are indicated by horizontal arrows below the sequence, although the exact cosylation sites (Asn-Leu-Thr) are also indicated (CHO).

FIG. 7. In Vitro Translation RNA derived from SP6 Transcription

The full length T4 cDNA insert was subcloned into the RNA expression vector pSP65 (Promega Biotec). Linearized plasmid DNA was transcribed with SP6 polymerase (40), and RNA was translated in a wheat germ system (Bethesda Research Laboratories) containing L-[$^{35}$S]-methionine. The in vitro translation products were subjected to electrophoresis through a 10% SDS-polyacrylamide gel (lane T4). Bovine pituitary RNA (BP) was used as a control Relative molecular masses ($M_r$) are given in kilodaltons.

Figure 8:
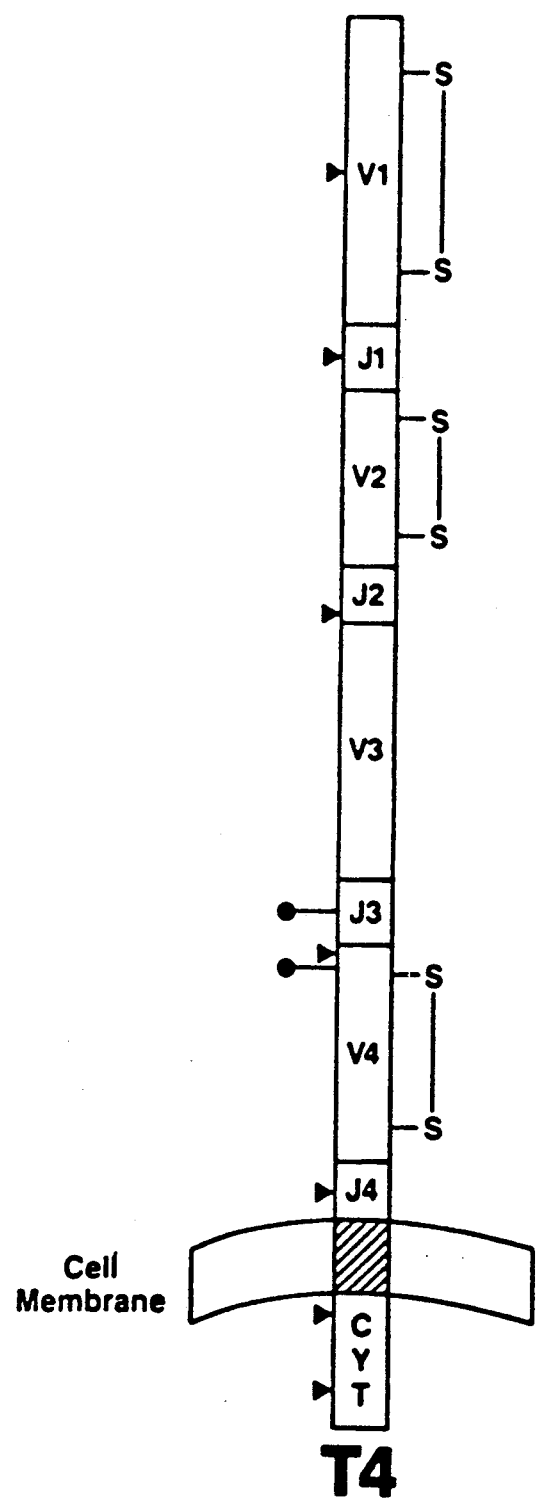

FIG. 8: Schematic diagram of the T4 qlycoprotein spanning the cell membrane T4 consists of four tandem VJ-like domains ($V_1J_1-V_4J_4$), a hydrophobic membrane-spanning segment (shaded area), and a charged cytoplasmic region (CYT). Two potential N-linked glycosylation sites in the extracellular portion are indicated (●) The positions of introns 2—8 in the T4 gene are also marked (▲).

Figure 9A:
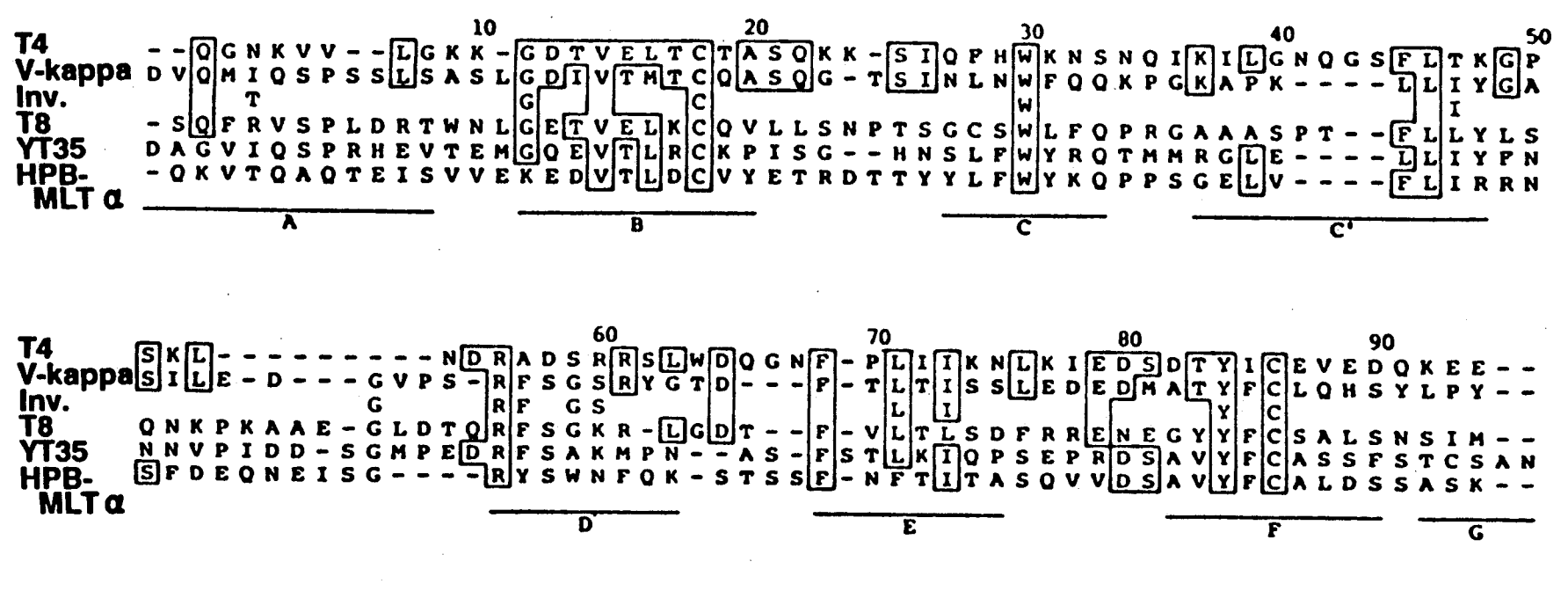

FIG. 9A, B and C. Alignment of the Variable, Joining, and Transmembrane Regions of T4 with Members of the Immunosmembran globulin Gene Family 9A. Alignment of the variable region amino acid sequence of T4 with a mouse kappa light chain immunoglobulin J606 (66), T8 (20), a human T cell antigen receptor β-chain YT35 (97), and a human T cell antigen receptor α-chain HPB-MLT α(98). The invariant residues in the light chain variable region are included (Inv.) in the alignment. The alignment was performed in order to maximize identities and structural homologies with T4, which appear as boxed residues. The lines below the sequence with letters A, B, C, C', D, E, F, and G indicate the residues which form β-strands (67). β-strand G continues into the J sequence.

9B. Alignment of the joining region amino acid sequence of T4 with the consensus J sequences of the T cell antigen receptor β-chain, immunoglobulin lambda and kappa light chains, and the J sequence of the human T cell receptor α-chain (99).

9C Alignment of the transmembrane regions of T4 and an MHC class II β-chain (100). The putative transmembrane domain (TM) is indicated below the sequence.

Figure 10:
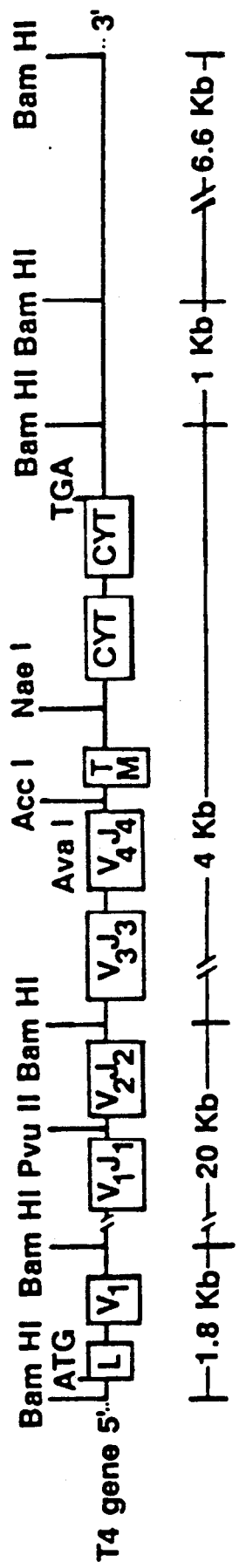

FIG. 10. Restriction nuclease map of the T4 gene in human chromosomal DNA

The positions of the 9 exons were determined by genomic clone mapping, Southern blot analysis, and nucleotide sequencing. The leader sequence (L), variable-like (V), joining-like (J), transmembrane (TM), and cytoplasmic (CYT) regions are boxed. The position of the methionine codon surrounded by the intitiation consensus sequence is indicated (ATG) at the beginning of the leader exon (L); the termination codon TGA is shown at the end of the second cytoplasmic exon (CYT). The indicated sizes are in kilobases.

FIG. 11A1 A2, and B. Recombinant Retroviral Expression Vectors and Construction of Transformed Cells 11 A1, and A2. Recombinant retroviral expression vectors. pMV7 contains two directly repeated Moloney murine sarcoma virus long terminal repeats (LTRs) in the orientation indicated by arrows. pMV7 also contains the bacterial neomycin phosphotransferase gene (neo) fused to the HSV thymidine kinase promoter (tk). Full length cDNA inserts encoding T4 (T4B) (70) or T8 (T8F1) (20) were subcloned into the Eco RI site in the orientation indicated by arrows, generating T4-pMV7 and T8-pMV7, respectively. The coding sequences are shown as shaded regions. The indicated sizes are in kilobases.

11B. Retrovirus-Mediated Gene Transfer Strategy.

Figure 12:
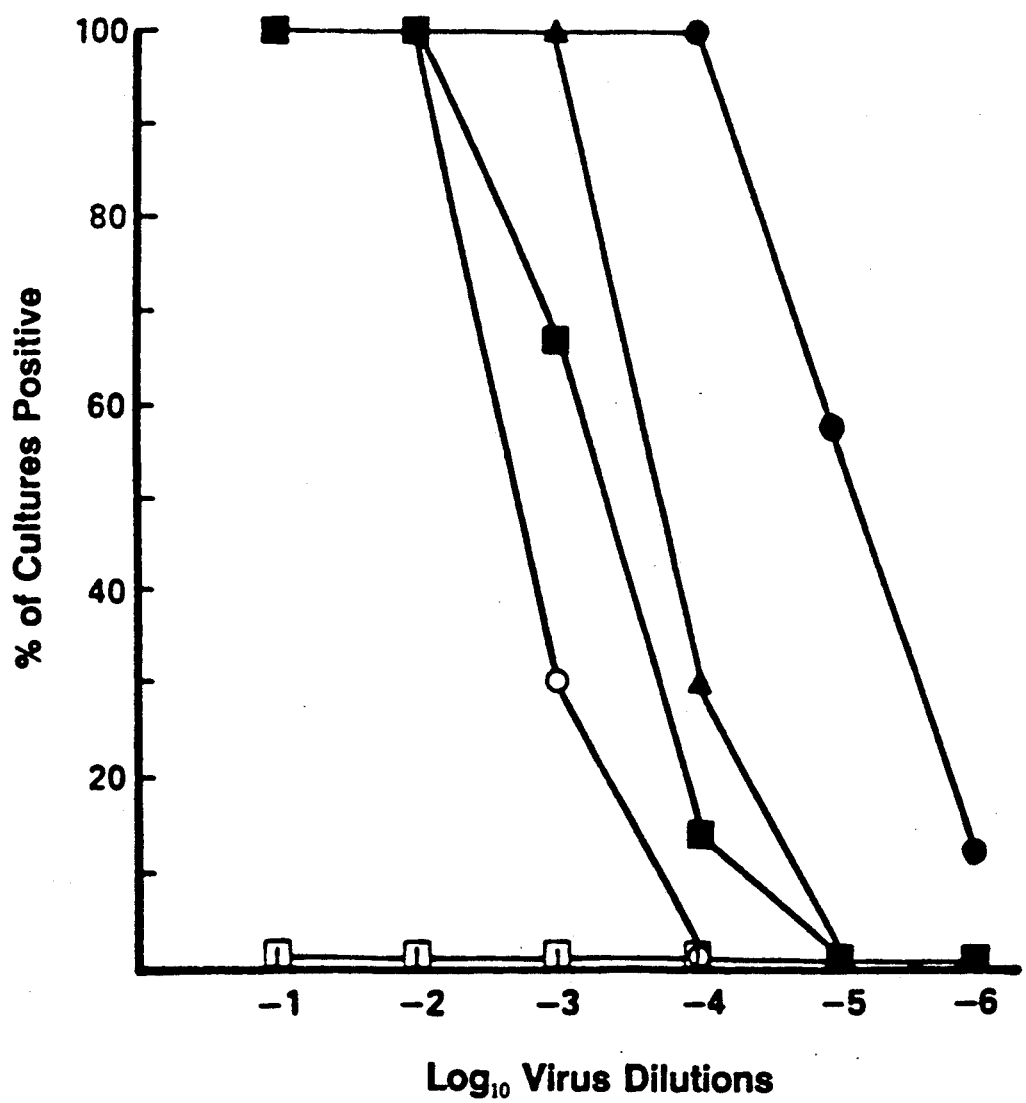

FIG. 12. The Efficiency of Infection of Naturally-Isolated and Transformed T4+Cells Cells were inoculated with serial $10^{-}$fold dilutions of AIDS virus, incubated for 18 hours at 37.C, washed, and plated in microculture. The frequency of infected cultures was determined by an enzyme-linked immunoabsorbent assay (ELISA) 12 days post-infection (46). The results were plotted as % positive cultures vs. log virus dilution. Infectious virus titer (ID-50) is defined as the reciprocal of the dilution at which 50% of the cultures are positive for virus (47). Naturally isolated T4+cells include phytohemagglutinin (PHA)-stimulated normal peripheral lymphocytes ( ●—● ) and the T cell line CEM (○—○). T4+transfected cell lines include HSB2-T4+T cells ( ■—■ ) and Raji-T4+B cells ( — ). The T8+transfected cell lines HSB2-T8+and Raji-T8+(□—□) served as controls in these studies.

Figure 13A:
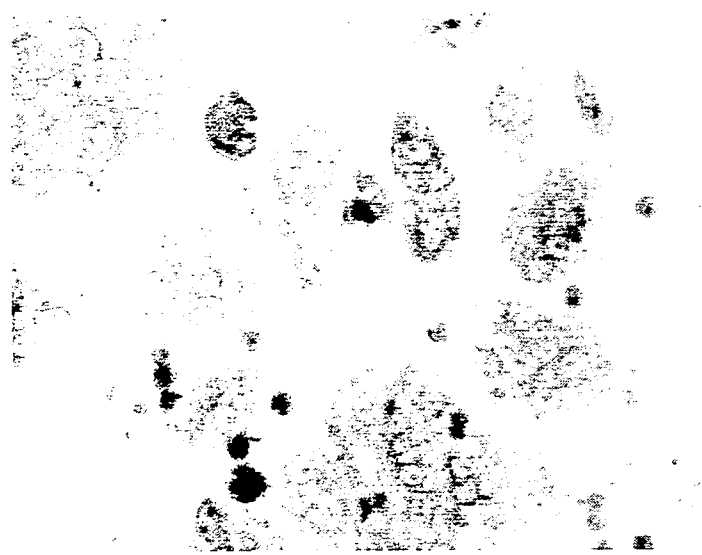
Figure 13B:
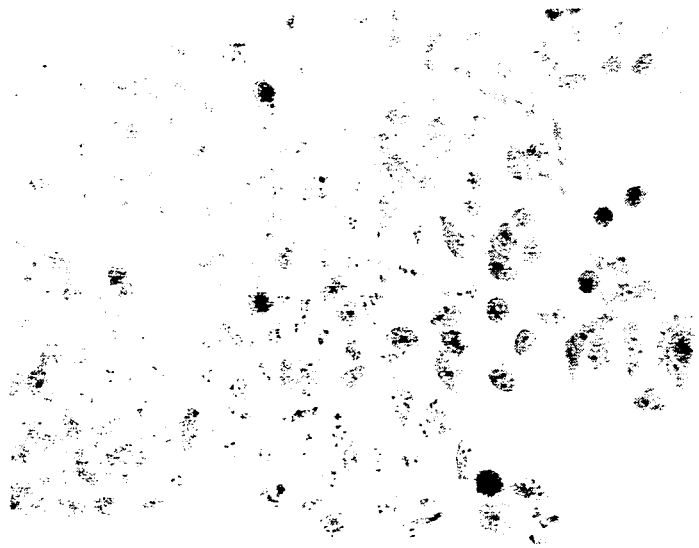

FIG. 13. Formation of Syncthia in T4+HeLa Tranformants

13A. $2\times10^5$ monolayer HeLa-T$^4$+ tranformants were mixed with $2\times10^4$ AIDS virus-producing H9 cells and incubated at 37° C. Inspection of the cultures after 18 hours revealed that over 90% of nuclei in the monolayer sheet were contained within syncytia.

13B. Anti-T4A monoclonal antibody (1:20) was added to the mixed cultures at the time of seeding. Inspection of the cultures after 18 hours revealed a complete absence of cell fusion.

Cultures were photographed at 160 X magnification.

FIG. 14. Flow Cytometry Analysis of AIDS Virus binding to T4+Transformed Cells

FIG. 14A1, 14A2, 14A3. Cells $(5\times10^5)$ were incubated with fluores- cein-conjugated anti-T4A (—) or anti-T8 (—) monoclonal antibodies, washed, and analyzed by cytofluorometry FIG. 14B, 14B2, 14B3. Cells $(5\times10^5)$ were incubated with buffer (—), or AIDS virus (—), washed, incubated with fluorescein-conjugated anti-AIDS virus antibody, and analyzed by cytofluorometry.

FIG. 14C1, 14C2, 14C3. Cells $(5\times10^5)$ were incubated with buffer (—), or with anti-T4A monoclonal antibody followed by AIDS virus (—), or with anti-T8 monoclonal antibody followed by AIDS virus ( ●—● ) After a wash, fluorescein-conjugated anti-AIDS virus antibody was added and the cells were analyzed by cytofluorometry.

Fluorescence histograms (cell number vs. fluorescence intensity) of each cell line are arranged horizontally.

FIG. 15. Northern Blot Analysis of RNA Derived from Human and Mouse Brain, Lymphoid, and Myeloid Cells 15A. Northern blot analysis of human RNA samples. One microgram of poly(A)+RNA from Raji (T4$^-$B cell line), U937 (T4+monocytic cell line), and Jurkat (T4 T cell line), and five micrograms of poly(A)+RNA from cerebral cortex, were electrophoresed through a 1% agaroseformaldehyde gel, blotted onto Hybond (Amersham), and probed with a $^{32}$P-labelled T4 cDNA insert, pT4B (70).

15B. Northern blot analysis of mouse RNA samples. Five micrograms of poly(A)+RNA from 3T3 cells (fibroblast cell line), forebrain, and hindbrain, and 20 micrograms of total RNA from thymocytes, were eletrophoresed through a 1% agarose-formaldehyde gel, transferred onto Hybond, and probed with a $^{32}$ P-labelled L3T4 cDNA insert, pL3T4B.

Figure 16:
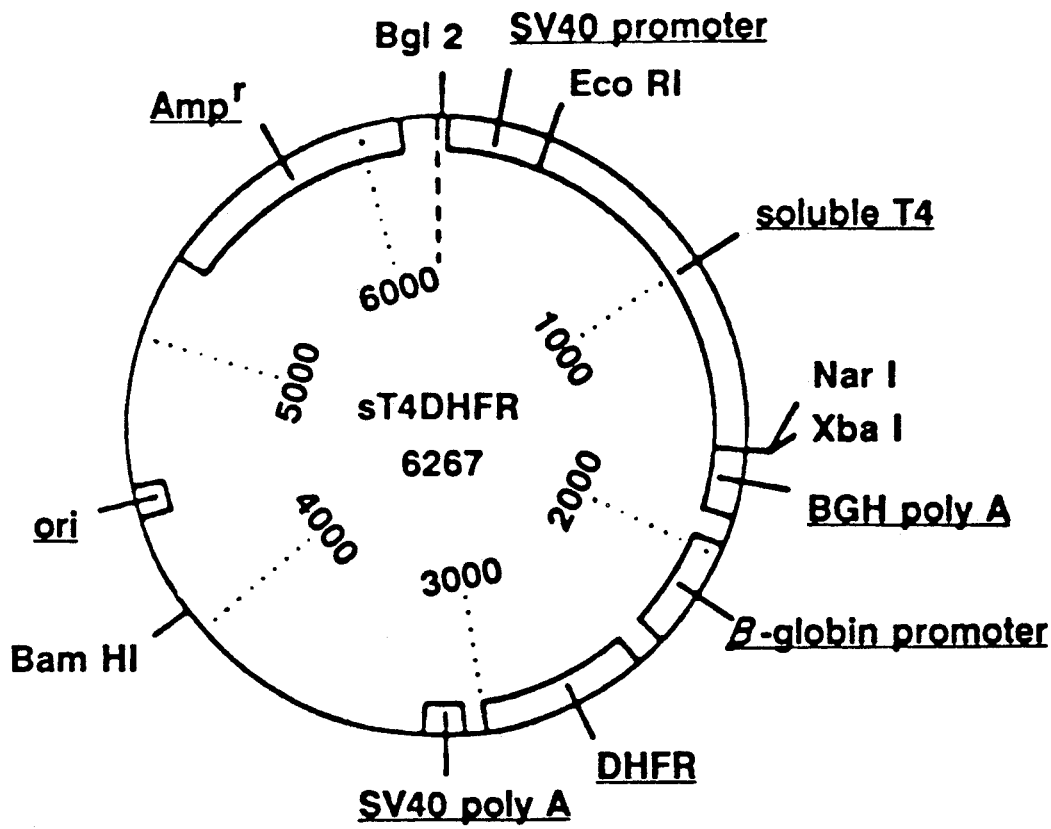

FIG. 16. Plasmid map of psT4DHFR

Plasmid psT4DHFR is a pUC18 derivative containing bp 1—1257 of the T4 cDNA clone pT4B which encodes the leader and extracellular segment of T4. This sT4 cDNA is inserted between an SV40 early promoter and a synthetic linker containing a TAA termination codon (inset) followed by the polyadenylation region of the bovine growth hormone gene. The sT4 expression cassette is linked to a mouse hdfr expression cassette consisting of the β-globin promoter, mouse dhfr coding sequence, and the SV40 polyadenylation region.

Figure 17:
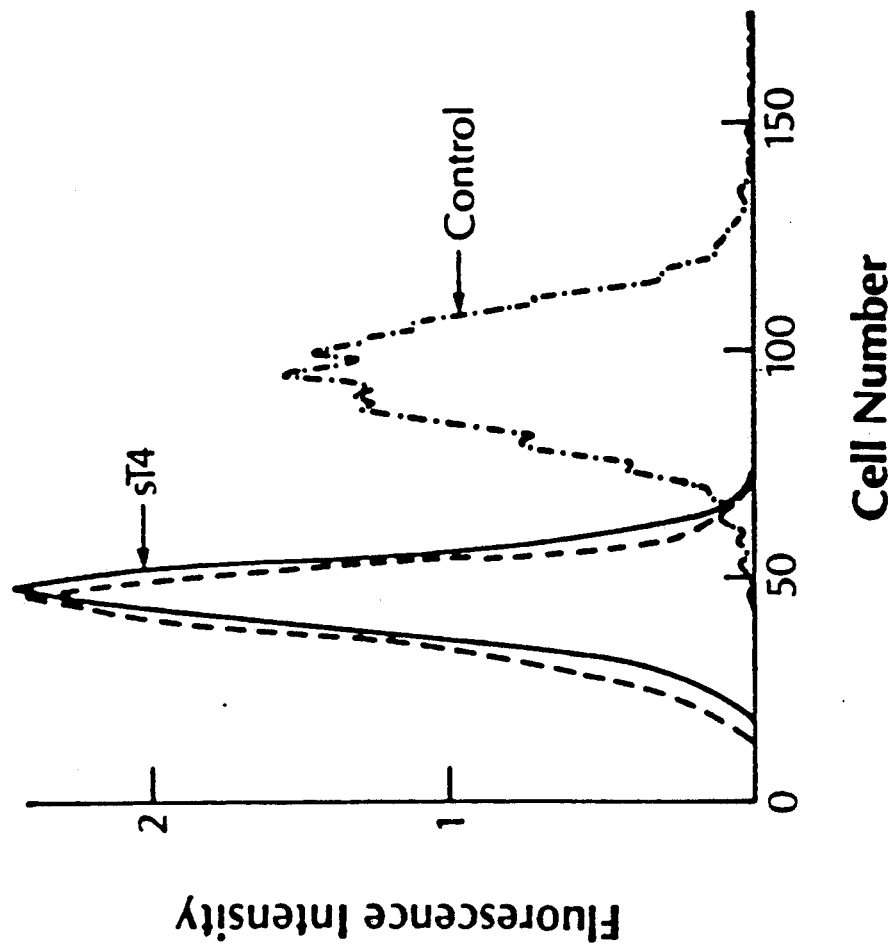

FIG. 17. Fluorescent histoqram (cell number vs. fluorescence inhutensitY)

sT4 inhibits HIV binding to T4+CEM cells. Cells were incubated with buffer ( ●—●—● ), HIV preincubated with sT4 (—), or with HIV preincubated with concentrated control supernatant from untransformed DXB-11 cells (———), washed, exposed to fluorescent-conjugated anti-HIV antibody, and analyzed by cytofluorometry. A fluorescent histogram (cell number vs. fluorescence intensity) is shown.

Figure 18A:
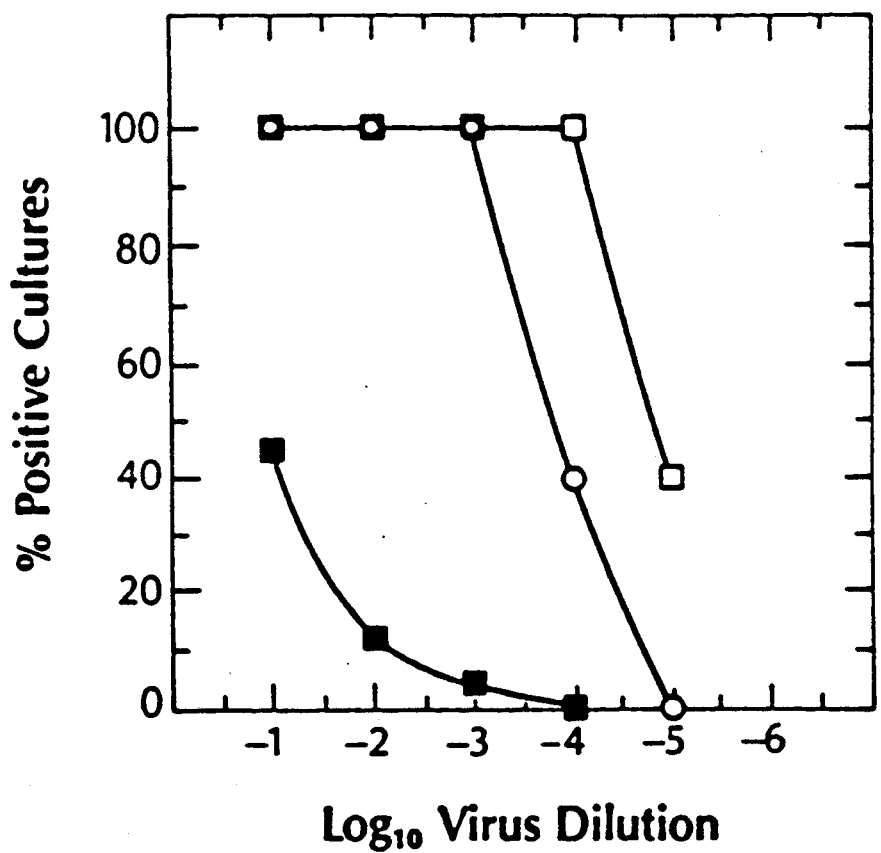
Figure 18B:
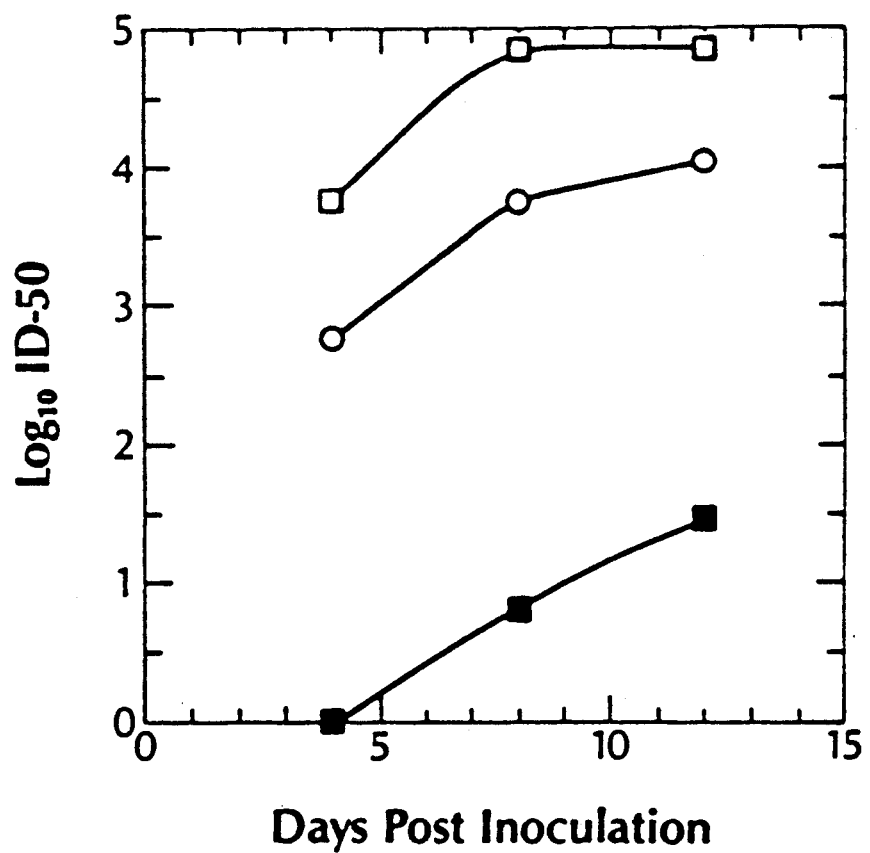
Figure 18C:
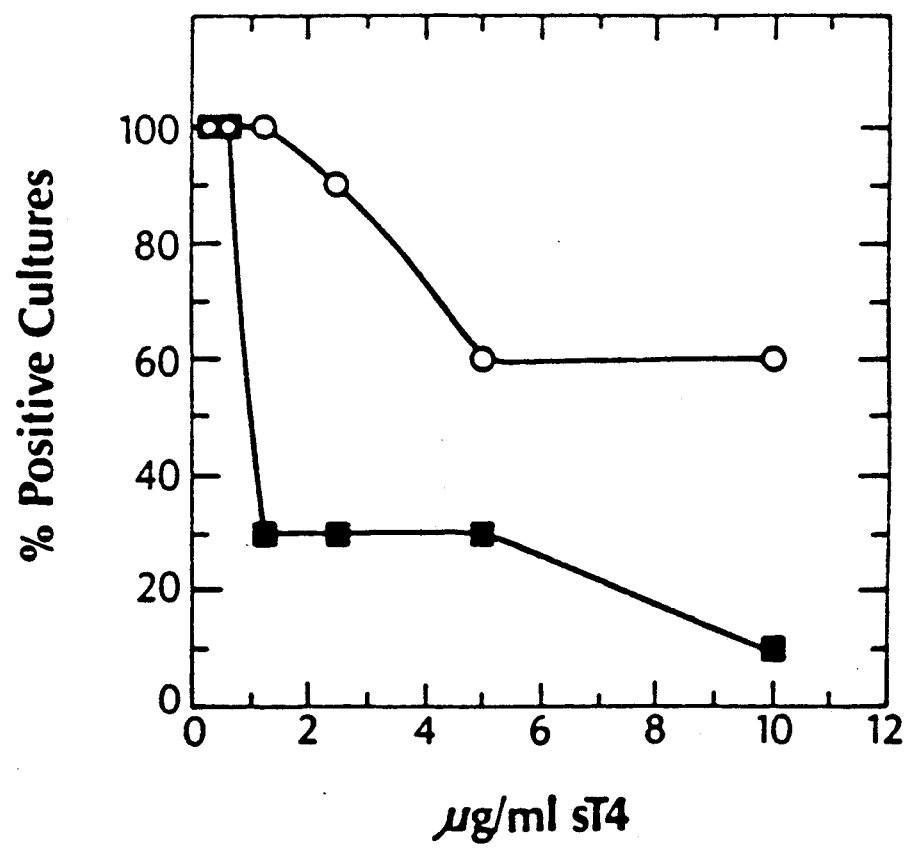

FIG. 18. Inhibition of HIV infectivity by sT4

Infectivity titration of an HIV inoculum (ID-50 assay) was performed. Serial 10-fold dilutions of virus inoculum are incubated with indicator cells (PHA-stimulated human lymphocytes) for 18 hrs. The cells are then washed and plated in microculture ($1 \times 10^5$ cells per culture, 10 cultures per dilution). At day 4, 8, and 12, supernatants are tested for HIV by the antigen capture assay. ID-50 titrations were performed in media containing 8.6 μg/ml sT4 which was added to the HIV dilution 30 minutes prior to inoculation of cells and maintained in the culture media throughout the experiment (■), or in media containing sT4 introduced after the initial 18 hr inoculum (○) (delayed addition control), or in media without sT4 (□)(control).

18A. Plot of percent of cultures positive for HIV at day 8 versus dilution of virus inoculum.

18B. Plot of ID-50 (reciprocal of virus dilution at which 50% of cultures are positive) at days 4, 8, and 12.

18C. Plot of percent of cultures positive for HIV at day 8 versus varying concentrations of sT4 using a 10−3 dilution of HIV.

DETAILED DESCRIPTION OF THE INVENTION

This invention provides a therapeutic agent capable of specifically forming a complex with human immunodeficiency virus envelope glycoprotein comprising a polypeptide In one embodiment of the invention, the amino acid sequence of the polypeptide comprises the amino acid sequence shown in FIG. 6 from about +1 to about +185 directly fused to the amino acid sequence from about 353 to about +371. In another embodiment of the invention, the amino acid sequence of the polypeptide comprises the amino acid sequence shown in FIG. 6 from about +1 to about +106 directly fused to the amino acid sequence from about +353 to about +371. In yet a further embodiment of the invention, the amino acid sequence of the polypeptide comprises the amino acid sequence shown in FIG. 6 from about +1 to about +185.

A pharmaceutical composition useful as a therapeutic agent for the treatment of a subject infected with a human immunodeficiency virus is also provided. This pharmaceutical composition comprises an amino acid sequence of the present invention which is capable of specifically forming a complex with a human immunodeficiency virus envelope glycoprotein and is soluble in an aqueous solution and a pharmaceutically acceptable carrier. Such pharmaceutically acceptable carriers are known in the art to which the present invention pertains and include, but are not limited to, 0.01-0.1M, preferably 0.05 M, phosphate buffer or 0.8% saline.

A method for treating a subject infected with a human immunodeficiency virus is also provided. This method comprises administering to the subject an effective amount of a pharmaceutical composition containing a pharmaceutically acceptable carrier and an amino acid sequence of the present invention, capable of specifically forming a complex with a human immunodeficiency virus envelope glycoprotein and soluble in an aqueous solution, so as to render human immunodeficiency viruses (also referred to herein as AIDS viruses) with which the subject is infected incapable of infecting T4+cells.

Characterization of the in vitro biological and immunological properties of the sT4 protein indicate the protein is of value in the prevention and treatment of AIDS. Studies indicate the sT4 protein acts as an inhibitor of extracellular and cell to cell spread of the virus. Because sT4 has been shown to block virus binding to T4+target cells in culture, it is believed administration of sT4 to infected persons would act to inhibit the extracellular spread of the virus. Therefore, sT4 is of value both as a prophylactic and therapeutic agent for treatment of AIDS.

As a prophylactic, sT4 is administered to individuals at high-risk for the disease or individuals who show exposure to HIV by the presence of antibodies to virus. Administration of an effective amount of sT4 at an early stage of the disease or prior to its onset acts to inhibit infection of T4+lymphocytes by HIV. As a therapeutic, administration of sT4 to persons infected with HIV acts to inhibit extracellular spread of the virus.

Fusion between HIV infected cells and other T4+lymphocytes also appears to be a route of virus spread. Further, fusion may be responsible, in part, for the impairment of T4+lymphocyte function and ultimately the depletion of T4+lymphocytes in infected individuals. Cell fusion is dependent on both viral envelope gene products and the T4 receptor and can be inhibited by the OKT4A, or similar monoclonal antibodies (Mabs) (120). sT4 interferes with cell fusion and therefore is expected to diminish the cell to cell spread of virus and the loss of T4+lymphocyte function.

The T4 receptor is monomorphic and thus sT4 is believed to be a universal inhibitor of virus which recognize the surface domain of the T4 receptor, including all HIV.

sT4 may be used in combination with other agents, for example, in association with agents directed against other HIV proteins, such as reverse transcriptase, protease or tat. An effective therapeutic agent against HIV should prevent virus mediated as well as cell to cell transmission of infection. sT4 may also be used in combination with other anti-viral agents, for example, azidothymidine (AZT).

The sT4 protein of this invention also has utility as an inhibitor of T4+cell function. Numerous studies suggest a critical role for the CD4 receptor (CD4 is general terminology for the human T4 receptor and its counterparts in other mammalian cells) in immune tolerance, particularly in the pathogenesis and progression of autoimmune diseases and in host specific graft rejection. Of particular relevance to sT4 are the observations with anti-CD4 Mabs. Through their association with the CD4 receptor, certain of these Mabs ameliorate autoimmune responses and graft rejection. Examples of such action include inhibition of T-cell function in vitro, for example, antigen induced proliferation, lymphokine secretion and helper cell function by certain anti-CD4 Mabs; treatment of systemic lupus erythematosus by administration of anti-CD4 Mabs to retard the onset of murine lupus; and grafting studies in mice wherein a single dose of murine Mab directed against the murine CD4 receptor results in acceptance of the allograft.

The molecular consequence of the binding of Mab to CD4 is unclear. The Mabs may block the association of CD4 with its ligand, which ligand, evidence suggests, is a conserved epitope on MHC class II antigens (121,122). However, at least some of these same Mabs inhibit CD4 cell activation by an apparent class II independent path.

sT4 is also believed to inhibit T-cell interactions as a competitor of cellular T4, perhaps by binding to extracellular target molecules which normally interact with the surface domain of the T4 receptor. This distinction between Mabs and sT4 could have important functional consequences. For example, whereas some Mabs directed against T4 elicit a response on the T4 cell, sT4 may elicit a response on cells expressing MHC class II antigens Also, the affinity of T4 for its presumed class II ligand appears to be quite low compared to the high affinities of Mabs directed against T4. Thus, although Mabs and sT4 may interfere with the same processes, they would affect different target molecules and different target cells.

As a prophylactic or therapeutic, sT4 is administered parenterally, preferably intravenously. The agent can be administered by infusion or by injection, e.g., daily, weekly or monthly. The amount and rate of sT4 administration is selected so as to maintain an effective amount of sT4 in circulation. An alternative mode of administration would be extracorporal, employing sT4 as a dialysis agent.

The sT4 protein of this invention can also be used as a reagent to identify natural, synthetic or recombinant molecules which act as therapeutic agents or inhibitors of T4+ cell interactions.

For example, sT4 protein can be used in screening assays, such as assays for protein interaction measured by ELISA based methodologies, to provide a biochemically pure, aqueous soluble reagent which may be used in combination with other reagents to assay for competitors of the T4 receptor surface domain interactions. For example, since sT4 binds to HIV env protein or mixtures containing HIV env proteins, it can be used to screen for inhibitors of virus binding. Based on in vitro data showing that sT4 binds to cells expressing HIV env proteins, sT4 can also serve as a selective targeting molecule for HIV infected cells in vivo. As a target specific carrier protein, sT4 can serve, for example, as the carrier protein for delivery of cytotoxic agents to the infected cells.

In addition, based on data showing that the T4 receptor specifically associates with MHC class II antigens on antigen-presenting cells as suggested by the class restriction of T4+ cells, sT4 can be used in combination with class II antigens to test for inhibitors of T4 lymphocyte - target cell interactions. In addition to these examples, which are based on direct binding assays between sT4 and its target molecules, more complex assays can be designed which rely on the biochemical responses to sT4 recognition.

Further provided is an expression vector encoding a polypeptide, the amino acid sequence of which comprises the amino acid sequence shown in FIG. 6 from about +1 to about +185 fused to the amino acid sequence from about +353 to about +371. In another embodiment of the invention, the expression vector encodes a polypeptide, the amino acid sequence of which comprises the amino acid sequence shown in FIG. 6 from about +1 to about +106 fused to the amino acid sequence from about +353 to about +371. In yet an additional embodiment of the invention, the expression vector encodes a polypeptide, the amino acid sequence of which comprises the amino acid sequence shown in FIG. 6 from about +1 to about +185.

A host cell comprising the expression vectors of this invention is also provided by the present invention. In one embodiment of the invention, the suitable host is a bacterial cell. In another embodiment of the invention, the bacterial cell is an *Escherichia coli* cell. In yet another embodiment of the invention, the suitable host is a eucaryotic cell. In a further embodiment of the invention, the eucaryotic cell is a mammalian cell. In yet a further embodiment of the invention, the eucaryotic cell is a yeast cell. In still another embodiment of the invention, the suitable host is an insect cell.

The present invention also provides a means for producing sT4 consisting of the predicted extracellular domain of the T4 receptor. Using that portion of the T4 cDNA which encodes the leader and extracellular domains of the T4 receptor, i.e., pre sT4, vectors are constructed capable of overexpression of sT4 in mammalian cells. The sequence of one sT4 is as follows:

```
        10          20          30          40          80          60
CAA GCC CAG AGC CCT GCG ATT TCT GTG GGC TCA GGT CCC TAC TGC TCA GCC CCT TCC TCC 70          80          90          100         110         120
CTC GGC AAG GCC ACA ATG AAC CGG GGA GTC CCT TTT AGG CAC TTG CTT CTG GTG CTG CAA
                        Met Asn Arg Gly Val Pro Phe Arg His Leu Leu Leu Val Leu Gln 130         140         150         160         170         180
CTG GCG CTC CTC CCA GCA GCC ACT CAG GGA AAG AAA GTG GTG CTG GGC AAA AAA GGG GAT
Leu Ala Leu Leu Pro Ala Ala Thr Gln Gly Lys Lys Val Val Leu Gly Lys Lys Gly Asp 190         200         210         220         230         240
ACA GTG GAA CTG ACC TGT ACA GCT TCC CAG AAG AAG AGC ATA CAA TTC CAC TGG AAA AAC
Thr Val Glu Leu Thr Cys Thr Ala Ser Gln Lys Lys Ser Ile Gln Phe His Trp Lys Asn 250         260         270         280         290         360
TCC AAC CAG ATA AAG ATT CTG GGA AAT CAG GGC TCC TCC TTA ACT AAA GGT CCA TCC AAC
Ser Asn Gln Ile Lys Ile Leu Gly Asn Gln Gly Ser Phe Leu Thr Lys Gly Pro Ser Lys 310         320         330         340         350         360
CTG AAT GAT CGC GCT GAC TCA AGA AGA AGC CTT TGG GAC CAA GGA AAC TTC CCC CTG ATC
Leu Asn Asp Arg Ala Asp Ser Arg Arg Ser Leu Trp Asp Gln Gly Asn Phe Pro Leu Ile
```

-continued

```
         370            380            390             400             410            420
ATC AGG AAT CTT AAG ATA GAA GAC TCA GAT ACT TAC ATC TGT GAA GTG GAG GAC CAG AAG
Ile Arg Asn Leu Lys Ile Glu Asp Ser Asp Thr Tyr Ile Cys Glu Val Glu Asp Gln Lys 430            440            450             460             470            480
GAG GAG GTG CAA TTG CTA GTG TTC GGA TTG ACT GCC AAC TCT GAC ACC CAC CTG CTT CAG
Glu Glu Val Gln Leu Leu Val Phe Gly Leu Thr Ala Asn Ser Asp Thr His Leu Leu Gln 490            500            510             520             530            540
GGG CAG AGC CTG ACC CTG ACC TTG GAG AGC CCC CCT GGT AGT AGC CCC TCA GTG CAA TGT
Gly Gln Ser Leu Thr Leu Thr Leu Glu Ser Pro Pro Gly Ser Ser Pro Ser Val Gln Cys 550            560            570             580             590            600
AGG AGT CCA AGG GGT AAA AAC ATA CAG GGG GGG AAG ACC CTC TCC GTG TCT CAG CTG GAG
Arg Ser Pro Arg Gly Lys Asn Ile Gln Gly Gly Lys Thr Leu Ser Val Ser Gln Leu Glu 610            620            630             640             650            660
CTC CAG GAT AGT GGC ACC TGG ACA TGC ACT GTC TTG CAG AAC CAG AAG AAG GTG GAG TTC
Leu Gln Asp Ser Gly Thr Trp Thr Cys Thr Val Leu Gln Asn Gln Lys Lys Val Glu Phe 670            680            690             710             720            730
AAA ATA GAC ATC GTG GTG CTA GCT TTC CAG AAG GCC TCC AGC ATA GTC TAT AAG AAA GAG
Lys Ile Asp Ile Val Val Leu Ala Phe Gln Lys Ala Ser Ser Ile Val Tyr Lys Lys Glu 730            740            750             760             770            780
GGG GAA CAG GTG GAC TTC TCC TTC CCA CTC GCC TTT ACA GTT GAA AAG CTG ACG GGC AGT
Gly Glu Gln Val Glu Phe Ser Phe Pro Leu Ala Phe Thr Val Glu Lys Leu Thr Gly Ser 790            800            820             820             830            840
GGC GAG CTG TGG TGG CAG GCG GAG AGG GCT TCC TCC TCC AAG TCT TGG ATC ACC TTT GAC
Gly Glu Leu Trp Trp Gln Ala Glu Arg Ala Ser Ser Ser Lys Ser Trp Ile Thr Phe Asp 850            860            870             880             890            900
CTG AAG AAC AAG GAA GTG TCT GTA AAA CGG GTT ACC CAG GAC CCT AAG CTC CAG ATG GGC
Leu Lys Asn Lys Glu Val Ser Val Lys Arg Val Thr Gln Asp Pro Lys Leu Gln Met Gly 910            920            930             940             950            960
AAG AAG CTC CCG CTC CAC CTC ACC CTG CCC CAG GCC TTG CCT CAG TAT GCT GGC TCT GGA
Lys Lys Leu Pro Leu His Leu Thr Leu Pro Gln Ala Leu Pro Gln Tyr Ala Gly Ser Gly 970            980            990             1000            1010           1020
AAC CTC ACC CTG GCC CTT GAA GCG AAA ACA GGA AAG TTG CAT CAG GAA GTG AAC CTG GTG
Asn Leu Thr Leu Ala Leu Glu Ala Lys Thr Gly Lys Leu His Gln Glu Val Asn Leu Val 1030           1040           1050            1060            1070           1080
GTG ATG AGA GCC ACT CAG CTC CAG AAA AAT TTG ACC TGT GAG GTG TGG GGA CCC ACC TCC
Val Met Arg Ala Thr Gln Leu Gln Lys Asn Leu Thr Cys Glu Val Trp Gly Pro Thr Ser 1090           1100           1110            1120            1130           1140
CCT AAG CTG ATG CTG AGC TTG AAA CTG GAG AAC AAG GAG GCA AAG GTC TCG AAG CGG GAG
Pro Lys Leu Met Leu Ser Leu Lys Leu Glu Asn Lys Glu Ala Lys Val Ser Lys Arg Glu 1150           1160           1170            1180            1190           1200
AAG GCG GTG TGG GTG CTG AAC CCT GAG GCG GGG ATG TGG CAG TGT CTG CTG AGT GAC TCG
Lys Ala Val Trp Val Leu Asn Pro Glu Ala Gly Met Trp Gln Cys Leu Leu Ser Asp Ser 1210           1220           1230            1240            1250           1260
GGA CAG GTC CTG CTG GAA TCC AAC ATC AAG GTT CTG CCC ACA TGG TCC ACC CCG GTG TAA
Gly Gln Val Leu Leu Glu Ser Asn Ile Lys Val Leu Pro Thr Trp Ser Thr Pro Val  ——

1270
TGG CGC CTC TAG A
```

The coding sequence for sT4 is obtained, for example, by synthesizing the gene using the known DNA sequence, by standard cloning techniques based on the sequence and by reisolation by detection of protein, i.e., transfection of cDNA clones from T4 expressing cell lines and identification by antibodies directed against the protein. cDNA clones carrying the sT4 coding sequence are identified by use of oligonucleotide hybridization probes. The probes are designed based on the known sequence of the T4 protein. Having identified a clone carrying the sT4 coding sequence, the coding sequence is excised by the use of restriction endonucleases and inserted into cloning and/or expression vectors. In an expression vector, the sT4 coding sequence is operatively linked to regulatory functions required or desirable for transcription, translation and processing of the coding sequence.

Regulatory functions include, for example, functions required for RNA polymerase binding and transcription, as well as other functions such as polyadenylation and enhancement of transcriptional sequences. The promoter can be regulatable so that, for example, expression is not induced until after transfection and selection of transformed clones. Promoters useful in the practice of the invention include, for example, the SV40 early promoter, and the long terminal repeats (LTR,s) of rous sarcoma virus, moloney sarcoma virus or cytomegalovirus (CMV).

Prior to transfection, the sT4 minigene, i.e., the gene encoding the leader and extracellular domains of the T4 receptor, preferably is incorporated into a larger DNA molecule which comprises a genetic selection marker system. The selection marker system consists of any gene or genes which cause a readily detectable phenotypic change in a transfected host cell. Such phenotypic change may be, for example, foci formation, drug resistance, such as genes for G418 or hygromycin B resistance; or other selectable markers such as xanthine guanine phosphoribosyl transferase (xgprt), thymidine kinase (TK) and galactokinase (galK). A selection marker which permits gene amplification can be employed to increase copy number, whether by increased transfection efficiency or by enhanced intracellular replication of the gene of interest and the selection marker. Such markers which also serve to amplify gene copy number include genes for dihydrofolate reductase (methotrexate resistance), CAD (N-phosphonacetyl-L-aspartate resistance) and adenosine deaminase (2-deoxycoformycin resistance).

Following transcription and translation in mammalian cells, the leader sequence appears to be cleaved and mature sT4 is secreted into the conditioned medium.

In the preferred practice of the invention, the sT4 minigene is linked with a human H-ras or a mouse dihydrofolate reductase (DHFR) minigene to create the expression vectors.

The sT4 minigene is linked, for example, with the human H-ras or mouse DHFR in order to provide a selection marker and means to selectively amplify gene expression through co-transfection with these genes. Common selection markers include, for example, DHFR, G418 or hygromycin which select for integration of as few as a single copy of the gene of interest. Amplification with, for example, methotrexate (mtx) in the DHFR system results in overexpression of the gene.

An alternate means of increased expression of the gene includes use of the ras proto-oncogene The ras gene family includes the H-ras, K-ras and N-ras genes. In a preferred application of the invention, the H-ras gene is used.

Other DNA functions can be linked directly or indirectly to the sT4 minigene or such functions may be unlinked. See, for example, Axel, U.S. Pat. No. 4,399,216.

Overexpression of gene products in mammalian cells can be achieved by transient or stable means. Transient overexpression can be achieved by viral methods such as the use of vaccinia virus vectors or by gene amplification methods such as with SV-40 based vectors in cells which support SV-40 replication. These methods ultimately lead to cell death. Stable overexpression can be achieved by generation of multiple gene copies such as through selection for gene amplification or through the use of the ras proto-oncogenes.

Overexpression of sT4 protein by co-transfection using the H-ras gene system can be achieved using a number of different cell lines, with the preferred cell line being the NIH-3T3 cell line which is a contact inhibited mouse fibroblast cell line. Other cell lines include the normal rat kidney (NRK) (ATCC 1571) cell line and the rat embryo fibroblast 52 (REF-52) cell line (115).

When using the selection marker system, for example, DHFR with methotrexate (DHFR/MTX technique), wherein amplification of gene copy number is achieved by selective amplification, the Chinese hamster ovary cell line (CHO) is preferred. In particular, CHO cells deficient in DHFR are used (116). Other cell types which may be used include, for example, any mammalian cell which has been modified so as to be DHFR+.

Some DHFR+ cell types may be used in combination with mutant DHFR genes which are less sensitive to methotrexate than normal DHFR (Axel, U.S. Pat. No. 4,399,216). In principle, DHFR+ cells may be used in combination with normal DHFR genes and an additional dominant selectable gene such as the gene for G418 resistance (117). Transfection is carried out using standard techniques (118, 119). These techniques include, for example, calcium phosphate precipitation, DEAEdextran induced pinocytosis, electroporation and viral transfection.

Following transfection, a cell which carries the sT4 minigene is cultured in a nutrient medium under conditions which permit amplification of the selectable gene. Standard mammalian cell culture medium can be employed, for example, F12 medium (GIBCO, Grand Island, NY) without hypoxanthine and thymidine and containing 10% fetal bovine serum. Cell cultures are maintained at ambient pressure at 30 to 45 C. Cells which survive selection and express high levels of sT4 protein are selected for further culturing. Such cells are cultured under selective conditions and the product, the sT4 protein, is collected and purified.

Cell culture methods which may be employed in the practice of the invention include, for example, use of adherent cells or growth of cells in a suspension. Conditioned medium (CM) can be collected from cells grown in suspension or adhered to solid supports, i.e., CM is prepared from adherent cells grown in roller bottles or grown on solid supports and cultured in suspension or in fluidized or packed beds. CM is prepared from suspension cells in stirred-tank vessels.

The sT4 of the invention includes derivatives of the extracellular domain of T4. Such derivatives comprise addition, deletions or subsitutions which alterations do not significantly adversely affect secretion of the protein into the conditioned medium and the affinity of the protein for HIV env protein, i.e , gp120. For example, one or a few amino acids can be added to or deleted from the N- or C- terminus. Or, one or a few amino acids, preferably no more than four amino acids can be inserted into, deleted or substituted for internal amino acids. Alternatively, a hybrid protein, i.e., a translational fusion, can be constructed between sT4 and a protein carrier, another antigen or other sT4 molecules to prepare a poly-sT4 molecule. In yet another alternative, sT4 can be synthetically conjugated to a carrier molecule.

One embodiment of a sT4 derivative is illustrated in the Examples below (see Example 3). Affinity of the sT4 for HIV env can be demonstrated by a competitive binding assay using a sT4 molecule having a known affinity or using antibodies which recognize the T4 receptor, such as OKT4 and OKT4A. Useful derivative sT4 molecules of the invention are selectively precipitated from conditioned medium by OKT4A as shown in Example 3. Derivatives can be prepared chemically, after expression, or genetically, prior to expression, by manipulation of the coding sequence for the leader and/or extracellular domain.

The sT4 of the invention can be purified from the spent culture media using various protein purification techniques, for example, affinity chromatography; ion exchange chromatography; size exclusion chromatography; hydrophobic chromatography or reversed phase chromatography.

sT4 can be purified by affinity chromatography using general group-specific adsorbants, for example, carbohydrate binding or dye affinity ligands; or using ligands that specifically bind to sT4, for example, monoclonal antibody or HIV gpl20 protein or portions thereof.

An exemplary purification scheme comprises: (1) growing cells in a serum-free selection growth media; (2) clarification of the conditioned media; and (3) separation of sT4 of the invention from other proteins present in the conditioned media.

In the preferred method, the sT4 is purified from the serum-free culture medium using a series of chromatography steps which are based on the physical properties of the sT4 molecule The sT4 may also be purified from culture medium containing serum using similar chromatography methods.

In the preferred method of purification of sT4, the culture medium is first passed through an ion exchange column, preferably an S-Sepharose ®(Sulpho-propyl Sepharose) column, which binds the sT4 while the majority of contaminating proteins flow through the column. The protein sample is then eluted using a linear salt gradient. A second ion exchange column is used. This column, preferably a Q-Separose ®(quarternary amino ethyl Sepharose) column has properties such that the contaminating proteins present in the sample are bound to the column while the sT4 does not bind and is recovered in the column flow-through buffer. Finally, a gel filtration column is used which acts to remove remaining contaminating materials. An alternative method of purification of sT4 involves the use of monoclonal antibodies directed against sT4 The sT4 protein can be purified in one step by passage of clarified culture media through an affinity gel support to which monoclonal antibody directed against sT4 is bound. The sT4 will bind to the column at the antibody binding site while all contaminating proteins wash through the column. The sT4 is then eluted from the column under conditions that prevent sT4 protein from being inactivated. Further provided is a method of producing any one of the above described therapeutic agents capable of specifically forming a complex with human immuno eficiency virus envelope glycoprotein which comprises growing the host vector system of the invention under suitable conditions permitting production of the therapeutic agent and recovering the therapeutic agent so produced The sT4 can be used in diagnostic assays for the detection of T4 proteins or the molecules with which they interact. For example, quantitation of T4 and T4+cells and antibodies to T4 would be of diagnostic value for AIDS.

In addition, sT4 can be used to generate new diagnostic reagents, for example, Mabs or other types of molecules for use in the standard immunologic assays, i.e., ELISA, capture immunoassays, radioimmune assays. Because sT4 displays the OKT4, the OKT4A and most if not all of the other surface epitopes of the T4 receptor, sT4 is especially useful in immunodiagnostic assays as it can be used for absolute quantitation of T4 levels in a system. Currently there are no standards for quantitating the T4 receptor.

The T4 receptor resides in three diverse chemical environments: the oxidizing, hydrophilic cell surface; the hydrophobic membrane; and the reducing, hydrophilic cytoplasm. These diverse environments would most likely preclude the isolation of the receptor in its fully native state. sT4, which consists of only the extracellular domain, is secreted as a soluble protein into the cell supernatant and its conformation appears to mimic the surface of the receptor surface domain. Thus, sT4 is suitable for detailed structural analysis, in particular for x-ray crystallography. Determination of the three-dimensional structure of sT4 alone or in a complexed form with other interactive molecules could provide a basis for the rational design of selective antagonists and agonists for sT4.

The various prophylaxis and immunization methods for AIDS provided by the present invention are based upon the abilities of the novel peptides, antibodies, and DNA molecules disclosed herein to form complexes with, or hybridize to, specific molecules and to invoke an immunological response effective for neutralizing the AIDS virus. These molecules, methods for their preparation, and methods of AIDS treatment will be better understood by reference to the following experiments and examples which are provided for purposes of illustration and are not to be construed as in any way limiting the scope of the present invention, which is defined by the claims appended hereto.

Materials and Methods

Cells and Antibodies

Peripheral blood leukocytes isolated by Ficoll-Hypaque density gradient centrifugation were fractionated into sheep erythrocyte rosette-positive (E+) cells. T4+ and T8+ subsets within the E+ population were isolated by positive selection of T8−bearing cells with anti-T8 antibody and human erythrocytes conjugated with affinity-purified rabbit anti-mouse IgG (10). Cytofluorometric analysis of these subsets demonstrated that the T4+ cells were 95% T4+ and 2% T8+, whereas the T8+ cells W®re 95% T8+ and 2% T4+.

The Fro 2.2 T cell line (T3−, T4+, T8+, T11+) was derived from an adult patient with undifferentiated acute leukemia. Jurkatt is T3−, T4+, T8+, T11−, RPMI 8402 is T3−, T4−, T8 , T11 +TO-CLL is a chronic lymphocytic leukemia which is T3+, T4+, T8− and T11+(22). The T4+cell lines CEM and Molt 4 were obtained from the American Type Culture Collection. All leukemic T cell lines were continuously grown in RPMI 1640 medium containing 5% fetal calf serum. Transformed B cell lines CB, CP58 and CP94 were derived as previously described (23).

Affinity-purified rabbit anti-mouse IgG was conjugated to human erythrocytes by the chromium chloride method (24).

Cotransformation of L Cells and NIH 3T3 Cells

Murine L tk−aprt−cells were maintained in Dulbecco,s modified Eagle's medium (DME) supplemented with 10% calf serum (Gibco) and 50 micrograms/ml diaminopurine (DAP). L cells were plated out at a density of $5 \times 10^4$ cells per 10 cm dish, 1 day before transformation. Calcium phosphate precipitates were prepared by the method of Graham and van der Eb (25), as modified by Wigler et al. (26), using 100 ng of pTK and 20 micrograms of high molecular weight T cell or L cell DNA per dish. The L cells were placed under selection in DME with 10% calf serum, 15 micrograms/ml hypoxanthine, 1 microgram/ml aminopterin and 5 micrograms/ml thymidine (HAT medium (27)) on the following day. After 12-14 days of HAT selection, tk+ transformants were screened using the rosetting assay.

Murine NIH 3T3 cells were maintained in DME supplemented with 10% newborn calf serum (Gibco). NIH 3T3 cells were plated out at a density of $5 \times 10^4$ cells per 10 cm dish, 2 days before transformation. A calcium phosphate precipitate was applied to the cells using 10 micrograms of carrier DNA and either 10 micrograms of T4−pMV6tk/neo or 10 micrograms of T4−pVcos7 and 500 ng of pSV2neo. After 2 days, the cells were placed under selection in DME with 10% calf serum and 500 micrograms/ml G418 (Geneticin ®; Gibco). Rosetting assays were performed on surviving colonies one week after growth in selective medium.

Rosetting Assay

After one rinse with phosphate-buffered saline (PBS), the plates were incubated with 2.5 ml of the purified monoclonal antibody OKT®4A (1 mg/ml) diluted at 1/500 in PBS containing 5% fetal calf serum for 45 minutes at room temperature. Free antibody was removed from the plates with three gentle rinses in PBS. Six milliliters of human erythrocytes conjugated with purified rabbit anti-mouse IgG antibody (2% v/v stock suspension, diluted 1/10 in PBS/5% fetal calf serum) were added and the plates were left at room temperature. After 45 minutes, free erythrocytes were gently aspirated and PBS was added prior to inspection for rosette-positive colonies.

Cytofluorometric Analysis

Adherent cells were removed with 0.005 M EDTA in PBS and washed once with PBS containing 1% bovine serum albumin (BSA) and 0.01% sodium azide (cytowash). Cells ($5 \times 10^6$) in 0.1 ml were added to tubes with appropriate dilutions of OKT®4, OKT®8 or control antibodies. The cell-antibody mixture was incubated for 45 minutes at 4° C. and then washed twice in cytowash. Fluorescein isothiocyanate (FITC)- conjugated goat anti-mouse IgG +IgA +IgM (Cappel) was added to the cells and incubated for 1 hour at 4° C. The cells were then washed three times in cytowash and resuspended in 0.5 ml of PBS with 0.01% sodium azide. The cells were analyzed on a Becton Dickinson FACS IV Cell Sorter and the data was stored and plotted using a VAX 11/780 computer (Digital Equipment Co.)

RNA and DNA Isolation

Total RNA was isolated from cells by homogenation in 4 M guanidinium thiocyanate, followed by ultracentrifugation through a 5.7 M CsCl cushion (28). Poly-(A)+ selection was achieved by oligo(dT)-cellulose chromatography (Type 3, Collaborative Research) (29). High molecular weight genomic DNA was prepared as described by Wigler et al. (26).

cDNA and Genomic Libraries

Double-stranded cDNA was synthesized from poly-(A)+RNA derived from peripheral human T cells (20). After treatment with EcoRI methylase and T4 DNA polymerase, the double-stranded cDNA was cloned into the EcoRI site of λgt10 (30) using EcoRI linkers. The Charon 4 human genomic library was generously provided by Dr. Tom Maniatis (Harvard University) (31).

Synthesis of a Subtracted cDNA Probe $^{32}$P-labeled cDNA was synthesized from poly(A)+ RNA derived from the primary transformant, LTD-4, as described by Davis et al. (32). After annealing the cDNA to an excess of untransformed L cell poly(A)+ RNA (Rot =3000), single-stranded sequences, which were enriched for human cDNAs, were isolated by hydroxyapatite chromatography (32). Prior to filter hybridization, the subtracted cDNA probe was concentrated with sec-butanol and desalted on a G-50 Sephadex column equilibrated in TE.

Screening of cDNA and Genomic Libraries

The peripheral human T cell library was plated on *E. coli* C600/HFL and the human genomic library was plated on *E. coli* LE392. Screening of duplicate filters was carried out according to the standard procedure (33), with the hybridization performed in 50% formamide and $5 \times SSC$ at 42° C. In the screen of the cDNA library, $6 \times 10^4$ cpm of subtracted probe was applied per 137 mm nitrocellulose filter Filters from the genomic library were hybridized to a nick-translated (34) cDNA insert. The washes were performed at 68° C., with a final wash in 0.2 x SSC. Autoradiography was performed at −70° C. in the presence of intensifying screens for 1-2 days.

DNA Sequencing

Restriction fragments of pT4B were subcloned into the M13 vectors mp18 and mp19 (35). Sequencing reactions were performed using the dideoxy chain termination technique (36). The sequencing strategy is depicted in FIG. 3B.

Southern and Northern Blot Hybridizations

High molecular weight cellular DNAs were digested with 5 units of restriction nuclease per microgram of DNA according to the manufacturer's recommendation (Boehringer Mannheim). Samples (10 micrograms) were subjected to electrophoresis on a 0.8% agarose gel. DNA fragments were transferred to GeneScreen (New England Nuclear; (37)) and hybridized as described by Church and Gilbert (38).

RNA was run on a 0.8% agarose-formaldehyde gel (39) and transferred to GeneScreen. Northern hybridization was performed according to the procedures supplied by the manufacturer. Both Southern and Northern blots were hybridized to nick-translated probes Synthesis and In Vitro Translation of SP6 RNA The 3 kb T4 cDNA was subcloned into the EcoRI site of pSP65 (Promega Biotec) and linearized with HindIII. Transcription of linearized plasmid DNA (1 microgram) with SP6 polymerase in the absence of radiolabeled nucleotides was performed as described (40), except that GpppG and unlabeled CTP were added to the transcription buffer. One-tenth of the reaction mixture was translated in a wheat germ system (Bethesda Research Laboratories) containing L-[$^{32}$S]-methionine (Amersham) and 1 micromolar S-adenosyl-methionine. The in vitro translation products were subjected to SDSpolyacrylamide electrophoresis under reducing conditions as described below.

Cell Labeling, Lectin Chromatography and Immunoprecipitation

Cells were grown for 12 hours in methionine-free DME medium containing 10% dialyzed calf serum and 1 mCi of L-[$^{32}$S]-methionine (Amersham) as previously described (41). The cells were solubilized in 10 mM Tris (pH 7.4), 150 mM NaCl (TBS) containing 0.5% Nonidet P-40 (Shell) and 0.2 mM phenylmethylsulfonyl fluoride (Sigma). The lysates were centrifuged for 1 hour at 100,000 ×g, and the supernatants were subjected to lentil lectin chromatography (Pharmacia) according to the procedures of Hedo et al. (42). Eluates were preabsorbed once with a mixture of control mouse ascites and protein A-Sepharose (Pharmacia) for 1 hour at 4° C. and twice with protein A-Sepharose alone for 1 hour at 4° C. Of each supernatant, $2.5 \times 10^4$ cpm were then mixed with 10 microliters monoclonal antibody (approximately 1 mg/ml) and protein A-Sepharose and incubated on a turntable overnight at 4.C. The beads were then washed four times with cold TBS containing 0.5% NP-40 and 0.2% SDS and were resuspended in electrophoresis sample buffer.

Gel Electrophoresis

SDS-polyacrylamide gel electrophoresis was performed according to the procedure of Laemmli (43). The immunoprecipitates and in vitro translation products were dissolved in sample buffer with or without 2$^-$mercaptoethanol and then were applied to 10% poly-acrylamide gels. Autoradiography was performed on Kodak XAR-5 film in the presence of intensifying screens (DuPont Chemical Company).

Cotransformation and Rosetting Assay

Mouse $\psi$-2 cells (44) were maintained in Dulbecco,s modified Eagle,s medium (DME) supplemented with 10% calf serum (CS) (Gibco). $\psi$-2 cells were plated out at a density of $5 \times 10^5$ cells per 10 cm dish, 2 days before transformation Calcium phosphate precipitates were prepared by the method of Graham and van der Eb (25), as modified by Wigler et al. (27). Precipitates were applied to the cells using 10 micrograms of carrier DNA and either 10 micrograms of T4$^-$pMV7 or 10 micrograms of T8$^-$pMV7. After 2 days, the cells were placed under selection in DME/10% CS and 500 micrograms/ml G418 (Geneticin ®; Gibco).

Rosetting assays to identify T4$^+$ or T8$^+$ colonies were performed on surviving colonies 1 week after growth in selective medium. After one rinse with phosphate-buffered saline (PBS), the plates were incubated with 2.5 ml of the purified monoclonal antibody OKT ®4A or OKT ®8 (lmg/ml; Ortho) diluted at 1/500 in PBS containing 5% fetal calf serum (FCS) for 45 minutes at room temperature. Free antibody was removed from the plates with three gentle rinses in PBS. 6 ml of human erythrocytes conjugated with purified rabbit anti-mouse IgG antibody (2% v/v stock suspension, diluted 1/10 in PBS/5% FCS) were added and the plates were left at room temperature. After 45 minutes, free erythrocytes were gently aspirated and PBS was added prior to inspection. T4$^+$ and T8$^+\psi$-2 clones were purified by colony isolation and characterized by flow cytometry and Northern blot analysis.

Recombinant Retrovirus Production and Infection

T4$^+$ and T8$^+\psi$-2 clones were isolated which produce recombinant retrovirus stocks with titers of 105 cfu/ml. Viral stocks were prepared by adding 10 ml of fresh. DME/10% CS to a near confluent monolayer of the T4$^+$ or T8$^+\psi$-2 clones. After 24 hours, the medium was removed and filtered through a 0.45 micrometer filter (Millipore). For infection, $5 \times 10^5$ cells were incubated with 2 ml of viral supernatant (or a dilution) in the presence of 8 micrograms/ml polybrene (Aldrich). After 3 hours, 8 ml of fresh medium was added. 3 days after infection the cells were reseeded into DME/10% CS containing 500 micrograms/ml G418, grown for 2 weeks, scored for G418$^r$ colonies, and screened for surface T4 or T8 expression using the in situ rosetting procedure or flow cytometry.

$\psi$2 culture supernatants were used to infect mouse $\psi$-AM cells as described above. T4$^+$ or T8$^+$adherent transformants were purified by the in situ rosetting assay followed by colony isolation; T4$^+$ or T8$^+$non-adherent transformants were purified by fluorescence-activated cell sorting (FACS). Non-adherent human lymphoid cell lines (HSB2, RPMI-T cells; Raji - B cells) and adherent epithelial cells (HeLa) were infected by co-cultivation with T4$^+$ or T8$^+\psi$-AM clones (pretreated with 10 micrograms/ml mitomycin-C for 2 hours; Sigma) and were purified.

Cell lines were selected for G418 resistance at a concentration of 1.5 mg/ml, except for HeLa cells which require 1 mg/ml, and fibroblasts which require 0.5 mg/ml. All cell cultures producing recombinant amphotrophic viruses (4-AM) were maintained under P3 containment conditions.

AIDS Virus

The prototype LAV strain of HTLV-III/LAV was obtained from J.-C. Cherman (Institut Pastuer, Paris; (45)). Virus inocula used in these studies were from the second to fifth passages of virus in our laboratory. Inocula are culture supernatants from HTLV-III/LAVinfected, phytohemagglutinin (PHA)-stimulated peripheral lymphocytes which were harvested by sequential centrifugation (300×g for 7 minutes followed by 1500×g for 20 minutes), and were stored in liquid nitrogen. For binding studies, virus was concentrated from culture supernatants, harvested as above, by ultracentrifugation at 90,000×g for 90 minutes over a 15% cushion of Renograffin (E.R. Squibb) in 0.01 M Tris, 0.15 M NaCl, 1 mM EDTA, pH 8.0.

Anti-HTLV-III/LAV Reagents

Serum with high levels of antibody to HTLV-III/-LAV was obtained from a homosexual man with chronic lymphadenopathy, and its specificity by immunofluorescence (46), Western blot analysis (47), and radioimmunoprecipitation (48) has been described. Portions of the IgG fraction were coupled with fluorescein isothiocyanate (FITC; FITC:protein ratio of 10.7 micrograms/ml), horseradish peroxidase (HPO; type VI; Sigma) and agarose as described (47, 49, 50, 51). Conjugates of IgG from a nonimmune serum were prepared in parallel.

Reverse Transcriptase Assay

Magnesium-dependent, particulate reverse transcriptase (RT) activity was measured with a template primer of $(A)_n(dT)12$-18 (or $(dA)_n(dT)12$-18 2as the negative control) in the presence of 7.5 mM Mg (52).

Immunofluorescence Detection of Cytoplasmic AIDS Virus

Cultured cells ($1 \times 10^5$ in 0.1 ml) were centrifuged onto glass slides (Shandon Cytocentrifuge), fixed in 5% ethanol and 5% acetic acid at −20° C. for 30 minutes, and rehydrated with three 10 minute changes of PBS (0.01 M PO₄, 0.15 M NaCl, pH 8.0). Slides were exposed to a 1/500 dilution of FITC-anti-HTLV-III/-LAV (19 micrograms/ml) for 30 minutes at room temperature. The slides were then washed (three changes, 10 minutes each) and mounted under a coverslip with 50% glycerol in PBS. The slides were examined with an epi-illuminated Leitz Orthoplan microscope at 630 × power. Under these conditions, the FITC-anti-HTLV-III/LAV reagent is specific for HTLV-III/LAV. Uninfected PHA-stimulated cells, Epstein Barr (EB) virus-infected B cell lines, an adenovirus-infected cell line, several T cell lines, and HTLV-I and HTLV-II infected cell lines were not stained.

AIDS Virus Immunoassay (Antigen Capture Assay)

This is a sandwich immunoassay that has been described in detail (47). Briefly, culture supernatant is added to microtiter plate wells coated with anti-HTLV-III/LAV IgG. After the plates are washed, bound virus antigen is detected with HPO-anti-HTLV-III/LAV. This assay, which is at least as sensitive as the RT assay, is negative with culture supernatants from PHA-stimulated lymphocytes from numerous donors, EB virus-infected B cell lines, several T cell lines, polyclonal and cloned IL-2 dependent T cell lines, the myeloid line K562, as well as cell lines that harbor HTLV-I or HTLV-II. The cutoff $OD_{490}$ for discriminating a positive from a negative supernatant was determined in each run from the mean plus 2 SD of at least 10 replicative determinations on control (uninfected cell culture) supernatants harvested at the same time.

AIDS Virus Infectivity (ID-50) Assay

The microculture assay for the titration of infectious HTLV-III/LAV has been described in detail (47). Briefly, PHA-stimulated lymphocytes or cell lines ($2 \times 10^6$ cells/ml) are inoculated with serial 10-fold dilutions of virus inoculum and incubated for 18 hours at 37° C. The cells were then washed and plated in microculture (10 to 20 cultures per dilution: $1 \times 10^5$ cells per culture in 0.25 ml medium). Every 4 days, 100 microliters of supernatant was removed and replaced with fresh medium. Supernatants were then assayed for viral antigen by the antigen capture assay as described above. Infectious virus titer (ID-50) is defined as the reciprocal of the dilution at which 50% of the cultures are positive for virus (47).

VSV Pseudotype Assay

Vesicular stomatitis virus (VSV, Indiana strain, wild type) was propagated in cells producing the retrovirus required for the envelope pseudotype as described (53). Hyperimmune neutralizing sheep anti-VSV serum was added to the harvested VSV to inactivate non-pseudotype virions. The pseudotype titers ranged between $10^4$ and $10^5$ PFU/ml For the assay, $2 \times 10^5$ cells to be infected with VSV pseudotypes were plated in 30 mm diameter tissue culture wells. HeLa, NIH 3T3, and L cells were naturally adherent; all other cells types were attached by pretreatment of the substratum with 50 micrograms/ml poly-L-lysine. After virus adsorption for 1 hour, the cells were washed and $10^6$ mink CCL64 or bovine MDBK cells were added to each well. These cells provide excellent plaques for secondary VSV infection but are resistant to infection by pseudotype virions. After allowing the plaque indicator cells to settle and spread (approximately 90 minutes), the monolayers were overlaid with agar medium. VSV plaques were counted 2 days after infection. Anti-T4A monoclonal antibody (1:20), anti-HTLV-III serum (1:10), or anti-HTLV-I serum (1:10) were used to inhibit pseudotype plaque formation by pretreatment of cells 30 minutes before addition of pseudotypes as described by (54).

Syncytium Induction Assay $2 \times 10^5$ cells were co-cultivated with $2 \times 10^4$ H9 cells infected by and producing HTLV-III (55) in 10 mm diameter wells. The cultures were incubated at 37° C. and examined for syncytia formation after 18 hours as previously described (54, 56). Cells with five or more syncytia were scored as positive. Syncytium inhibition was assayed by adding anti-T4A monoclonal antibody (1:20) to the mixed cultures at the time of seeding.

Cytofluorometric Analysis and AIDS Virus Binding

The method has been described in detail (46). Briefly, cell surface T4 or T8 expression was detected by direct immunofluorescence with fluorescein-conjugated anti-T4A or anti-T8 monoclonal antibodies (OKT®4A, OKT®8). The diluent/wash buffer was 0.01 M PO₄, 0.15 M NaCl, pH 7.4, containing 0.1% bovine serum albumin, 2% v/v AB+human serum, and 0.01% $NaN_3$ All reagents were pretitered for optimal (saturating) binding. Cells ($5 \times 10^5$) were incubated in a 25 microliter dilution of monoclonal antibody for 30 minutes at 4° C. The cells were washed by centrifugation (300 ×g for 7 minutes), resuspended in 0.5 ml of 1% paraformaldehyde in saline, and analyzed with a fluorescence-activated cell sorter (FACS IV, Becton Dickinson). For HTLV-III/LAV binding, $5 \times 10^5$ cells were incubated with HTLV-III/LAV (500 ng in 10 microliters) for 30 minutes at 37.C. Washed cells were resuspended in 25 microliters of fluoresce- in-conjugated anti-HTLV-III/-LAV for 30 minutes at 4° C. The cells were washed, resuspended in 1% paraformaldehyde, and analyzed by FACS as above. For inhibition of HTLV-III/LAV binding, cells were preincubated with anti-T4A or anti-T8 (20 ng in 20 microliters) for 30 minutes at 4° C. followed by addition of HTLV-III/LAV (500 ng in 10 microliters) for 30 minutes at 37.C. The cells were washed incubated with fluorescein-conjugated anti-HTLV-III/LAV, washed, resuspended in paraformaldehyde, and analyzed by FACS as above.

Cell Surface Radioiodination, Immunoprecipitation, and Gel Electrophoresis

T4+NIH 3T3 transformants were surface radioiodinated by the lactoperoxidase technique (18) as follows: $4 \times 10^7$ cells were suspended in 1 ml of PBS containing 0.5 mM EDTA, 2 mCi Na125I, and 20 micrograms lactoperoxidase. At times 0, 1, 5, 10, and 15 minutes, 10 microliters of 0.03% $H_2O^2$ were added. The reaction was carried out at 23° C. and was stopped at 20 minutes by 2 centrifugations in 50 volumes of cold PBS containing 10 mM NaI. Labeled cells were split into 4 tubes and incubated, as indicated, with HTLV-III/LAV (2 micrograms in 20 microliters) for 30 minutes at 37° C. Subsequent washes and manipulations were performed at 0. to 4° C. Washed cells were lysed by adding 1 ml of detergent lysing buffer (LB; 0.02 M Tris, 0.12 M NaCl, pH 8.0, containing 0.2 mM phenylethlsulfonylfluoride, 5 micrograms/ml aprotinin, 0.2 mM EGTA, 0.2 mM NaF, 0.2% sodium deoxycholate, and 0.5% (v/v) Nonidet P-40). Tubes were held on ice for 15 minutes, and nuclei were removed by centifugation at 3000 ×g for 20 minutes.

For absorptions, Sepharose conjugates of human anti-HTLV-III/LAV IgG, human nonimmune IgG, anti-T4A, and anti-T8 antibodies were prepared as described (48). Lysates were preabsorbed with 200 microliters of Sepha-rose-nonimmune human IgG for 1.5 hours with rotation, and then immunoprecipitated with 20 microliters of Sepharose conjugates (as indicated) for 3 hours with rotation. Sepharose absorbants were washed 3 times: once with LB; once with LB containing 0.5 M NaCl; and once with LB containing 0.1% sodium dodecyl sulfate (SDS). Absorbed material was eluted at 65° C. for 30 minutes with 20 microliters of sample buffer (0.01 M Tris, pH 8.0, containing 2% SDS, 5% 2-mercapto-ethanol (v/v), 25 micrograms bromphenol blue, and 10% glycerol (v/v). Electrophoresis was performed in a 3.3-20% gradient polyacrylamide gel with a 3% stacking gel (57), and autoradiographs were developed with Kodak XAR-5 film.

Virus Inhibition Assay $2 \times 10^5$ T4+JM T cells were exposed to AIDS virus at 0 minutes. The inhibitors ammonium chloride (20 mM) or amantadine (20 mM) were added at various times during the course of virus infection (0 minutes, 30 minutes, and 60 minutes). After 6 hours, cells were washed and replated in fresh medium (RPMI/10%FCS). The effect of these agents on AIDS virus infection was determined 5 days post infection. The fraction of infected cells in the cultures expressing viral antigens was determined by immunofluorescence microscopy as described above (58).

RNA Isolation and Northern Blot Hybridizations

Total RNA was isolated from cells by homogenation in 4M guanidinium thiocyanate, followed by ultracentrifugation through a 5.7 M CsCl cushion (28). Poly-(A)+selection was achieved by oligo(dT)-cellulose chromatography (Type 3, Collaborative Research) (29).

RNA was electrophoresed through a 1% agarose-formaldehyde gel (39) and transferred onto Hybond (Amersham). Northern blot hybridization was performed according to the procedures supplied by the manufacturer. Probes were nick-translated to a specific activity of $0.5-1 \times 10^9$ cpm/microgram with $\alpha 32P$-labeled deoxynucleotide triphosphates (59).

RESULTS

Isolation of a T4 cDNA

The strategy used to isolate a T4 cDNA initially involved constructing L cell transformants that express T4 on their surface. cDNA synthesized from the mRNA of a T4+transformed fibroblast was enriched by substractive hybridization and used as a probe to isolate a cDNA encoding T4 from a cDNA library made from the mRNA of peripheral T lymphocytes. The identity of T4+cDNA clones was determined by Northern and Southern blot analyses, and ultimately by the ability of these clones to transfer the T4+phenotype to recipient cells. Similar techniques have previously been employed to isolate the gene encoding the T8 protein (20).

Mouse L cells deficient in thymidine kinase (tk) were cotransformed with genomic DNA from the T cell leukemic cell line HUT-102 along with the tk-containing plasmid, pTK (25, 26). tk+L cell transformants expressing T cell surface proteins were identified by an in situ rosetting assay. tk+colonies were exposed to mouse monoclonal antibodies directed against T4 and were then incubated with red blood cells coupled with rabbit anti-mouse immunoglobulin. T4+transformants are visibly red by virtue of their specific association with red blood cells. In this manner, one primary T4+transformant, LTD-4, was obtained. The expression of the T4 molecule by this clone was independently verified by cytofluorometric analysis (FIG. 1).

The mRNA population of the T4+transformant, LTD-4, should differ from that of an untransformed L cell only in the expression of newly transformed genes. These sequences were enriched for by annealing highly radioactive cDNA prepared from poly(A)+RNA of the T4+transformant with a vast excess of RNA from an untransformed L cell (32, 60). cDNA incapable of hybridizing, even at high Rot values, was isolated by hydroxyapatite chromatography and used to screen a human peripheral T cell cDNA library constructed in the lambda cloning vector gt10. Four weakly hybridizing plaques were identified, plaque-purified and analyzed for the presence of T4 sequences.

To determine whether any of these clones encoded T4, Northern blot analyses were initially performed with RNA from T4+and T4−peripheral T cells, leukemias, thymocytes, L cell transformants and nonlymphoid cells (FIG. 2) One of the four clones hybridized to an RNA present only in T4+cells. This clone detects a 3 kb RNA present in the T4+transformant, LTD-4, which is also present in a population of T4+peripheral lymphocytes, a variety of T4+leukemic cell lines, and thymocytes No hybridization was observed with RNA from untransformed fibroblasts, T4−peripheral lymphocytes, HeLa cells, or human neuroblastoma cells.

The pattern of expression of RNA detected by this clone is consistent with the possibility that it encodes T4. However, this cDNA is only 0.6 kb in length but hybridizes to a 3 kb mRNA. Therefore, the human peripheral T cell cDNA library was rescreened and one clone (pT4B) was obtained which contained a 3 kb insert, close in size to that of the mature messenger RNA. Restriction maps of this clone are shown in FIGS. 3A and 3B.

The plasmid pT4B has been deposited pursuant to the Budapest Treaty On The Invernational Recognition Of The Deposite of Microorganisms For The Purposes Of Patnet Procedure with the Patent Culture Depository of the American Type Culture Collection (ATCC), 12301 Parklawn Drive, Rockville, MD, 20852, U.S.A. under ATCC Accession No. 68389.

Genomic Blot Analysis

Southern blot experiments (37) were next performed to demonstrate that the isolated cDNA clone hybridized with DNA from the T4+transformant as well as human DNA, but not with untransformed mouse L cell DNA (FIG. 4). Genomic DNA from a variety of human cells reveals a set of five hybridizing fragments after cleavage with the enzyme BamHI. As expected, T4 sequences can be detected in the transformant LTD-4, but not in untransformed L cell DNA. The BamHI fragment closest to the 3' end of the gene (6.6 kb) is not present in LTD-4, presumably as a consequence of the integration event. Moreover, no gross rearrangements are apparent at this coarse level of analysis when comparing DNA from lymphoid and nonlymphoid cells. The sum of the molecular weights of the hybridizing fragments is 33 kb, suggesting that the T4 gene is quite large. A complete set of genomic clones spanning this region was obtained (see below) and the BamHI fragments were ordered by restriction analysis of these clones (FIG. 3A), confirming that the gene is large and must contain introns of significant lengths.

Expression of the T4 cDNA in Transformed Mouse Fibroblasts

Further evidence that the isolated cDNA encodes T4 would be provided if this clone could convert fibroblasts to the T4+phenotype after transformation. The T4 gene in chromosomal DNA is large and spans several genomic clones. Therefore, the cDNA clone was introduced into two retroviral expression vectors, pVcos7 and pMV6kt/neo, which contain the Moloney murine leukemia virus long terminal repeats (LTRs) flanking a single EcoRI cloning site (FIG. 3C). The 5'-LTR promotes transcription through the cloning site and the 3'-LTR contains sequences necessary for cleavage and polyadenylation. The vector pMV6tk/neo also contains the tk promoter fused to the coding region of the neomycin phosphotransferase gene. The construct employing pVcos7 requires transformation with an unlinked selectable marker, whereas pMV6tk/neo carries the neomycin resistance marker, which permits linked cotransformation. Neo+colonies of NIH 3T3 cells obtained after transformation were selected by their ability to grow in media containing the neomycin analogue G418, and were screened using the rosetting procedure to detect the expression of T4 on the cell surface. Approximately 50% of the G418 colonies obtained with pVcos7 and 75% of the colonies obtained with pMV6tk/neo were positive for T4 in this assay. Rosette-positive colonies were further analyzed by cytofluorometry to confirm that T4 is expressed on the transformed cell surface (FIG. 1).

Metabolic protein labeling experiments were performed which demonstrate that the T4+transformed fibroblast and the T lymphocyte express a T4 protein of identical molecular weight. Untransformed NIH 3T3 cells, T4+transformants and T lymphocytes were labeled for 12 hours in the presence of L-[$^{35}$S]-methionine (41). The cells were detergent solubilized and the lysate was passed over lentil lectin columns to enrich for glycoproteins (42). The bound glycoprotein fraction was eluted and immunoprecipitated with monoclonal antibodies directed against T4 (FIG. 5). Under reducing conditions, a glycoprotein migrating at a relative molecular mass of 55 kd is detected in extracts from T lymphocytes and two independent T4+transformants.

This protein is not detected in control 3T3 fibroblasts. Under nonreducing conditions, a 51 kd glycoprotein is immunoprecipitated with anti-T4 in T cells and in the transformed fibroblasts.

These experiments demonstrate that the transformants express a 55 kd glycoprotein immunoprecipitated with anti-T4 which is identical in size to that expressed on the surface of T lymphocytes. Thus, Northern and Southern analyses using the isolated cDNA, taken together with the ability of this cDNA to confer the T4+phenotype to mouse fibroblasts, indicate that the entire coding sequence of the T cell surface protein T4 had been cloned.

Nucleotide Sequence of the T4 cDNA and the Deduced Protein Sequence

The complete nucleotide sequence of the T4 coding region was determined by sequencing both strands of the 3 kb cDNA insert using the dideoxy termination method (35, 36). The complete nucleotide sequence and the predicted protein sequence are shown in FIG. 6. The longest open reading frame begins at position 76 with a methionine codon surrounded by the initiation consensus sequence PurNNATGPur (61). This reading frame extends 1374 nucleotides, encoding a polypeptide containing 458 amino acids The contiguity of this reading frame was confirmed by inserting this cDNA into the RNA expression vector pSP6 (40). RNA synthesized from this vector, when translated in vitro, directs the synthesis of an unmodified 51 kd protein, the precise molecular weight predicted from the nucleotide sequence (FIG. 7).

T4 is comprised of a leader sequence, four tandem variable-joining (VJ)-like regions, and a membrane-spanning domain each sharing homology with corresponding regions of different members of the immunoglobulin gene family (62, 63) (FIGS. 6 and 8). A stretch of hydrophobic residues, corresponding to a leader peptide predicted by a Kyte-Dolittle (64) hydropathicity plot, immediately follows the initiation codon. Although the exact position at which the native T4 protein is processed cannot be determined, it is contemplated that cleavage occurs just after the threonine at positions based on known cleavage patterns (65). Therefore, the signal peptide contains 23 amino acids and the processed T4 protein consists of 435 residues.

Residues 1–94 of the mature protein share both amino acid and structural homology with the immunoglobulin light chain variable domain (FIG. 9A). The overall homology of this domain with immunoglobulin variable regions is 32%. Sequence comparison between the V regions of light chain immunoglobulins and the N-terminal V-like region (V1) of T4 demonstrates that eight out of 14 invariant residues are conserved (66). This domain contains two cysteine residues, separated by 67 amino acids, whose positions and spacing are analogous to that found in light chain immunoglobulins and related molecules (67). These cysteines may be capable of forming the conserved intrastrand disulphide bond characteristic of V domains. This suggestion is supported by our observation that T4 migrates more rapidly under nonreducing conditions than under reducing conditions, consistent with the formation of at least one intrastrand linkage (FIG. 5, lanes e and f).

Aside from homologies at the level of individual amino acids, the V1 domain of T4 shares structural features with immunoglobulin variable regions. Immunoglobulin variable and constant domains fold in a characteristic pattern in which a series of antiparallel $\beta$-strands fold to form two $\beta$-sheets (67, 68). These $\beta$-sheets are held together both by a disulphide bridge and by characteristic hydrophobic interactions. To determine how the predicted secondary structure of the V-like domain of T4 compares with the structure of the V domains of light chain immunoglobulins, two-dimensional structural alignments were performed. Also, a plot of probable $\beta$-strands and $\beta$-turns in these sequences using the empirically derived algorithm of Chou and Fasman (69) was obtained. These analyses suggest the presence of seven $\beta$-strands within the V-like domain of T4 which closely match those found in the immunoglobulin V domain (FIG. 9A). The two conserved cysteines of T4 are found within $\beta$-strands B and F, matching exactly the positions of the cysteines in the V region known to form the conserved disulphide bond in immunoglobulin. A tryptophan residue lies 12 amino acids downstream of the first cysteine and a tyrosine residue is situated two amino acids before the second cysteine. These residues are highly characteristic of $\beta$-strands C and F, respectively in light chain V regions. In addition, an aspartate residue is found six amino acids before the second cysteine, and an arginine residue lies at the base of $\beta$-strand D. These charged residues are highly characteristic of V domains (67). Finally, patches of alternating hydrophobic residues are present throughout the β-strands, which L strengthen the interaction of the two β-sheets.

The V1 domain of T4 is followed by a stretch of amino acid residues bearing significant homology to the joining (J)regions of immunoglobulins and T cell antigen receptors. In FIG. 9B, this J-like region of T4 is aligned with the consensus joining sequences of immunoglobulin light chains and the two chains of the T cell antigen receptor. This J-like region is followed by a 265 amino acid stretch which may be structurally divided into three additional VJ-like domains with statistically significant sequence and structural homology to prototype immunoglobulin VJ regions (FIGS. 6 and 8). Additionally, this sequence contains two potential N-linked glycosylation sites (Asn-Leu-Thr; FIG. 6).

The extracellular domain is followed by a putative transmembrane sequence, predicted by a hydropathicity plot (64), which contains only hydrophobic and neutral amino acid residues. This segment bears striking homology to the transmembrane exon of the β-chains of class II major histocompatibility proteins (FIG. 9C). Alignment of the transmembrane regions of T4 and MHC class II β-chains reveals 48% homology without gaps. Following the membrane-spanning segment, a highly charged sequence of 40 amino acids comprise the cytoplasmic domain (FIGS. 6 and 8).

The T4 Gene: Chromosomal Location and Intron-Exon Positions

The T4 cDNA was used to determine the chromosomal location of the T4 gene by analyzing its segregation pattern in a panel of mouse-human somatic cell hybrids and by in situ hybridization to human metaphase chromosomes (101). Genomic blot experiments and in situ hybridization indicate that the T4 gene resides on the short arm of human chromosome 12, between regions 12p12 and 12pter.

A set of overlapping genomic clones spanning the T4 gene was obtained by screening human genomic libraries constructed in the lambda cloning vectors Charon 4 and EMLB-3 (31) with a radiolabeled pT4B cDNA insert (70). Characterization of these clones by both restriction and Southern blot analyses indicated that they contained the entire T4 coding sequence. The complete intron-exon organization of the T4 gene was then determined by sequencing specific fragments of the genomic clones using the dideoxy termination procedure (35, 36).

The T4 gene is comprised of 9 exons split by 8 introns as shown in FIGS. 8 and 10. The first exon contains the 5'-untranslated region and the leader segment. The first variable-like domain, $V_1$, is split by a large intron located at nucleotide position 289 (FIG. 6). Therefore, the $V_1J_1$ domain is encoded by the second and third exons and the $V_2J_2$, $V_3J_3$, $V_4J_4$, and transmembrane (TM) domains are each encoded by separate exons (exons 4–7). The cytoplasmic domain (CYT) is split by an intron, and the last portion of the cytoplasmic domain and the 3'-untranslated region are encoded by the ninth exon.

The Construction of T4+ and T8+ Transformed Cells

The experimental approach used to study the role of T4 in AIDS virus infection initially involved the introduction of the T4 gene into T4− cell lines incapable of supporting viral infection. The transformed cells were then tested for susceptibility to AIDS virus, followed by studies on the mechanism by which T4 mediates viral infection.

A full length cDNA clone encoding the surface protein T4 was subcloned into the retroviral expression vector, pMV7. The expression vector, pMV7 (FIG. 11A), contains two directly repeated Moloney murine sarcoma virus long terminal repeats (LTRs) which flank a single EcoRI cloning site. The 5'-LTR constitutively promotes transcription through the cloning site, whereas the 3' LTR provides sequences necessary for cleavage and polyadenylation of the RNA. In addition, pMV7 contains the herpesvirus thymidine kinase promoter (tk) fused to the coding region of the bacterial neomycin phosphotransferase gene (neo), a dominant selectable marker, permitting linked cotransformation and infection.

T4-pMV7 was introduced into ψ-2 and ψ-AM cells, NIH 3T3 cell lines containing defective ecotropic and amphotropic proviruses, respectively (FIG. 11B) (44,59). Both cell lines are incapable of encapsidating endogenous viral RNA but can provide all obligate trans viral functions. Stable transfection of these cell lines with T4-pMV7 results in the production of recombinant retroviral stocks encoding T4 which are free of helper virus. These pure viral stocks can then be used to efficiently introduce T4 sequences into both mouse and human cells without the production of retrovirus by the target cell.

Figure 11B:
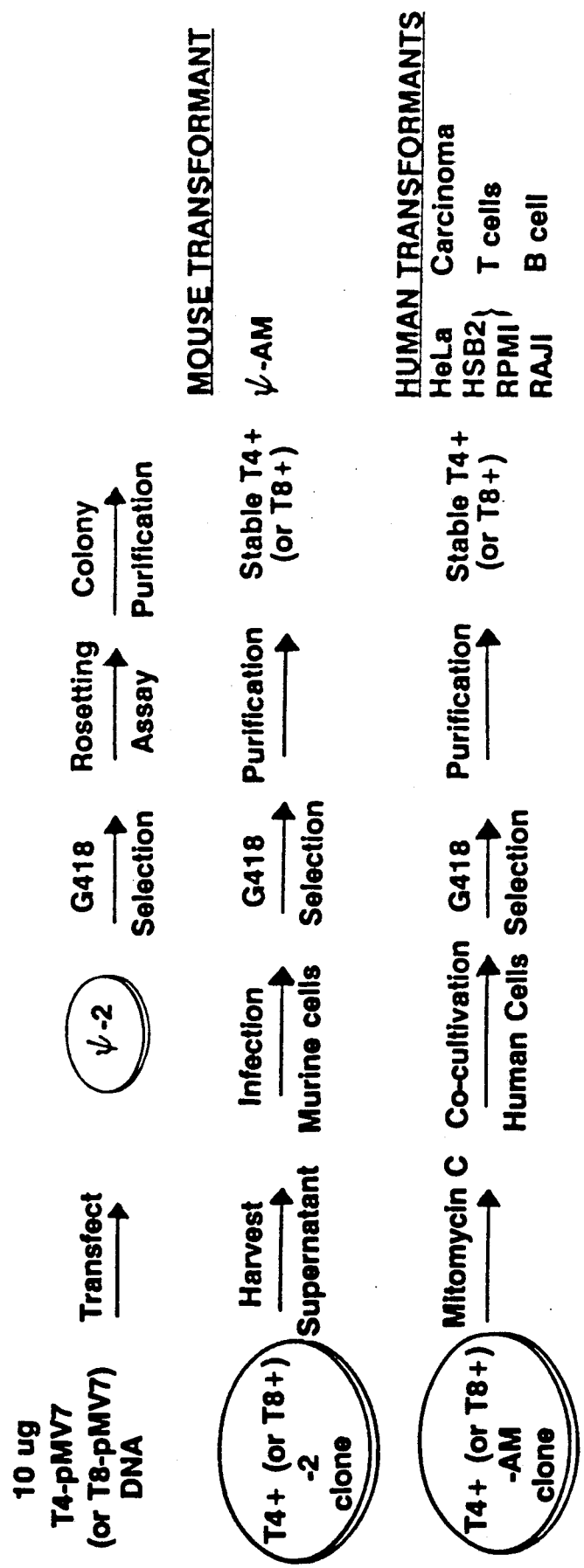

Briefly, T4-pMV7 DNA was introduced into ψ-2 cells using the procedure of DNA-mediated gene transfer (FIG. 11B) (25, 27). Neo+ positive colonies were selected by their ability to grow in media containing the neomycin analog G418 (Geneticin ®) and screened for the expression of T4 on the cell surface using an in situ rosetting assay (20, 70). Colonies of transfected ψ-2 cells expressing T4 were then identified which produce recombinant retrovirus in titers of $10^5$ cfu/ml T4+ψ-2 clones were then used to generate retroviruses capable of infecting mouse ψ-AM cells. T4 expressing ψ-AM clones were isolated which yield recombinant retroviral titers of $10^4$ cfu/ml. T4+ human transformants were generated by co-cultivation of cells with mitomycin-C treated or ψ-AM clones (FIG. 11B). T4+ transformants were subsequently analyzed by Northern blot analysis and flow cytometry to confirm that T4 is expressed and is present on the cell surface. Control cell lines expressing the surface protein T8 were constructed in an analogous manner.

T4 is Essential for AIDS Virus Infection

To initially determine whether the presence of the T4 protein on the surface of a human lymphocyte is sufficient to render the cell susceptible to AIDS virus infection, transformants of the primitive T cell leukemic line, HSB2 (71), which expresses only the early T lymphocyte proteins T1 and T11 on its surface, were constructed. HSB2 expresses neither T4 nor T8, nor does it express the T cell antigen receptor or the associated complex of T3 proteins. Transformants of HSB2 which express either the T4 or T8 proteins on the cell surface were selected and used to determine the susceptibility of these cell lines to AIDS virus infection. Several different experimental approaches were employed to assess AIDS virus infection, including expression of reverse transcriptase (52), expression of virus in the cytoplasm of the cell by immunofluorescence microscopy (46), detection of viral antigens in the culture supernatant using an immunoassay (47), as well as production of infectious virions by supernate subculture with phytohemagglutinin (PHA)-stimulated peripheral lymphocytes (46). Using these assays, evidence of AIDS virus infection of the HSB2 cell line was not observed (Table I).

TABLE I

Susceptibility of T4⁻ and T8⁻ Human Transformants to AIDS Virus Infection

| HUMAN CELL | Maximum Reverse Transcriptase | Cytoplasmic Virus | Supernate Viral Ag | Supernate Subculture | Syncytium Induction | VSV (AIDS) Pseudotype Infection | Virus Binding |
|---|---|---|---|---|---|---|---|
| CEM(T4$^{(T4-)}$) | 675023 | + | + | + | + | + | + |
| HSB2 | 4245 | − | − | − | − | − | − |
| HSB2-T8⁺ | 4460 | − | − | − | − | − | − |
| HSB2-T4⁺ | 190915 | + | + | + | + | + | + |
| Raji | ND | ND | ND | ND | − | − | ND |
| Raji-T8⁺ | 5595 | − | − | − | − | − | − |
| Raji-T4⁺ | 103500 | + | + | + | + | + | + |
| HeLa | 6438 | − | − | − | − | − | − |
| HeLa-T8⁺ | 4875 | − | − | − | − | ND | − |
| HeLa-T4⁺ | 48125 | + | + | + | + | + | + |

$5 \times 10^6$ cells were inoculated with AIDS virus, incubated at 37° C. for 24 hours, washed, and replated in fresh media. Cells and supernatants were removed at days 3, 6, 9, 12, 16, 20, 24, and 28 and used in four virus detection assays: reverse transcriptase, cytoplasmic virus, supernate viral antigen, and supernate subculture.
The results of the pseudotype infection experiments are expressed as follows:
+ ($\geq 10^3$ PFU/ml);
− (10 PFU/ml);
ND, not determined.

In addition, it has been previously demonstrated that extensive cell fusion occurs when uninfected human cells bearing receptors for AIDS virus are co-cultivated with cells producing AIDS virus (54). In this assay, there is no induction of syncytia when HSB2 cells are mixed with AIDS virus-producing H9 cells (Table I), although abundant syncytia are formed with HTLV-I and HTLV-II producing cells (data not shown).

Finally, viral entry was tested for using pseudotypes of vesicular stomatitis virus (VSV) bearing the envelope glycoproteins of the AIDS virus (Table I) (53, 54). When cells infected with AIDS virus are superinfected with VSV, a proportion of the progeny VSV assemble sufficient AIDS virus envelope glycoprotein to resist neutralization by hyperimmune anti-VSV serum. The host range of these VSV (AIDS) pseudotype virions is restricted to cells expressing receptors specific to the AIDS virus. Following penetration of the cell and uncoating of the virion, the transcapsidated VSV genome replicates to produce non-pseudotype particles. During the secondary infection, progeny VSV released from infected cells penetrate and destroy neighboring indicator cells resistant to VSV (AIDS) pseudotype infection (mink CCL64 or bovine MDBK cells), resulting in the formation of VSV plaques which are then scored. Thus, infection with VSV (AIDS) pseudotypes provides a quantitative cytopathic plaque assay for viral entry (54) In this assay, no plaques over background were observed when HSB2 cells were exposed to VSV (AIDS) pseudotypes (Table I). In control experiments with pseudotypes of VSV RNA encapsidated in an HTLV-I envelope (VSV (HTLV-I)), numerous plaques were observed, demonstrating that the HSB2 cell, which bears HTLV-I receptors, is capable of replicating VSV efficiently. These observations demonstrate that the VSV genome encapsidated in an AIDS virus envelope is incapable of entering HSB2 cells.

Whether the introduction of a functional T4 cDNA into HSB2 would render this cell susceptible to AIDS virus infection was next studied (Table I). Exposure of HSB2-T4⁺ transformants to AIDS virus results in a productive viral infection as determined by expression of reverse transcriptase activity (52), expression of virus in the cytoplasm of the cell by immunofluorescence microscopy (46), detection of viral antigen in the culture supernatant using an immunoassay (47), as well as the production of infectious virus by supernate subculture with PHA-stimulated lymphocytes (Table I) (46). Control HSB2-T8⁺ cells were consistently negative in each of the assays.

In addition, the efficiency with which different T4⁺T cells are infected with AIDS virus was also examined. HSB2-T4⁺ and HSB2-T8⁺ transformants, the naturally-isolated T4⁺T cell line CEM, as well as PHA-stimulated peripheral lymphocytes were exposed to serial 10-fold dilutions of AIDS virus, washed, and plated in microculture. The frequency of infected cultures was then determined using an immunoassay 12 days after exposure to virus (FIG. 12) (47). In this manner, the titer of AIDS virus required to infect 50% of the exposed cultures (ID-50) was defined. The ID-50 of PHA-stimulated peripheral lymphocytes is 2–3 orders of magnitude greater than that observed for either naturally-isolated or transformed T4⁺ cell lines The efficiency of infection of HSB2-T4⁺ cells is about 10 fold higher than that observed for the naturally-isolated T4⁺T cell line CEM (FIG. 12). Control HSB2-T8⁺ cells are not susceptible to infection even at the highest virus titers examined.

The ability of HSB2-T4⁺ cells to support both syncytia formation and the replication of VSV (AIDS) pseudotypes was also studied. When HSB2-T4 cells, are co-cultivated with AIDS virus producing H9 cells, syncytia formation is readily observed within 18 hours (Tables I and II). Moreover, syncytium induction is abolished by pretreating cultures with anti-T4A monoclonal antibody (Table II). Finally, when HSB2-T4⁺ cells are exposed to VSV (AIDS) pseudotypes, infectious VSV particles are produced which destroy neighboring indicator cells (Tables I and III). Furthermore, plaque formation is inhibited by pretreatment with either anti-AIDS virus antibody or anti-T4A monoclonal antibody (Table III). Control HSB2-T8⁺ cells are consistently negative in each of the seven assays employed to detect AIDS virus infection (Tables I, II, and III). These observations provide genetic evidence that in an immature human T lymphocyte, the mere presence of the T4 protein provides an essential function required for AIDS virus infection

TABLE II

Induction of Syncytia in T4⁻ Human Transformants

| HUMAN CELLS | SYNCYTIUM INDUCTION | |
|---|---|---|
| | H9/AIDS | H9/AIDS + αT4A |
| JM(T4⁻) | + + + + + | − |
| 8166(T4⁻) | + + + + + | − |
| HSB2 | − | ND |
| HSB2-T8⁺ | − | ND |
| HSB2-T4⁺ | + + | − |
| Raji | − | ND |
| Raji-T8⁺ | − | ND |
| Raji-T4⁺ | + + + | − |
| HeLa | − | ND |
| HeLa-T8⁺ | − | ND |
| HeLa-T4⁺ | + + + + + | − |

2 × 10⁵ cells were co-cultivated with 2 × 10⁴ AIDS virus-producing H9 cells (H9/AIDS) and incubated at 37° C. The cultures were examined for syncytia formation after 18 hours. The results are expressed as the approximate percentage of nuclei contained within syncytia:
− (no syncytia);
+ + (25%);
+ + + (50%);
+ + + + + (90%);
ND (not determined).
Syncytium inhibition was assayed by adding anti-T4A monoclonal antibody (αT4A; 1:20) to the mixed cultures at the time of seeding. The naturally-isolated T4⁻ T cell lines JM and 8166 served as positive controls in these studies.

TABLE III

VSV Pseudotype Cytopathic Plaque Assay on T4⁻ and T8⁺ Human Transformants

| | VSV PSEUDOTYPE TITER (PFU/ml) | | | | |
|---|---|---|---|---|---|
| | VSV (HTLV-I) | | VSV (AIDS) | | |
| HUMAN CELLS | | + αHTLV-I | | + αAIDS | + αT4A |
| CEM(T4⁻) | 20,000 | 50 | 42,000 | 50 | 200 |
| HSB2-T8⁺ | 10,000 | 50 | 0 | ND | ND |
| HSB2-T4⁺ | 12,000 | 50 | 1,000 | 100 | 300 |
| Raji-T8⁺ | 5,000 | ND | 0 | ND | ND |
| Raji-T4⁺ | 5,000 | 50 | 1,500 | 25 | 150 |
| HeLa | 10,000 | ND | 0 | ND | ND |
| HeLa-T4⁺ | 10,000 | 50 | 17,000 | 50 | 200 |

2 × 10⁵ cells were incubated with VSV (AIDS) pseudotypes (53, 54) for 1 hour at 37° C. The cells were then washed and 1 × 10⁶ mink CCL64 or bovine MDBK plaque indicator cells, permissive to VSV infection but resistant to VSV (AIDS), were added to each well. The cultures were then overlaid with agar medium and scored for VSV plaques two days post infection. Anti-T4A monoclonal antibody (αT4A; 1:20) or anti-AIDS virus serum (αAIDS, 1:10) were used to inhibit VSV (AIDS) pseudotype plaque formation by pretreatment of cells 30 minutes before exposure to pseudotypes (54). VSV (HTLV-I) pseudotypes, which plate on a wide variety of human cell types (54), were used as controls in these experiments. Anti-HTLV-I serum (1:10) was used to block VSV (HTLV-I) pseudotype plaque formation. The results are expressed as PFU/ml; ND (not determined).

AIDS Virus Infection Is Not Restricted to T Lymphocytes

A functional T4 cDNA was introduced into two human non-T cell lines HeLa, an epithelial cell line derived from a cervical carcinoma (72), and Raji, a B lymphoblastoid cell line derived from a patient with Burkitt's lymphoma (73) (FIG. 11B). Prior to retrovirus-mediated gene transfer, these cell lines do not express surface T4 protein or T4 mRNA, nor are they susceptible to AIDS virus infection (Table I). In addition, the parental cell lines do not support the induction of syncytium nor the plating of VSV (AIDS) pseudotypes (Tables I, II and III).

In contrast, T4⁺Raji and HeLa transformants support AIDS virus infection by all of the criteria previously described (Table I). The efficiency with which Raji-T4⁺ cells can be infected with AIDS virus approximates that of HSB2-T4⁺cells and is about 10 fold higher than the efficiency of infection of the naturally-isolated T4⁺T cell line CEM (FIG. 12). Moreover, upon cocultivation with AIDS virus-producing H9 cells, Raji-T4⁺ and HeLa-T4⁺cells support the induction of syncytia which is abolished by pretreating cultures with anti-T4A monoclonal antibody (Tables I and II; FIG. 3). In addition, exposure of these cells to VSV (AIDS) pseudotypes results in the production of infectious VSV and the formation of plaques which are inhibited by pretreatment with anti-AIDS virus antibody or anti-T4A monoclonal antibody (Tables I and III). Control Raji-T8⁺ and HeLa-T8⁺transformants are consistently negative in each of these assays (Tables I, II, and III).

Therefore, the introduction of a functional T4 gene into either human T lymphocytes, B lymphocytes, or epithelial cells is sufficient to render such cells susceptible to AIDS virus infection. Taken together, these observations indicate that the T4⁺T cell tropism observed in vivo is a consequence of the restricted expression of the T4 molecule and not the nature of the cell type in which it is expressed.

AIDS Virus Binds to Surface T4 Protein

The previous experiments provide genetic evidence that T4 expression is required for AIDS virus infection but do not provide information on the role of this molecule in the viral life cycle. The observation that surface expression of T4 is necessary for AIDS virus infection suggests that T4 is the AIDS virus receptor. Cytofluorometry was therefore used to examine the binding of AIDS virus to the surfaces of T4⁺and T8⁺transformed human cells (Table I; FIG. 14). HSB2, Raji, and HeLa cells, and the T4⁺or T8 transformants, were incubated with AIDS virus. Following viral absorption, the cells were washed, exposed to fluorescein-conjugated anti-AIDS virus antibody, and analyzed by flow cytometry. This assay indicated that the AIDS virus binds efficiently and specifically to the human transformants expressing surface T4, but not to the T4⁻parental cells nor to the T8⁺transformants (FIG. 14, column B; Table I). The binding of AIDS virus to the T4⁺cells is abolished by preincubation with anti-T4A monoclonal antibody but not by preincubation with antiT8 monoclonal antibody (FIG. 14, column C). Moreover, when T4⁺transformed cells are exposed to AIDS virus, the T4 glycoprotein coprecipitates with the viral envelope glycoprotein, suggesting a direct physical association between these molecules (data not shown). These results indicate that the AIDS virus binds to the T4 molecule on the cell surface and that this binding is independent of other T cell-specific proteins since binding occurs to all T4⁺cell types examined.

Previous studies have described two distinct pathways of entry for enveloped viruses (74, 75, 76, 77). Some viruses fuse directly with the plasma membrane, releasing their nucleocapsids into the cytoplasm, whereas others are internalized by receptor-mediated endocytosis. The acidic environment of the endosome then facilitates fusion of the viral envelope with the limiting membrane of the vacuole. Infection by viruses which enter cells via the endocytic pathway can be inhibited by treating cells with agents such as weak bases which deacidify the endosome (58, 78, 79, 80). In the presence of ammonium chloride, fusion is blocked in the endosome but lysosomal degradation still proceeds at a reduced rate (80).

The effect of ammonium chloride on AIDS virus infection of the T4$^-$T cell line JM was therefore examined In the absence of ammonium chloride, over 50% of JM cells exposed to AIDS virus express viral antigens five days after infection as determined by immunofluorescence microscopy. If JM cells are exposed to ammonium chloride (for 6 hours) either at the time of addition of virus or within 30 minutes after the addition of virus, greater than 95% inhibition of viral infection was observed However, if cells were treated with ammonium chloride one hour after the addition of virus, no inhibition of infection was observed, a finding consistent with the kinetics of viral entry described for other viruses which enter cells via receptor-mediated endocytosis. Finally, the ammonium chloride effect was completely reversible Cells exposed to ammonium chloride for one hour, and then washed free of the compound and exposed to AIDS virus, supported control levels of viral infection. These results are consistent with previous observations that upon removal of ammonium chloride, the pH of the endosome returns to the original low values within 1-2 minutes (78, 80). Similar results with amantadine, a compound which deacidifies the endosome, were obtained.

Figure 15A:

These results are consistent with a mechanism of viral entry which involves endocytosis of the T4-AIDS virus complex and low pH-induced fusion of the viral envelope with the limiting membrane of the endosome, releasing the viral nucleocapsid into the cytoplasm of the cell T4 mRNA is Expressed in the Brain In addition to the disruption of the cellular immune system, AIDS is frequently accompanied by central nervous system (CNS) disorders which are thought to be the consequence of the direct infection of brain cells by the AIDS virus (81). It was therefore of interest to determine whether T4 is expressed in cells within the CNS, thereby providing an explanation for the neurotropic properties of the virus Northern blot analyses of RNA prepared from both human and mouse brains were performed to determine whether T4 mRNA sequences are expressed in the CNS (FIG. 15). Poly(A)$^{+-}$ RNA derived from human cerebral cortex contains two distinct T4 mRNAs with molecular weights of approximately 3 and 1.8 kb (FIG. 15A). The weaker 3 kb RNA is identical in size to the mRNA expressed by two T4$^+$leukemic cell lines, U937 (monocytic cell line) and Jurkat (T cell line), as well as by peripheral T lymphocytes The smaller, more abundant 1.8 kb mRNA absent from T lymphocytes could result from alternative splicing or alternative 5' or 3' termini.

Figure 15B:
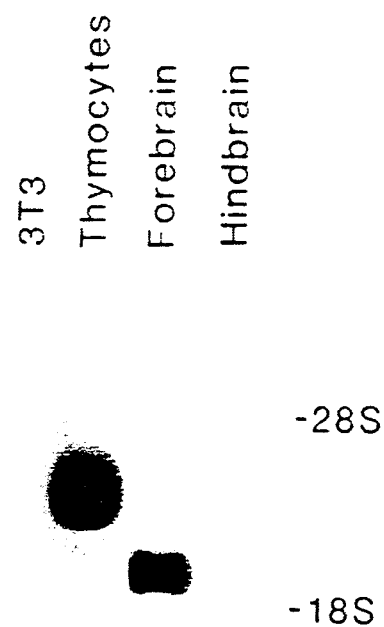

A more careful analysis of the localization of T4 mRNA was performed by isolating poly(A)$^+$RNA from specific regions of the mouse brain (FIG. 15B). Hybridization with radiolabeled cDNA encoding the murine homologue of T4, L3T4, reveals an intense 2.2 kb mRNA in mouse forebrain which is absent from hindbrain samples. The 2 2 kb L3T4 mRNA is detectable in the cortex, hypothalamus, and is most abundant in the striatum, but is absent from the cerebellum, brain stem, or spinal cord (data not shown) This 2.2 kb mRNA detected in the CNS is approximately 1 kb smaller than the 3.2 kb mRNA encoding L3T4 in thymocytes (FIG. 15B). These results indicate that the neurotropism displayed by the AIDs virus is likely to be the result of surface expression of the T4 molecule on brain cells The level of mRNA detected in forebrain is about 1/30th the level in thymocytes. This may reflect low level expression by a large number of cells or higher levels of expression by a small subpopulation of cells. It is not known at present whether T4 is expressed by neurons or supporting cells. The presence of a variant transcript in the CNS, however, makes it unlikely that the T4 mRNA in brain is expressed by the rare invading T lymphocyte.

Discussion

The segregation of T4 and T8 with functionally distinct subsets of T cells suggests that these molecules may be important in the interaction of T lymphocytes with appropriate target cells. As a first step in understanding the specific role of these proteins, cDNA clones were obtained of both the T4 and T8 molecules and their nucleotide sequences were determined (20, 70). Comparison of the deduced protein sequences of T4 and T8 indicates that these molecules share significant sequence and structural homology with immunoglobulin variable (V) domains and as members of the immunoglobulin supergene family. However, the N-terminal V-like domains of T4 and T8 are quite different: they share only 28% homology and are therefore less homologous to each other than each is to immunoglobulin light chains (FIG. 9A). Moreover, the regions of maximum conservation between T4 and T8 are also the regions of strongest homology to immunoglobulin and T cell receptor V regions. Thus, the immunoglobulin-like domains of these two molecules, although structurally similar, show significant sequence divergence consistent with the hypothesis that they recognize different molecules on different subsets of target cells.

The V-like region structural homology shared by the Nterminal domains of T4 and T8 may be of particular relevance to the functions of these proteins Virtually all members of the immunoglobulin supergene family participate in the immune response (62). Moreover, the individual members of this family show a strong tendency to associate with each other to form dimers. This association is apparent in the interaction of the heavy and light chains of immunoglobulin, the alpha and beta chains of the T cell antigen receptor, $\beta$2-microglobulin and class I MHC proteins and the alpha and beta chains of class II MHC molecules. The T8 glycoprotein forms a disulphide bond with T6, a presumed MHC-like molecule, on the surface of thymocytes (82), and exists as multimers of the 32 kd subunit on peripheral T lymphocytes (83). The presence of four V-like domains in T4 indicates that these regions associate with one another as well as with specific ligands on the surface of other cells or viruses. These specific affinities of immunoglobulin-like molecules may be essential for the recognition functions of T4 and T8.

Evolution of T4

In the immunoglobulin and T cell antigen receptor genes, the V and J exons are widely separated and become juxtaposed only after a somatic recombination event (62, 63). The T4 mRNA encodes four contiguous V-and J-like elements without the requirement for DNA recombination events. It is therefore possible that T4 reflects a more primitive gene that evolved before the emergence of rearrangement mechanisms. Further support for this derives from recent observations that the first V-like region of T4 (V1) is split by an intron not present in the V genes encoding either the immunoglobulins or T cell antigen receptors. Accumulating evidence suggests that it is far more likely for introns to be precisely removed during evolution that for introns to be inserted in a previously intron-free environment Thus, T4 may represent an ancestral immunoglobulin gene which underwent duplications, divergence, and rearrangement to generate the current immunoglobulin gene family. Although functional in a far more complex immune system at present, T4 may reflect receptors operative in more primitive cellular immune responses. Primitive immune responses, such as those of invertebrates, do not appear to involve a diverse repertoire of receptor molecules, but in the simplest cases are restricted to a distinction between self and nonself (85, 86) and are likely to be accommodated by a "static" set of genes that do not undergo rearrangement.

Whatever the order of appearance of T4 in evolutionary time, the organization of this gene reveals an interesting example of exon shuffling. T4 consists of four V-J-like domains, a J-like region and a transmembrane segment, each sharing homology with different members of the immunoglobulin supergene family. The V- and J-like domains are homologous to the equivalent regions of both immunoglobulins and the T cell antigen receptor chains; the transmembrane domain shows considerable homology to this region in the $\beta$-chains of class II MHC molecules (FIG. 9C). T4, therefore, consists of a collection of exons conserved in several members of the immunoglobulin supergene family which are shuffled in different ways to generate a large number of different molecules which participate in the immune response.

T4 is the AIDS Virus Receptor

The data provided herein suggest a mechanism of AIDS virus infection which initially involves the specific association of the AIDS virus with T4 molecules on the cell surface. This association may be demonstrated on T lymphocytes, B lymphocytes, and epithelial cells, and therefore does not require the participation of additional T cell-specific proteins. Additionally, the data provided herein indicates that the T4-AIDS virus complex is internalized via receptor-mediated endocytosis and the viral envelope then fuses with the limiting membrane of the endosome, releasing the nucleocapsid into the cytoplasm. Viral replication and transcription can then occur in both lymphoid and non-lymphoid cell lines. Moreover, the T4 gene is expressed in the brain as well as in lymphocytes, providing an explanation for the dual neurotropic and lymphotropic character of the AIDS virus In this manner, a T lymphocyte surface protein important in mediating effector cell-target cell interations has been exploited by a human retrovirus to specifically target the AIDS virus to populations of T4+cells.

Cell surface receptors have been identified for a number of enveloped viruses and the pattern of expression of these receptors is often responsible for the host range and tropic properties of specific viruses (74, 76). Some viruses will infect only a narrow range of cell types, reflecting the expression of the viral receptor on specific populations of target cells. Rabies virus, for example, interacts with the nicotinic acetylcholine receptor (87) and infects largely skeletal muscle and neurons, whereas the Epstein-Barr virus interacts with the C3d complement receptor type 2 (88) and infects B lymphocytes. Other viruses, such as the myxoviruses, interact with ubiquitously distributed sialic acid residues on the cell surface and infect a much broader range of cell types.

The restricted expression of cell surface receptors provides only one explanation for viral tropism. Some viruses will replicate only in a restricted set of differentiated cell types whereas others will only be efficiently transcribed in specific cell types. Hence, the Moloney murine leukemia virus (Mo-MuLV) induces T cell lymphomas in newborn mice,, yet the closely-related Friend helper murine leukemia virus (Fr-MuLV) induces primarily erythroleukemias (89, 90, 91). This tropism is thought to result from differences in the LTRs which facilitate the efficient transcription of the Mo-MuLV genome in T lymphocytes and the Fr-MuLV genome in erythroid precursors (92, 93, 94).

As indicated herein, the primary tropic determinant of the AIDS virus is the expression of the T4 protein on the surface of the target cell In vivo infection is restricted to lymphoid cells and myeloid cells as well as brain cells: three populations which express T4. In vitro demonstrations indicate that the introduction of T4 into T4−human B lymphocytes and epithelial cells, cells which are not natural targets for AIDS virus, renders these cells susceptible to productive infection by AIDS virus.

EXAMPLE 1

Soluble T4 Fraqments

Soluble T4 glycoprotein fragments are prepared using limited protease digestion from cell preparations. Alternatively, DNA expression vectors encoding T4 fragments which lack the transmembrane domain, a region containing neutral and hydrophobic residues, may be constructed and used to produce such T4 fragments. These fragments are soluble in aqueous solutions and contain leader (signal) sequences. When expressed in mammalian cells, these fragments are transported to the rough endoplasmic reticulum/golgi complex and eventually secreted from the cells.

EXAMPLE 2

Treatment of AIDS Patients

Soluble T4 glycoprotein fragments as described in Example 1, tyically in a pharmaceutically acceptable carrier, are administered to patients infected with a human immunodeficiency virus so as to bind to virus present in the the subject,s blood and other body fluids and block infection of T4+cells in vivo. Alternatively or additionally, a patient,s blood is cycled through a column containing either immobilized T4 glycoproteins or soluble T4 fragments so that the virus may be separated from the blood. Such measures permit the immune system to mount a more effective immunologic response against the virus, i.e., allow uninfected T4+T cells to proliferate.

Soluble T4 fragments are used as a therapeutic, i.e., an inhibitor of extracellular and cell-cell spread of HIV infection. Applicants have shown that soluble T4 fragments inhibit in vitro HIV binding to, and infection of, T4+ target cells (see Example 4). Administration of soluble T4 fragments to persons infected with HIV inhibits extracellular spread of the virus infection. Additionally, fusion of HIV-infected T4+ cells and noninfected T4+ cells, which is also a route by which the virus spreads, are inhibited by administration of soluble T4 fragments.

Therefore, administration of soluble T4 fragments slows the course of disease, alleviates several symptoms associated with AIDS, and prevents occurrence of new pathologic changes.

Soluble T4 fragments, biochemically pure, aqueous soluble reagents, are used in combination with other reagents to assay for competitors of the T4-HIV interaction Thus, soluble T4 fragments, in combination with HIV envelope proteins or biochemical mixtures containing HIV envelope proteins, are used to screen for inhibitors of viral binding.

EXAMPLE 3

Production of Soluble T4 Fragments

A cDNA encoding the membrane-bound T4 protein (pT4B) has been isolated, characterized, and expressed in a variety of mammalian cell types (70). Soluble T4 fragments are produced in bacterial, yeast, insect, and mammalian systems. Because the T4 protein likely folds in a complex manner and is glycosylated, expression in mammalian systems is preferred. Soluble T4 fragments are produced by truncating pT4B after the $V_4J_4$ domain. Such DNA fragments terminate before the transmembrane segment, which begins at approximately nucleotide position 1264 (FIG. 6). This recombinant DNA molecule lacks both the transmembrane and the cytoplasmic domains. The EcoRI-HpaII fragment, which encompasses nucleotides 1 through 1252, is isolated by assemblying it from smaller fragments of pT4B. Alternatively, the membrane-spanning segment alone is deleted, leaving the $V_4J_4$ domain fused to the cytoplasmic domain. One approach is to delete the fragment spanning the HpaII sites from nucleotides 1252–1342 from pT4B. Such constructs maintain the T4 signal sequence necessary for entry into the rough endoplasmic reticulum/golgi complex and eventual secretion from the cell. In addition, these constructs maintain the extracellular portion of the T4 protein in which the binding domain for the human immunodeficiency virus envelope glycoprotein exists.

In order to express soluble T4 fragments in mammalian systems, the modified T4 cDNA fragment is subcloned into vectors containing strong eukaryotic promoters/enchancers as well as polyadenylation sites required for cleavage and polyadenylation of the RNA. For example, the simian virus (SV40) early promoter and enchancer is positioned upstream from the soluble T4 cDNA fragment. Transcription termination and RNA polyadenylation are achieved by placing the polyadenylation site of either SV40 or the human growth hormone gene downstream from the soluble T4 cDNA fragment. Introduction of a construct containing these elements together with a selectable marker into eukaryotic cells by any of several methods known in the art leads to the stable integration of exogenous DNA. Transformants selected by virtue of their ability to grow in selective media secrete soluble T4 fragments into the culture supernatant. Soluble T4 fragments are detected in the supernatant by one of several assays, e.g. radioimmunoprecipitation, and then purified.

Purification and characterization of soluble T4 fragments is greatly enhanced by constructing a cell line which overexpresses the secreted protein fragment. Strategies which allow the overexpression of proteins have been employed in bacteria, yeast, insect, and mammalian systems. Inducible expression systems have also been employed in bacteria and yeast to overproduce proteins which may be toxic if constitutively expressed. Overexpression of soluble T4 fragments is accomplished by amplifying a soluble T4 expression vector, resulting in constitutive overexpression The amplification of dihydrofolate reductase (dhfr) genes by growth in progressively increased concentrations of the drug methotrexate, an antagonist of dhfr, has been widely employed. Since the amplified unit is not limited to dhfr coding sequences, this approach results in the coamplification of sequences adjacent to them. Therefore, dhfr is used as a selectable marker and as a means of coamplifying newly introduced sequences. This strategy has been successfully employed to increase the expression of several different genes cotransformed with dhfr plasmids. An alternative amplification scheme involves cotransfection of the soluble T4 cDNA expression vector with the plasmid pdLAT-3 followed by a selection scheme as previously described (102).

Therefore, the soluble T4 cDNA expression construct is cotransfected with a dhfr expression plasmid. Alternatively, the dhfr gene resides on the same plasmid as the soluble T4 cDNA fragment, allowing linked cotransformation Transfection of these constructs into dhfr-deficient (dhfr−) Chinese hamster ovary (CHO) cells and subsequent selection in methotrexate permits the isolation of stable transformants that express newly introduced sequences. Several clones are purified and culture supernatants collected and assayed for the presence of soluble T4 fragments Clones which produce the greatest levels of soluble T4 fragments are further characterized by Northern and Southern blot analyses These cell lines are then cultivated in selective media containing stepwise increased concentrations of methotrexate This selective pressure results in the amplification of the newly introduced dhfr gene and adjacent T4 sequences After reaching the highest methotrexate concentration, surviving cells are subjected to Northern and Southern blot analyses to determine the extent of amplification and culture supernatants are examined for the presence of soluble T4 fragments.

In order to characterize the soluble T4 fragments in the culture supernatant, several transformants are metabolically labeled with ($^{35}$S)-methionine Cell lysates and supernatants are then analyzed by radioimmunoprecipitation and Western blot analysis using commercially available anti-T4 antibodies SDS-polyacrylamide gel electrophoresis is performed on the precipitates and a band of the predicted relative molecular mass ($M_r$) of the secreted, truncated form of T4 is observed Because it is synthesized in a mammalian system, this protein is properly glycosylated and folded, i.e. disulphide bridges are formed In order to purify the soluble T4 fragments from culture supernatant, immunoaffinity column chromatography is performed using anti-T4 antibodies. Protein bound to the column is eluted at high salt concentrations and low pH. SDS-polyacrylamide gel electrophoresis of the eluted material is performed in order to determine the $M_r$ and purity of the eluted protein fraction In addition, radioimmunoprecipitation and Western blot analysis is also performed in order to further characterize the affinity-purified material.

Similar approaches may be undertaken in bacteria, yeast and insects to produce soluble T4 fragments. In addition, fragments smaller in size than the one described herein, e.g. containing only the $V_1J_1$ domain may be produced.

Construction of vectors

Using recombinant DNA manipulations, base pairs (bp) 1-1257 of the human T4 cDNA sequence were placed between an SV-40 early promoter and a TAA termination codon followed by the polyadenylation region of the bovine growth hormone gene. This sequence of the T4 cDNA encodes the leader and predicted extracellular domain of the T4 receptor. This sT4 minigene was joined with a human H-ras, or a mouse dihydrofolate reductase minigene, to create the vectors pST4CHras and pST4DHFR respectively. The construction of these vectors was as follows:

Construction of pST4sal: Plasmid pST4sal was constructed from two other plasmids, JRT4 and pUCsT4. The construction of these plasmids is detailed below.

Construction of plasmid JRT4: To create plasmid JRT4, plasmid DSPI (103) was cut with XhoI, the SV40 polyA early region was deleted and the Xho I sites were filled in using Klenow fragment of DNA polymerase. The bovine growth hormone polyadenylation region (113) was cut with PvuII and KpnI, and the KpnI site was blunted by treatment with T4 DNA polymerase. This 230 bp fragment was ligated to DSPI to create DSPIBGH.

DSPIBGH was cut with SmaI and SalI and the galK cassette (consisting of the SV40 early promoter, galK coding region and BGH polyA region) was ligated into pUC19 (107) at the SalI site by using a synthetic linker consisting of a SalI end, a BglII site, and a SmaI end. This three part ligation resulted in plasmid DSPIBZBGH.JT DSPIBZBGH.JT, which was cut with StuI and BclI to delete the galK coding region, was ligated to a 1.7 kb EcoRI (filled in)-BamHI fragment, containing the T4 cDNA from plasmid pT4B (70) to create plasmid JRT4.

Construction of plasmid pUCsT4: To create plasmid pUCsT4, a HaeII and HpaII fragment (1125 bp) of the T4 cDNA from plasmid pT4B was ligated through the use of synthetic linkers to vector pUC18 which had been cut with KpnI and XbaI. The HaeII end of the T4 cDNA was ligated to the KpnI site of pUC18 using a synthetic linker with a Kpn I end and a HaeII end. The HpaII end of the T4 cDNA was ligated to the XbaI site of pUC18 using a synthetic linker with a HpaII end and an XbaI end. This linker also inserted a TAA stop codon after nucleotide 1257 of the T4 coding region. The resulting plasmid was pUCsT4.

To create plasmid pST4sal, plasmid JRT4 was cut with BglII and SacI and 959 bp fragment (consisting of the SV40 early promoter and the first 602 nucleotides of the T4 cDNA) was isolated. Plasmid pUCsT4 was cut with SacI and XbaI and a 660 bp fragment (consisting of the T4 cDNA from nucleotides 603-1257 followed by the TAA codon from the synthetic linker) was isolated. These two fragments were ligated into DSPIBZBGH.JT which had been cut with BglII and XbaI to delete the SV40 early promoter and full length T4 coding region. The resulting plasmid was pST4sal.

Construction of pST4DHFR: To create plasmid pST4DHFR, a BglII-BamHI fragment containing a β-globin DHFR expression cassette was ligated into the BamHI site of pST4sal. The β-globin DHFR expression cassette consists of: the mouse β-globin promoter (550 bp HincII fragment from plasmid pPK288 (108) modified at its 5' end with a synthetic linker to contain a BglII site; the mouse DHFR coding region (735 bp HindIII (fill-in) fragment from plasmid pSV2-DHFR (109); NheI (fill-in)BamHI (fill-in) SV40 polyA early region from DSPI (103); and the mouse DHFR terminator region (907 bp HindIII (fill-in fragment from plasmid mDH9 (110), modified at its 3' end with a synthetic linker to create a BamHI site. The plasmid map of pST4DHFR is shown.

Construction of pST4cHras: Plasmid pMERcHras was created by cutting plasmid pSVK (111) with EcoRV and HindIII (fill-in), to remove the galK region, and ligating in an 870 bp NdeI (fill-in)-SalI (blunted by mung bean nuclease) fragment, containing the coding region for cHras, from plasmid pSKcHras (112).

The soluble T4 transcription cassette was removed from pST4sal via a BglII-BamHI fragment and ligated into the BamHI site (3' to the SV40 polyA early) of pMERcHras to create pST4cHras.

Expression of soluble T4 (sT4) minigenes in mammalian cells

Expression of psT4cHras in NIH-3T3 cells: Plasmid pST4cHras (10 μg) was co-precipitated by the calcium phosphate precipitation method with 10 μg of plasmid pTKneo, a vector conferring G418 resistance, in the presence of 10 μg carrier DNA (NIH-3T3 genomic DNA) onto NIH-3T3 cells (seeded at $5 \times 10^5$ cells per 60 mm culture dish on the preceding day). The cells were incubated with the precipitated DNA for 6 hours at 37° C. The DNA precipitate was removed and fresh media (DMEM, 5% Nu-Serum ®(Collaborative Research, Inc., Lexington, MA)) was added to the dishes The cells were trypsinized 16 hours later and seeded into three 100 mm dishes and maintained in the above media. Foci (approximately 50 per dish) appeared in 12-14 days Eleven of the transformed foci were selected, expanded and then seeded at $5 \times 10^5$ cells per 100 mm dish for selection in the above media plus 500 μg/ml GENETICIN®G418 (Gibco Laboratories, Grand Island, NY). All 11 clones survived G418 selection (500 μg/ml) and were screened for H-ras (p21) levels by standard protein immunoblot analysis.

The clones which expressed the highest levels of p21 (approximately 2 ng p21/μg Triton-soluble protein) were assayed for expression of sT4. Confluent cultures were incubated for 18 hours with $^{35}$S-labelled methionine and cysteine Culture supernatants and cell lysates were immunoprecipitated with monoclonal antibodies specific for the T4 (OKT4, OKT4A) and the T8 (OKT8) receptors, polyclonal antibody specific for ras proteins, or nonspecific mouse IgG. A protein of about 45 kd, the predicted size of sT4, was specifically precipitated from the culture medium by both of the monoclonal antibodies directed against the T4 receptor The sT4 band was not observed in cell lysates. As expected, p21 was precipitated from the cell but not from the culture supernatants. Subsequent quantitation shows, compared to purified sT4, these cells produce relatively low levels of sT4, i.e., approximately 100 fold lower than with CHO cells as described in Example 2B.

Expression of pST4DHFR in Chinese Hamster Ovary (CHO) cells: DXB-11 cells, a DHFR deficient CHO cell line (104) were transfected by calcium phosphate precipitation with 10 to 30 μg of pST4DHFR in the presence of 10 μg carrier DNA (NIH-3T3 genomic DNA), one day after seeding 60 mm dishes with $5 \times 10^5$ cells. Cells were incubated with the DNA precipitate for 6 hours at 37 C, the media was removed, and fresh media (F12, 10% FBS, 100 units/ml penicillin and streptomycin) was added to the dishes. The media was changed again after 16 hours and the cells were incubated for another 24 hours. The cells were then trypsinized, seeded into three 100 mm dishes and selected in nucleoside-free media (F-12 without hypoxanthine and thymidine, 10% dialyzed FBS, and 100 units/ml penicillin and streptomycin). Colonies (approximately 100 per dish) appeared in 7-10 days. Colonies from each dish were pooled, expanded and then seeded at $5 \times 10^3$ and at $5 \times 10^4$ cells per well in 24 well culture plates, or at $5 \times 10^5$ cells per 100 mm dish. The cells were allowed to recover for 3 days before beginning selection in nucleoside free media containing 20 nM methotrexate (mtx). Individual wells or clones were assayed at confluence for sT4 expression, and those selected for further amplification were seeded into 24 well culture plates at the densities described above. Selection at 800 nM mtx in nucleoside-free media was started 3 days after seeding. This selection procedure was repeated for selections at 8 μM mtx and 80 μM mtx.

Several cell lines were derived using this method which express soluble T4 at a minimum of 3 pg/cell/24 hrs.

Purification of sT4: Conditioned medium (CM) was prepared serum-free from adherent cell cultures expanded into 850 cm² roller bottles under mtx selective conditions. At confluence, the cells were washed twice with phosphate buffered saline (PBS) without $Mg^{2+}$ and $Ca^{2+}$ and the growth medium (Ham's F12 without hypoxanthine and thymidine, 10% fetal bovine serum, 100 units/ml penicillin and streptomycin and mtx at the selective serum and mtx and plus 1 ×ITS (insulin, transferring and selenium (Collaborative Research Inc.). After 24-48 hrs., the medium was removed and replaced with selective growth medium. Serum-free medium was then reapplied within 3-5 days and this cycle repeated indefinitely, i.e., for more than two months. CM was clarified by centrifugation at $8,000 \times g$. A protease inhibitor PMSF (phenylmethylsulfonylfluoride) was added to 0.5 mM and the CM was concentrated about 10-fold by pressure membrane filtration. This concentrated CM was clarified by centrifugation at $2000 \times g$ and Aprotinin, protease inhibitor (Sigma Chemical, St. Louis, MO) was added to a final concentration of 5 μg/ml. The sample was processed directly or after storage at $-70°$ C.

The concentrated CM sample was diluted 2-fold with 50 mM MES [2-(N-morpholino)-ethanesulfonic acid], pH 6.0 and filtered through a 0.45 micron filter. The sample was then treated with 100 μm pAPMSF (p-amidinophenylmethylsulfonylfluoride) (CalBiochem-Behring, San Diego, CA) and applied to a S-Sepharose ®(Sulpho-propyl) (Pharmacia P-L Biochemicals, Piscataway, NJ) column equilibrated in 50 mM MES, pH 6.0 at a protein concentration of 1.5-2.0 mg/ml gel. The sample was eluted using a linear gradient of 0-0.5 M NaCl in 50 mM MES, pH 6.0. Peak fractions which eluted at approximately 0.2 M NaCl were pooled and treated with pAPMSF to 100 μM. Fractions containing sT4 were confirmed by SDS-PAGE and immunoblot assays. After sitting at 4 C for 1 hour the sample was dialyzed against 50 mM Bis-Tris propane [1,3-bis[tris-(hydroxymethyl)methyl amino]-propane], pH 6.0.

The sample was treated with 100 μM pAPMSF and 0.1% thiodiglycol, pH 9.0 was then applied to a Q-Sepharose ® (quarternary amino ethyl) column (Pharmacia) (5 ml sample/ml gel) equilibrated in 50 mM Bis-Tris propane (BTP), pH 9.0. The sT4 sample does not bind to the Q-Sepharose ®and was recovered in the unbound fraction and column wash. The unbound sample was immediately adjusted to pH 6.0.

The final step was chromatography on a 30 micron Superose ®12 column ($2.5 \times 46$ cm) (Pharmacia) equilibrated in 50 mM phosphate, 0.15 M NaCl pH 7.0. The column was run at a flow rate of 3.0 ml/min. Ten ml injections were made and the 42 minute peak was collected batchwise The process yielded approximately 1.0 mg of product per 20.0 mg of total protein for a cell line producing approximately 3 pg/cell/day.

Characterization of the sT4

Physical Properties: Total protein concentration was determined using the colormetric BCA protein assay (Bicinchoninic Acid, Pierce Chemical Co., Rockford, IL). Absolute concentrations were determined by quantititative amino acid analysis. The measured amino acid composition of the purified sT4 was performed using standard amino acid analysis techniques and was found to agree with the predicted sequence for the molecule to within experimental error ($+/-15%$). Through the first 20 residues the sequence was as predicted except that it begins lys-lys-val-val—. Thus, the mature amino terminus begins at position +3 with respect to the predicted leader clip site and differs from the predicted sequence at that position by an asn to lys change. The position of the mature amino terminus agrees well with the determined termini of the mouse and sheep CD4 proteins. The asn to lys change may represent a sequencing error (single base change) or a mutation which arose during recombinant procedures.

Immuno-epitopes: The monoclonal antibodies OKT4 and OKT4A recognize non-interfering surface epitopes of the T4 receptor (114). These antibodies are specific for the native conformation in that they will not bind to reduced, SDS denatured protein in immuno-blot assays. It was shown that both antibodies specifically precipitate sT4 from $^{35}$S-labeled culture supernatants using the following immunoprecipitation procedure:

Cultures of sT4-producing cells containing $1 \times 10^6$ cells per 60 mm culture dish were labeled for 16 hours at 37° C. in 1.5 ml methionine and cysteine free F12 medium containing ITS, and 170 μCi/ml [$^{35}$S]methionine and 30 μCi/ml cysteine (ICN Biomedicals, Inc., Costa Mesa, CA). Clarified medium (100 μl) was diluted with an equal volume of precipitation buffer (10 mM sodium phosphate pH 7.5, 100 mM NaCl, 0.1% NP40 ®, 0.5% non-fat dry milk) and incubated with 3 μg rabbit IgG for 15 min. at 4.C followed by 30 μl (packed volume) of protein A sepharose beads (Pharmacia P-L Biochemicals) for 30 min. at 4° C. The precleared supernatant was incubated with 5 μg of OKT4, OKT4A and OKT8 (gift of P. Rao, Ortho Pharmaceuticals Corp., Raritan, NJ), mouse IgG (Cooper Biomedical, Malvern, PA), or rabbit α-mouse IgG (Cooper Biomedical) for 30 min at 4° C. OKT4, OKT4A, OKT8, mouse IgG, and rabbit α-mouse IgG were precipitated by incubation with 20 μl (packed volume) of protein A sepharose beads for 30 min. at 4° C. Following precipitation, the beads were washed twice with 200 μl precipLitation buffer and once with 200 μl precipitation buffer minus NP-40®and non-fat dry milk. The washed beads were boiled for 5 min. in 20 μl sample buffer (125 mM Tris-HCl pH 6.8, 20% glycerol, 1.4 M β-mercaptoethanol), and the supernatants were analyzed by electrophoresis on a 12.5% SDS-polyacrylamide gel. Similar results were obtained with OKT4B, OKT4C, OKT4D, OKT4E, OKT4F and other Mabs specific for T4. These results suggest that the conformation of sT4 accurately mimics the surface domain of the T4 receptor.

To determine whether sT4 can associate with HIV gp120 and whether this association can inhibit the binding of HIV to T4 cells, approximately 5 micrograms of purified sT4 were absorbed to Sepharose beads coated with OKT4 or control antibody. The beads were then mixed with a lysate of $^{35}$S-methionine labeled HIV. The complex of sT4 with OKT4 coprecipitates only the 120 kd envelope glycoprotein. No viral proteins are precipitated by OKT4 beads in the absence of sT4 or in the presence of control supernatants from the untransfected CHO cells. Furthermore, viral protein is not precipitated if Sepharose beads coated with control mouse immunoglobulin (isotype matched to OKT4) are incubated with sT4. These studies indicate that the sT4 obtained, which is free of other cell surface components present on the surface of T lymphocytes, is capable of specifically associating with the envelope glycoprotein of the AIDS virus.

Cytofluorometry was performed to demonstrate that the interaction of T4 with gp120 of intact HIV abolishes the binding of AIDS virus to the surface of T4+ cells. T4+CEM cells were exposed to HIV in the presence or absence of sT4. Following viral absorption, the cells were washed, exposed to fluorescein conjugated anti-HIV antibody, and analyzed by flow cytometry (Figure 17) (48). In the absence of sT4, HIV binds efficiently to T4+CEM cells. If HIV is preincubated with sT4, the binding of virus to T4 cells is abolished (FIG. 17). Ten nanograms of purified sT4 is sufficient to inhibit the binding of 100 nanograms of viral protein. If the envelope glycoprotein comprises 5% of the total viral protein, an estimated 5:1 molar ratio of T4 to gp120 is capable of complete inhibition of HIV binding to T4+cells.

The ability of sT4 to inhibit the infection of T4+cells by HIV was also studied. Phytohemagglutinin-stimulated human lymphocytes were exposed to serial ten-fold dilutions of an HIV inoculum in the presence or absence of sT4, washed, and plated in microculture. The frequency of infected cultures was determined using an immunoassay 4.8 and 12 days after exposure to virus (47). In this manner the infectious virus titer, ID-50 is defined as the reciprocal of the dilution required to infect 50% of the exposed cell cultures at day 12. In the absence of sT4, the ID-50 observed with the viral inoculum is approximately $10^5$. However, in the presence of 8 micrograms/ml of purified soluble T4, the infectively is diminished by almost 4 logs to an ID-50 of $10^{1.5}$ (FIG. 18). This dramatic reduction in infectivity by HIV is observed throughout the entire course of infection. As a control for nonspecific inhibition or toxic effects of sT4, sT4 was added to cultures 18 hours after the initial exposure to virus. Cultures exposed to sT4 18 hours after infection show only a 1 log inhibition in the ID-50 which presumably results from inhibition of virus spread following the initial inoculation. Thus, the 4 log reduction in virus infectivity observed when virus is preincubated with sT4 is likely to result from the specific association of sT4 with gp120 on the surface of virus. These particles are therefore no longer capable of interacting with the T4 receptor on the cell surface. Four logs of inhibition were observed when $10^5$ infectious particles/ml are preincubated with 8 micrograms/ml of sT4. The viral preparations of $10^5$ infectious partilcles/ml were estimated to contain $10^9$ particles/ml If each particle contains 1,000 envelope glycoproteins, then the inhibition is obtained at a ratio of 100 T4 molecules/molecule of envelope protein.

The availability of relatively large quantities of structurally intact sT4 facilitates the study of the mechanism of interactions of T4 with the surface of both antigen-presenting cells as well as with HIV virus. The specificity of interaction of T4+helper cells with antigen-presenting cells (B cells and macro phages) may result, at least in part, from the association of T4 with class II MHC molecules (105, $10^6$). The availability of significant amounts of purified sT4 permits a direct demonstration of a physical association between T4 and class II MHC molecules.

The ability of sT4 to bind gp120 and inhibit viral infection in vitro indicates that sT4 is an effective anti-viral agent for treating AIDS patients.

EXAMPLE 4

Production of Soluble V1V2J4 Soluble T-4 Fraqments

Construction of Vectors

Construction of psT4BBVIDHFR: To create plasmid psT4BBVIDHFR, plasmid pST4DHFR (described in example 3) was cut with EcoRI and XbaI and the smaller fragment containing the sT-4 coding region was deleted. Plasmid sT4sal was cut with XbaI and BbvI and a 1120 base pair coding fragment containing the sequence for soluble T-4 minus the leader region was isolated. This fragment was ligated to the EcoRI/XbaI-cut pST4DHFR, using a synthetic linker with an EcoRI end, a KpnI site, and a BbvI end. This fragment is compatible with the BbvI overhang on the sT-4 fragment isolated above The resulting plasmid was called pST4BBVIDHFR.

Construction of OMPAST4: To create plasmid OMPAST4, plasmid OMPA.GS was digested with NcoI and SalI and the smaller fragment containing the linker region was deleted. OMPA.GS is a derivative of pASI (Rosenberg et al., *Meth. Enzymol.* 101:123 (1983); U.S. Pat. No. 4,578,355) having a synthetic sequence inserted into the NdeI site at the 3' end of the cII ribosome binding sequence. The synthetic sequence comprises the OMPA leader followed by a multiliner sequence. The synthetic sequence was substantially as follows:

5'-T ATG AAA AAG ACA GCT ATC GCG ATT GCA GTG GCA CTG

GCT GGT TTC GCT ACC GTA GCG CAG GCC GGC TCT AGA GTC GAC

CTA GTT AAC TAG-3'

Plasmid pUCsT4 was cut with NcoI and SalI and the 1149 base pair fragment containing SCD-4 sequence [T-4 nucleotides 124–1257) was isolated. This fragment was ligated to the NcoI/SalI cut OMPA.GS to create OMPAST4.

Construction of OMPAST4BbvI: To create plasmid OMPAS-T4BbvI, plasmid OMPAST4 was cut with NaeI and XBaI. The smaller fragment resulting from this cut, containing the sT-4 coding region was deleted. Plasmid ST4BBVIDHFR was cut with KpnI and the resulting 3' overhang was blunt ended with T4 DNA polymerase. The blunt ended DNA was then cut with XBaI and the 1124 base pair fragment containing the nucleotides 145-1257 of the CT4 cDNA was isolated. The isolated fragment was ligated to the NaeI/XbaI cut OMPAST4 plasmid to create plasmid OMPASTI4B-bVI.

Construction of pucGT4184: To created plasmid pucSt-4184, an EcoRI-NheI fragment from the T-4 cDNA [a 682 bp fragment encoding aminoacids (−23) to (+178)] was ligated to the synthetic linker sk727/725 (NheI and AvaI ends) at the NheI site. sk727/725 codes for T-4 amino acids 179-185). The AvaI end of sk727/725 was ligated to an AvaI-Xba 1 fragment of pUcST4 (comprising bp 1198-1257 of the human cDNA and encoding amino acids 353-371 of the T-4 receptor followed by a TAA termination codon). This sequence, which is flanked by EcoRI and XbaI ends, was inserted into pUC19 at the EcoRI and Xba 1 ends in the puC19 polylinker (sk727/725). sk727/725 is substantially as follows:

5' gaccagaaggaggaggtgcaattgctagtgttcggattgactgccaac 3' gtcttcctcctccacgttaacgatcacaagcctaactgacggttgagc 5'

Construction of pucST410$^6$: To create plasmid pucST-4106, an EcoRI-Ava II fragment (comprising bp 1-413, and encoding amino acids (−) 23-89) of the T-4 cDNA was joined to the synthetic linker sk791/792 (Ava II-AvaI ends) at the AvaII site. sk791-792 codes for T-4 amino acids 90-10$^6$. The AvaI end of sk791/792 was ligated to an AvaI-XbaI fragment of pucST4 (comprising bp 1198-1257 of the human cDNA, and encoding amino acids 353-371 of the T-4 receptor followed by a TAA termination codon). This sequence, which is flanked by EcoRI and XbaI, ends was inserted into pUC19 at the EcoRI and XbaI ends in the puC19 polylinker. sk791/792 is substantially as follows:

5' gaccagaaggaggaggtgcaattgctagtgttcggattgactgccaac gtcttcctcctccacgttaacgatcacaagcctaactgacggttgagc 5'

Construction of sT4184DHFR: To create plasmid sT41-84.DHFR, an EcoRI-XbaI fragment of pucST4184 (encoding amino acids -21 to 186 fused to 355 to 373) was ligated to the EcoRI and XbaI ends of psT4DHFR in place of the EcoRI-XbaI fragment encoding sT-4.

Construction of sT410$^6$DHFR: To create plasmid sT4106.-DHFR an EcoRI-XbaI fragment of pucST4106 (encoding amino acids -23 to 10$^6$ fused to 353 to 371) was ligated to the EcoRI and XbaI ends of psT4DHFR in place of the EcoRI -Xba 1 fragment encoding sT-4.

Expression of pST4184DHFR in Chinese Hamster Ovary (CHO) cells:

DXB-11 cells, a DHFR deficient CHO cell line (Urlaub, et al., supra) were transfected by calcium phosphate precipitation with 10 to 30 μg of pST-4184DHFR in the presence of 10 μg carrier DNA (NIH-3T3 genomic DNA), one day after seeding 60 mm dishes with $5 \times 10^5$ cells Precipitates were removed after 6 hrs. and replaced with F12 medium without hypoxanthine or thymidine, containing 10% dialyzed fetal bovine serum. Colonies (approximately 100 per dish) appeared in 16 days. Colonies from each dish were pooled, expanded and then seeded at $3 \times 10^4$ cells per well in 24 well culture plates. These cells were grown in nucleoside free media containing 80 nM methotrexate (mtx) to select for potential amplification of the transfected dhfr and V1V2J4 minigene. After two weeks in 8 nM mtx, actively growing cells were clearly visible. Individual wells or clones were assayed at confluence for expression of the deletion mutants and those selected for further amplification were seeded into 24 well culture plates at the density described above. A number of subpopulations which expressed high levels of V1V2J4 were grown in increasing levels of mtx to select for further amplification of the dhfr transcription unit and the T4184s(V1V2-J4) minigene.

Several cells lines were derived using this method which expresses the deletion mutants in amounts of at least about 2 pg/cell/24 hrs.

Conditioned medium (CM) was prepared serum-free from adherent cell cultures expanded into 850 cm$^2$ roller bottles under mtx selective conditions. At confluence, the cells were washed twice with phosphate buffered saline (PBS) without Mg$^{2+}$ and Ca$^{2+}$ and the growth medium (Ham's F12 without hypoxanthine and thymidine, 10% fetal bovine serum, 100 units/ml penicillin and streptomycin and mtx at the selective concentration) was replaced with the same medium minus serum and mtx and plus 1 ×ITS (insulin, transferring and selenium (Collaborative Research Inc.). After 24-48 hrs. the medium was removed and replaced with selective growth medium. Serum-free medium was then reapplied within 3-5 days and this cycle repeated indefinitely, i.e., for more than two months. CM was clarified by centrifugation at 8,000 ×g. A protease inhibitor PMSF (phenylmethylsulfonylfluoride) was added to 0.5 mM and the CM was concentrated about 10x fold by pressure membrane filtration. This concentrated CM was clairified by centrifugation at 2000 ×q and Aprotinin, protease inhibitor, (Sigma Chemical, St. Louis, MO) was added to a final concentration of 5 μg/ml. The sample was processed directly or after storage at −70° C.

Western Blot Analysis: Conditioned media from V1V2J4 producing CHO cells was concentrated and run on a 15% polyacrylamide reducing gel. Protein was transferred to nitrocellulose paper and probed with polyclonal antisera raised against a denatured E. coli derived T-4-NSI fusion molecule. This antisera specifically recognizes a V1V2J4 doublet migrating at approximately 25 KD. This corresponds to the predicted size of the V1V2J4 coding sequence after leader processing. The physical basis for the doublet is not known. It is not likely to result from the differences in N-linked glycosylation, since the two consensus sequences in T-4 for this glycosylation are not present in V1V2J4.

Immuno-epitopes: The monoclonal antibodies OKT-4 and OKT-4A, OKT4B, OKT4C, OKT4D, OKT4E and OKT4F specifically recognize surface epitopes on the native, membrane bound T-4 receptor (Rao, et al., Cell Immunol. 80:310(1983)). These antibodies are specific for the native conformation in that they will not bind to reduced, SDS-denatured protein in immuno-blot assays.

It was shown that both antibodies specifically precipitate VIV2J4 from 35S-labelled culture supernatants using the with 200 µl precipitation buffer minus NP-40® and non-fat dry milk. The washed beads were boiled for 5 min in 20 µl sample buffer (125 mM Tris-HCL pH 6.8, 20% glycerol, 1.4 M β-mercaptoethanol), and the supernatants were analyzed by electrophoresis on a 12.5% SDS-polyacrylamide gel. With the exception of OKT4, each of the monoclonal antibodies specifically precipitated the VlV2J4 from 35S-labelled cultured supernatants.

Competition of HIV binding: The recognition of VIV2J4 by OKT4A indicated that V1V2J4 would inhibit the binding of the AIDS virus to susceptible cells. CM containing or lacking VIV2J4 was used in the initial assays. HIV was incubated with the CM and virus binding to the T-4+CEM cell line was quantitated by incubation with a FITC conjugated, anti-HIV antibody and FACS (Fluorescein activated cell sorter) analysis as described by McDougal, et al., supra (1985). CM from the VIV2J4 producing cell line inhibited HIV binding in a dilution dependent manner, whereas no response was seen with CM from matched non-producer (DXB-11) cells.

The protein VIJ4 was similarly expressed in CHO cells. However, in these preliminary experiments, the protein apparently was not exported into the media. Based on other studies showing that VIJ4 produced in other re-combinant organisms binds OKT4A, it appears that VIJ4 expressed in mammalian cell culture would inhibit HIV binding.

EXAMPLE 5

Preparation of Anti-Soluble T4 Fragment Antibodies

Eight week old Balb/c mice are injected intraperitoneally with 50 micrograms of a purified soluble T4 fragment of the present invention (prepared as described above) in complete Freund,s adjuvant, 1:1 by volume. Mice are then boosted, at monthly intervals, with the soluble T4 fragment mixed with incomplete Freund's adjuvant, and bled through the tail vein. Immunoglobulin cuts of sera are generated by ammonium sulfate precipitation and specific anti-soluble T4 fragment antibodies are purfified by affinity chromatography using an immobilized T4 fragment.

EXAMPLE 6

Preparation of Soluble T4 Fragment Anti-Idiotypic Antibodies

Syngenic and congenic mice are injected intraperitoneally with 50 micrograms of a purified anti-soluble T4 fragment antibody, of the present invention (prepared as described above) in complete Freund,s adjuvant and boosted with the anti-soluble T4 fragment antibody in incomplete Freund's adjuvant monthly. On days 4, 3, and 2 prior to fusion, mice are boosted intravenously with 50 micrograms of immunoglobulin in saline. Splenocytes are then fused with P3X63 AG8.653 non-secreting myeloma cells according to procedures which have been described and are known in the art to which this invention pertains. Two weeks later, hybridoma supernatants are screened for binding activity against anti-soluble T4 fragment antibodies by radioimmunoassay. Positive clones are then assayed for the ability to bind a human immunodeficiency virus envelope glycoprotein and AIDS virus. Alternatively, using the "one-step" procedure, mice are injected intraperitoneally with a soluble T4 fragment in complete Freund,s adjuvant, boosted intravenously with the soluble T4 fragment in saline, and mice spleen cells fused with myelomas as above. Hybridoma supernatants are then assayed directly for soluble T4 fragment anti-idiotypic antibodies.

REFERENCES

1. E.L. Reinherz et al., "Discrete Stages of Human Intrathymic Differentiation: Analysis of Normal Thymocyte and Leukemic Lymphoblasts of T Cell Lineage", Proc. Natl. Acad. Sci. USA 77: 1588-1592 (1980).

2. E.L. Reinherz and S.F. Schlossman, "The Differentiation and Function of Human T Lymphocytes", Cell 19: 821-827 (1980).

3. M.L. Blue et al., "Coexpression of T4 and T8 on Peripheral Blood T Cells Demonstrated by Two-color Fluoroescence Flow Cytometry", J. Immunol 134: 2281-2286 (1985)

4. E.G. Enqleman et al., "Activation of Human T Lymphocyte subsets: Helper and Suppressor/Cytotoxic T Cells Recognize and Respond to Distinct Histocompatibility Antigens", J. Immunol. 127: 2124-2129 (1981)

5. A.M. Krensky et al., "Long-term Human Cytolytic T-cell Lines Allospecific for HLA-DR6 Antigen Are OKT4+", Proc. Natl. Acad. Sci. USA 79: 2365-2369 (1982).

6. S.C. Meuer, S.F. Schlossman and E. Reinherz, "Clonal Analysis of Human Cytotoxic T Lymphocytes T4+and T8+Effector T Cells Recognize Products of Different Major Histocompatibility Complex Regions", Proc. Natl. Acad. Sci. USA 79: 4395-4399 (1982).

7. W.E. Biddison et al., "Possible Involvement of the OKT4 Molecule in T Cell Recognition of Class II HLA Antigens", J. Exp. Med. 156: 1065-1076 (1982).

8. D.R. Wilde et al., "Evidence Implicating L3T4 in Class II MHC Antigen Reactivity Monoclonal Antibody GK 15 (Anti-L3T4) Blocks Class II MHC Antigen-Specific Proliferation, Release of Lymphokines and Binding by Cloned Murine Helper T Lymphocyte Lines", J. Immunol. 131:2178-2183 (1983).

9. S.L. Swain, "T Cell Subsets and the Recognition of MHC Class", Immunol. Rev. 74: 129-142 (1983).

10. Y. Thomas et al., "Functional Analysis of Human T Cell Subsets Defined by Monoclonal Antibodies. IV. Induction of Suppressor Cells Within the OKT4 Population", J. Exp. Med. 154: 459-467 (1981).

11. E.G. Engleman et al., "Antibodies to Membrane Structures that Distinguish Suppressor/Cytotoxic and Helper T Lymphocyte Subpopulations Block the Mixed Leukocyte Reaction in Man", J. Exp. Med. 154: 193-198 (1981).

12. p. Marrack et al., "The Major Histocompatibility Complex-restricted Antigen Receptor on T Cells. II. Role of the L3T4 Product", J. Exp. Med. 158: 1077-1091 (1983).

13. L. Rogozinski et al., "The T4 Surface Antigen is Involved in the Induction of Helper Function", J. Immunol. 132: 735-739 (1984).

14. S.L. Swain, "Significance of Lyt Phenotypes: Lyt2 Antibodies Block Activities of T Cells that Recognize Class I Major Histocompatibility Complex Antigens Regardless of Their Function", Proc. Natl. Acad. Sci. USA 78: 7101-7105 (1981).

15. U Landegren et al., "Selective Inhibition of Human T Cell Cytotoxicity at Levels of Target Recognition of Initiation of Lysis by Monoclonal OKT3 and Leu-2a Antibodies", J. Exp. Med. 155: 1579-1584 (1982).

16. R.M. Zinkernagel and P.C. Doherty, "MHC-restricted Cytotoxic T Cells: Studies on the Biological Role of Polymorphic Major Transplantation Antigens Determining T Cell Restriction, Specificity, Function, and Responsiveness", Adv. Immunol. 27: 52-177 (1979).

17. Kappler et al., "The Major Histocompatibility Complex-Restricted Antigen Receptor on T Cells in Mouse and Man: Identification of Constant and Variable Peptides", Cell 35:295-302 (1983).

18. O. Acuto et al., "The Human T Cell Receptor: Appearance in Ontogeny and Biochemical Relationship of Alpha and Beta Subunits on IL-2 Dependent Clones and T Cell Tumors", Cell 34: 717-726 (1983).

19. P. Kavathas et al., "Isolation of the Gene Coding for the Human T Lymphocyte Antigen Leu-2 (T8) by Gene Transfer and cDNA Subtraction", Proc. Natl. Acad. Sci. USA 81: 7688-7692 (1984).

20. D.R. Littman et al., "The Isolation and Sequence of the Gene Encoding T8: A Molecule Defining Functional Classes of T Lymphocytes", Cell 40: 237-246 (1985).

21. V.p Sukhatma et al., "The T Cell Differentiation Antigen Leu-2/T8 is Homologous to Immunoglobulin and T Cell Receptor Variable Regions", Cell 40: 591-597 (1985).

22. S.M. Friedman et al., "TO-CLL: A Human T Cell Chronic Lymphocytic Leukemia That Produces IL-2 in High Titer", J. Immunol. 128:20 935-940 (1982).

23. D.A. Thurley-Lawon, L. Chess and J.L. Strominger, "Suppression of In Vitro Epstein-Barr Infection: A New Role for Adult Human T Cells", J. Exp. Med. 146: 495-508 (1977).

24. J.W. Goding, "The Chromic Chloride Method of Coupling Antigens to Erythrocytes: Definition of Some Important Parameters", J. Immunol. Methods 10: 61-66 (1976).

25. F.L. Graham and A.J. van der Eb, "A New Technique for the Assay of Infectivity of Human Adenovirus DNA", Virology 52: 456-467 (1973).

26. M. Wigler et al., "Biochemical Transfer of Single-Copy Eucaryotic Genes Using Total Cellular DNA as Donor", Cell 14: 725-731 (1978).

27. M. Wigler et al., "Transfer of Purified Herpes Virus Thymidine Kinase Gene to Cul-tured Mouse Cells", Cell 11: 223-232 (1977).

28. J.M. Chirgwin et al., "Isolation of Biologically Active Ribonucleic Acid from Sources Enriched in Ribonuclease", Biochemistry 18:5294-5299 (1979).

29. H. Aviv and P. Leder, "Purification of Biologically Active Globin Messenger RNA by Chromatography on Oligothymidylic Acid-Cellulose", Proc. Natl. Acad. Sci. USA 69: 1408-1412 (1972).

30. T. Huynh, R.A. Young and R.W. Davis, "Construction and Screening cDNA Libraries in gt10 and gt11", DNA Cloninq Techniques A Practical Approach, D.M. Glover, ed. (Oxford: IRL Press), in press.

31. T. Maniatis et al., "The Isolation of Structural Genes from Libraries of Eucaryotic DNA", Cell 15: 687-701 (1978).

32. M.M. Davis et al., "Cell-Type-Specific cDNA Probes and the Murine I Region: the Localization and Orientation of $A^d$ Alpha", Proc. Natl. Acad. Sci. USA 81: 2194-2198 (1984).

33. T. Maniatis, E.F. Fritch and J. Sambrook, Molecular Cloninq (Cold Spring Harbor, NY; Cold Spring Harbor Laboratory) (1982).

34. P.W.J. Rigby et al., "Labeling Deoxyribonucleic Acid to High Specific Activity In Vitro by Nick Translation with DNA Polymerase I", J. Mol. Biol. 113: 237-251 (1977).

35. J. Vieira and J. Messing, "The pUC Plasmids, an M13mp7-Derived System for Insertion Mutagenesis and Sequencing with Synthetic Universal Primers", Gene 19: 259-268 (1982).

36. F. Sanger, S. Nicklen and A. Coulson, "DNA Sequencing with Chain-Terminating Inhibiors", Proc. Natl. Acad. Sci. USA 74: 5463-5467 (1977).

37. E. Southern, "Detection of Specific Sequences Among DNA Fragments Separated by Gel Electrophoroesis", J. Mol. Biol. 98: 503-517 (1975).

38. G.M. Church and W. Gilbert, "Genomic Sequencing", Proc. Natl. Acad. Sci. USA 81: 1991-1995 (1984).

39. R.H. Scheller et al., "A Family of Genes that Codes for ELH, a Neuropeptide Eliciting a Stereotyped Pattern of Behavior in Aplysia", Cell 28: 707-719 (1982).

40. K. Zinn, D. DiMaio and T. Maniatis, "Identification of Two Distinct Regulatory Regions Adjacent to the Human Beta-Interferon Gene", Cell 34: 865-879 (1983).

41. C. Terhorst et al., "Further Structural Studies of the Heavy Chain of HLA Antigens and Its Similarity to Immunoglobulins", Proc. Natl. Acad. Sci. USA 74: 4002-4006 (1977).

42. J.A. Hedo, L.C. Harrison and J. Roth, "Binding of Insulin Receptors to Lectins: Evidence for Common Carbohydrate Determinants on Several Membrane Receptors", Biochemistry 20: 3385-3393 (1981).

43. U.K. Laemmli, "Cleavage of Structural Proteins During the Assembly of the Head of Bacteriophage T4", Nature 227: 680-685 (1970).

44. R. Mann, R.C. Mulligan, and D. Baltimore, Construction of a retrovirus packaging mutant and its use to produce helper-free defective retrovirus, Cell 33, 153-159 (1983).

45. F. Barre-Sinoussi,et al., Isolation of a T lymphotropic retrovirus from a patient at risk for acquired immune deficiecny syndrome 25 (AIDS), Science 220, 868-871 (1983).

46. J.S. McDougal, et al., Cellular tropism of the human retrovirus HTLV-III/LAV. I. Role of T cell activation and expression of the T4 antigen, J. Immol. 135, 3151-3162 (1985).

47. J.S. McDougal, et al., Immunoassay for the detection and quantitation of infectious human retrovirus, lymphadenopathy-associated virus (LAV), J. Immunol. Meth. 76, 171-183 (1985).

48. J.S. McDougal, et al., Binding of HTLV-III/-LAV to T4+T cells by a complex of the 110K viral protein and the T4 molecule, Science 231, 382-385 (1986).

49. C.B. Reimer, et al., Standardization of ligand binding assays for alpha-fetoprotein. In Immunofluorescence and Related Staining Techniques. W., Knapp, K. Holubar, and G. Wick, eds. (Amsterdam:Elsevier/-North Holland Press) p. 189 (1978).

50. M.B Wilson and P.K. Nakane, Recent developments in the periodate method of conjugating horseradish peroxidase (HRPO) to antibodies. In Immunofluorescence and Relating Staining Techniques, W. Knapp, K. Holubar, and G. Wick, eds. (Amsterdam:Elsevier/North Holland Press), p. 215 (1978).

51 J. Porath, R. Axen, and S. Ermback, Chemical coupling of proteins to agar, Nature 215, 25 1491–1493 (1967).

52. B.J. poiesz, et al., Detection and isolation of type C retrovirus particles from fresh and cultured lymphocytes of a patient with cutaneous T cell lymphoma. Proc; Natl. Acd. Aci. USA 77, 7415–7419 (1980).

53. P. Clapham, K. Nagy, and R.A. Weiss, Pseudotypes of human T-cell virus types 1 and 2: Neutralization by pateints, sera, Proc. Natl. Acad. Sci. USA 81, 2886–2889 (1984).

54. A.G. Oalgleish, et al., The CD4 (T4) antigen is an essential component of the receptor for the AIDS retrovirus, Nature 312, 763–766 (1984).

55. M. Popovic, et al., Detection, isolation, and continuous production of cytopathic retorviruses (HTLV-III) from patients with AIDS and Pre-AIDS, Science 224, 497–500 (1984). 56. K. Nagy, et al., Human T-cell leukemia virus type 1: induction of sycytia and inhibition by patients' sera, Int. J. Cancer 32, 321–328 (1983).

57. D.M. Neville and H. Glossman, Molecular weight determination of membrane protein and glycoprotein subunits by discontinuous gel electrophoresis in dodecyl sulfate, Methods Enzymol. 32, 92–102 (1974).

58. A. Helenius, et al., On the entry of Semliki Forest virus into BHK-21 cells, J. Cell. Biol. 84, 404–420 (1980).

59. R.D. Cone and R.C. Mulligan, High-efficiency gene transfer into mammalian cells: Generation of helper-free recombinant retroviruses with broad mammalian host range, Proc. Natl. Acad. Sci. USA 81, 6349–6353 (1984).

60. F.W. Alt et al., "Probes for Specific mRNAs by Subtractive Hybridization: Anomalous Expression of Immunoglobulin Genes", in Eucaryotic Gene Regulation, R.Axel, T.Maniatis and C.F. Fox, eds. (New York: Academic Press), pp. 407–419 (1979).

61. M. Kozak, "Comparison of Initiation of Protein Synthesis in Procaryotes, Eucaryotes and Organelles", Microbiol. Rev. 47: 1–45 (1983).

62. L. Hood, M. Kronenberg and T. Hunkapiller, "T Cell Antigen Receptors and the Immunoglobulin Supergene Family", Cell 40: 225–229 (1985).

63 S Tonegawa, "Somatic Generation of Antibody Diversity", Nature 302: 575–581 (1983).

64. J. Kyte and R.F. Doolittle, "A Simple Method for Displaying the Hydropathic Character of a Protein", J. Mol. Biol. 157: 105–132 (1982).

65. von Heijne, "Patterns of Amino Acids Near Signal-Sequence Cleavage Sites", Eur. J. Biochem 133: 17–21 (1983).

66. E.A. Kabat et al., "Sequences of Proteins of Immunological Interest"(Washington, D.C.; U.S. Department of Health and Human Ser-vices), p. 281 (1983).

67. A.F. Williams et al., "Cell Surface Glycoproteins and the Origins of Immunity", In the Proceedings of the Sigrid Juselius Sym-posium, L.C. Andersson, C.G. Gahmberg and P.

Ekblom, eds. (New York: Academic Press), in press (1984).

68. L.M. Amzel and R.J. Poljak, "Three-Dimensional Structure of Immunoglobulins", Ann. Rev. Biochem. 48: 961–997 (1979).

69. P.Y. Chou and G.D. Fasman, "Empirical Predictions of Protein Conformation", Ann. Rev. Biochem. 47: 251–276 (1978).

70. P.J. Maddon, et al., The isolation and nucleotide sequence of a cDNA encoding the T cell surface protein T4: A new member of the immunoglobulin gene family, Cell 42, 93–104 (1985).

71. R.A. Adams, A. Flowers and B.J. Davis, Direct implantation and serial transplatation of human acute lymphoblastic leukemia in hamsters, SB-2, Can. Res. 28, 1121–1125 (1968).

72. G.O. Gey, W.D. Coffman and M.T. Kubicek, Tissue culture studies of the proliferative capacity of cervical carcinoma and normal epithelium, Cancer Res. 12, 264–265 (1952).

73. R.J.V. Pulvertaft, Cytology of Burkitt's tumor (African lymphoma), Lancet I, 238–240 (1964).

74. N.J. Dimmock, Initial stages of infection with animal viruses, J. Gen. Virol. 59, 1–22 (1982).

75. J. White, M. Kielian and A. Helenius, Membrane fusion proteins of enveloped animal viruses, Quart. Rev. Biophys. 16, 151–195 (1983).

76. M. Marsh, The entry of enveloped viruses into cells by endocytosis, Biochem. J. 218, 1–10 (1984).

77. M. Kielian and A. Helenius, Entry of alphaviruses. In the Togaviridae and Flaviviridae, S. Schlesinger and M.J. Schlesinger, eds., (Plenum Publishing Corp.), pp. 91–119 (1986).

78 S. Ohkuma, and B. Poole, Fluorescence probe measurements of the intralysosomal pH in living cells and the pertubation of pH by various agents, Proc. Natl. Acad. Sci. USA 75, 3327–3331 (1978).

79. F.R. Maxfield, Weak bases and ionophore rapidly and reversibly raise the pH of endocytic vesicles in cultured mouse fibroblasts, J. Cell. Biol. 95, 676–681 (1982).

80. A. Helenius, M. Marsh, and J. White, Inhibition of Semliki Forest virus penetration by lysosomotropic weak bases, J. Gen. Virol. 58, 47–61 (1982).

81. R.T. Johnson and J.C. McArthur, AIDS and the brain, TINS 9, 91–94 (1986).

82. P.M. Snow, M. Van de Rijn and C. Terhorst, "Association Between the Human Thymic Differentiation Antigens T6 and T8", Eur. J. Immunol., in press (1985).

83. P M Snow and C. Terhorst, "The T8 Antigen is a Multimeric Complex of Two Distinct Subunits on Human Thymocytes but Consists of Homomultimeric Forms on Peripheral Blood T Lymphocytes", J. Biol. Chem. 258: 14675–14681 (1983).

84. C. Terhorst et al., "Biochemical Analysis of Human T Lymphocyte Differentiation Antigens T4 and T5", Science 209: 520–521 (1980).

85. W.H. Hildemann, "Immunocompetance and Allogeneic Polymorphism Among Invertebrates", Transplantation 27: 1–3 (1979). 86. V.L. Scofield et al., "Protochordate Allorecognition is Controlled by a MHC-like Gene System", Nature 295: 499–502 (1982).

87. T.L. Lentz, et al., Is the acetylcholine receptor a rabies virus receptor ? , Science 215, 182–184 (1982).

88. J.D. Fingeroth, et al., Epstein-Barr virus receptor of human B lymphocytes is the C3d receptor CR2, Proc. Natl. Acad, Sci. USA 81, 4510–4514 (1984).

89. P.E. Tambourin, et al., The physiopathology of Friend leukemia, Leukemia Res. 3, 117–129 (1979).

90. A. Oliff, et al., Isolation of transplantable erythroleukemia cells from mice infected with helper-independent Friend murine leukemia virus, Blood 58, 244–254 (1981).

91. J.E. Silver and J.M. Fredrickson, Susceptibility to Friend helper virus leukemias in CXB recombinant inbred mice, J. Exp. Med. 10 158, 1693-1702 (1983).

92. P.A. Chatis, et al., Role for the 3, end of the genome in determining disease specificity of Friend and Moloney murine leukemia viruses, Proc. Natl. Acad. Sci, USA. 80, 4408-4411 (1983).

93. P.A. Chatis, et al., A 3, end fragment encompassing the transcriptional enhancers of nondefective Friend virus confers erthyroleukemogenicity on Moloney leukemia virus, J. Virol. 52, 248-254(1982).

94. . Bosze, H.J. Thiesen and P. Charnay, A transcriptional enhancer with specificity for erythroid cells is located in the long terminal repeat of the Friend murine leukemia virus, EMBO J. 5, 1616-1623(1986).

95. A.N. Barclay, et al., Immunoglobulin-related structures associated with vertebrate cell surfaces, in press.

96. M.O. Dayoff, W.C. Barker and L.T. Hunt, Establishing homologies in protein sequences. In Methods in Enzymology. Enzyme Structure Part I, C.H.W. Hirs and S.N. Timasheff, eds. (NY: Academic Press), pp. 525-545 (1983).

97. Y. Yanagi, et al., A human T cell-specific cDNA clone encodes a protein having extensive homology to immunoglobuling chains, Nature 308, 145-149 (1984).

98. G.K. Sim, et al., Primary structure of human T-cell receptor -chain, Nature 312, 771-775 (1084).

99. H. Saito, et al., A third rearranged and expressed gene in a clone of cytotoxic T lymphocytes, Nature 312, 36-40 (1984).

100. H. Saito, et al., Complete primary structure of the E chain and gene of the mouse major histocompatibility complex, Proc. Natl. Acad. USA 80, 5520-5524 (1983).

101. M. Isobe, et al., The gene encoding the T-cell surface protein T4 is located on human chromsome 12, Proc. Natl. Acad. Sci. USA, 83, 4399-4402 (1986).

102. J.M. Roberts and R. Axel, Gene amplification and Gene Correction in Somatic Cells, Cell 29, 109-119 (1982).

103. D.S. Pfarr, G. Sathe and M.E. Reff, A Highly Modular Cloning Vector for the Analysis of Eucaryotic Genes and Gene Regluatory Elements, DNA, 4, 461-467 (1985).

104. G Urlaub and L.A. Chasin, Isolation of Chinese Hamster Cell Mutants Deficient In Dihydrofolate Reductase Activity, Proc. Natl. Acad. Sci. USA, 77, 4216-4220 (1980).

105. Gay, D. ®t al., Nature 328: 626-629 (1987).

106. Sleckman, B.D. et al., Nature 328: 351-353 (1987).

107. Yanisch-Perron, et al., Gene 33: 103 (1985).

108. Berg, P., et al. Mol. Cell. Biol. 3: 246 (1983).

109. Subramani, et al., Mol. Cell Biol. 1: 854 (1981).

110. Frayne, et al., Mol. Cell Biol. 4:2921 (1984).

111. Schumperli, et al., Proc. Natl. Acad. Sci. USA 79: 257 (1982).

112. Gross, et al., Mol. Cell Biol. 5:1015 (1985)

113. Pfarr, et al., DNA 5: 115 (1986).

114. Rao, et al., Cell Immunol. 80: 310 (1983).

115. McClure, et al., Cold Spring Harbor conference on Cell Proliferation 9: 345 (1982).

116. Urlaub, et al., Cell 33: 405 (1983).

117. Kim, et al., Cell 42: 129 (1987).

118. Wigler, et al., PNAS USA 76: 1373 (1979).

119. Copeland, et al., Cell 17: 993 (1979).

120. Sattentau, et al., Science 234: 1120 (1986).

121. Greenstein, et al., Ann. Inst. Pastuer 138: (1987).

122. Gay, et al., Ann. I9nst. Pasteur 138: 127 (1987).

What is claimed is:

1. A polypeptide, the amino acid sequence of which consists essentially of the amino acid sequence shown in FIG. 6 from +1 to +183 directly fused to the amino acid sequence from +353 to +371.

2. A polypeptide, the amino acid sequence of which consists essentially of the amino acid sequence shown in FIG. 6 from +1 to +106 directly fused to the amino acid sequence from +353 to +371.

3. A polypeptide, the amino acid sequence of which consists essentially of the amino acid sequence shown in FIG. 6 from +1 to +185.

* * * * *